(12) United States Patent
McCabe et al.

(10) Patent No.: US 9,752,118 B2
(45) Date of Patent: Sep. 5, 2017

(54) METHOD OF DIRECTED DIFFERENTIATION PRODUCING CORNEAL ENDOTHELIAL CELLS FROM NEURAL CREST STEM CELLS BY PDGFB AND DKK2, COMPOSITIONS THEREOF, AND USES THEREOF

(71) Applicant: Astellas Institute for Regenerative Medicine, Marlborough, MA (US)

(72) Inventors: Kathryn L. McCabe, Westborough, MA (US); Shi-Jiang Lu, Shrewsbury, MA (US); Robert P. Lanza, Clinton, MA (US)

(73) Assignee: Astellas Institute for Regenerative Medicine, Marlborough, MA (US)

( * ) Notice: Subject to any disclaimer, the term of this patent is extended or adjusted under 35 U.S.C. 154(b) by 0 days.

(21) Appl. No.: 14/362,775

(22) PCT Filed: Dec. 6, 2012

(86) PCT No.: PCT/US2012/068305
§ 371 (c)(1),
(2) Date: Jun. 4, 2014

(87) PCT Pub. No.: WO2013/086236
PCT Pub. Date: Jun. 13, 2013

(65) Prior Publication Data
US 2014/0370007 A1 Dec. 18, 2014

(51) Int. Cl.
| | | |
|---|---|---|
| *C12N 5/071* | (2010.01) | |
| *C12N 5/07* | (2010.01) | |
| *C12N 5/16* | (2006.01) | |
| *C12N 5/074* | (2010.01) | |
| *C12N 5/079* | (2010.01) | |
| *A61K 35/30* | (2015.01) | |
| *A61L 27/38* | (2006.01) | |
| *A61K 9/00* | (2006.01) | |
| *A61K 45/06* | (2006.01) | |
| *C12N 5/0797* | (2010.01) | |

(52) U.S. Cl.
CPC .......... *C12N 5/0621* (2013.01); *A61K 9/0048* (2013.01); *A61K 35/30* (2013.01); *A61K 45/06* (2013.01); *A61L 27/3808* (2013.01); *A61L 27/3839* (2013.01); *A61L 27/3895* (2013.01); *C12N 5/0623* (2013.01); *A61L 2430/16* (2013.01); *C12N 2500/60* (2013.01); *C12N 2500/90* (2013.01); *C12N 2501/115* (2013.01); *C12N 2501/135* (2013.01); *C12N 2501/15* (2013.01); *C12N 2501/155* (2013.01); *C12N 2501/40* (2013.01); *C12N 2501/415* (2013.01); *C12N 2501/727* (2013.01); *C12N 2501/999* (2013.01); *C12N 2506/02* (2013.01); *C12N 2506/08* (2013.01); *C12N 2506/45* (2013.01); *C12N 2533/50* (2013.01)

(58) Field of Classification Search
CPC ............. A61L 27/3808; A61L 27/3895; A61L 27/3604; C12N 5/0621; C12N 5/0623; C12N 5/0696; C12N 2506/45; C12N 2506/02; A61K 35/12; A61K 9/0048; G01N 2800/16; G01N 33/56966; A61F 2/142

See application file for complete search history.

(56) References Cited

U.S. PATENT DOCUMENTS

| | | |
|---|---|---|
| 4,959,319 A | 9/1990 | Skelnik et al. |
| 5,166,048 A | 11/1992 | Soll et al. |
| 5,269,812 A | 12/1993 | White |
| 5,310,728 A | 5/1994 | Shimizu et al. |
| 5,584,881 A | 12/1996 | Rowsey |
| 5,589,451 A | 12/1996 | Wilson |
| 5,649,944 A | 7/1997 | Collins |
| 5,686,414 A | 11/1997 | Scannon |
| 5,703,047 A | 12/1997 | Wilson |
| 5,755,785 A | 5/1998 | Rowsey et al. |
| 6,541,256 B1 | 4/2003 | Chen et al. |
| 6,548,059 B1 | 4/2003 | Joyce et al. |
| 7,147,648 B2 | 12/2006 | Lin |
| 7,300,653 B2 | 11/2007 | Wiegand et al. |
| 7,300,654 B2 | 11/2007 | Wiegand et al. |
| 7,371,513 B2 | 5/2008 | Steinhardt |
| 7,959,939 B2 | 6/2011 | Yamagami |
| 8,642,334 B2 * | 2/2014 | Chambers ............ C12N 5/0619 435/325 |
| 9,096,832 B2 * | 8/2015 | Xu ........................ C12N 5/0676 |
| 2005/0214259 A1 * | 9/2005 | Sano ................... A61L 27/3808 424/93.7 |
| 2006/0068496 A1 * | 3/2006 | Kelly ..................... C12N 5/0611 435/455 |
| 2006/0100612 A1 | 5/2006 | Van der Heyd et al. |
| 2006/0216821 A1 * | 9/2006 | Totey ................... C12N 5/0607 435/368 |
| 2006/0228693 A1 | 10/2006 | Soll |
| 2006/0240552 A1 | 10/2006 | Yamato et al. |
| 2006/0257382 A1 | 11/2006 | Williams et al. |
| 2007/0092550 A1 | 4/2007 | Lui |
| 2007/0128722 A1 * | 6/2007 | Lin ...................... C12N 5/0663 435/366 |
| 2007/0148137 A1 | 6/2007 | Okano et al. |
| 2007/0207127 A1 * | 9/2007 | Kato .................... C12N 5/0605 424/93.7 |

(Continued)

FOREIGN PATENT DOCUMENTS

| | | | | |
|---|---|---|---|---|
| JP | 2009-268433 | * | 11/2009 | ............... C12N 5/06 |
| WO | WO 2007127975 A2 | * | 11/2007 | ......... A61L 27/3604 |

(Continued)

OTHER PUBLICATIONS

JP2009-268433 (Nishida et al., published Nov. 19, 2009)—English version.*

(Continued)

*Primary Examiner* — Chang-Yu Wang
(74) *Attorney, Agent, or Firm* — Wolf, Greenfield & Sacks, P.C.

(57) ABSTRACT

This disclosure generally relates to cell-based therapies for treatment of visual disorders, including disorders of the cornea. Methods are exemplified for directed differentiation of corneal cells from stem cells. Compositions of corneal endothelial cells and uses thereof are also provided. Exemplary compositions exhibit improved cell density and/or more "youthful" gene expression relative to cells obtained from donated tissue.

9 Claims, 45 Drawing Sheets

(56) References Cited

U.S. PATENT DOCUMENTS

| | | | |
|---|---|---|---|
| 2007/0254361 A1* | 11/2007 | Tsai | A61L 27/3808 435/368 |
| 2007/0275365 A1 | 11/2007 | Lui | |
| 2008/0214614 A1* | 9/2008 | Lampe | A61K 9/0048 514/322 |
| 2009/0222086 A1 | 9/2009 | Lui et al. | |
| 2009/0232772 A1* | 9/2009 | Amano | A61K 35/44 424/93.7 |
| 2009/0263465 A1 | 10/2009 | Hsiue et al. | |
| 2009/0270982 A1 | 10/2009 | Torres et al. | |
| 2010/0003299 A1 | 1/2010 | Tseng et al. | |
| 2010/0022517 A1* | 1/2010 | Richards | A61K 9/0048 514/217.09 |
| 2010/0069915 A1 | 3/2010 | Shiuey | |
| 2010/0184221 A1* | 7/2010 | Yokoo | C12N 5/0621 435/395 |
| 2010/0209402 A1* | 8/2010 | Koizumi | A61K 9/0048 424/93.7 |
| 2010/0215717 A1 | 8/2010 | Soker et al. | |
| 2010/0233240 A1 | 9/2010 | Koizumi et al. | |
| 2010/0297234 A1* | 11/2010 | Sugino | C12N 5/0068 424/484 |
| 2011/0009488 A1 | 1/2011 | Bazan et al. | |
| 2011/0143415 A1* | 6/2011 | Paylian | C12N 5/0696 435/173.6 |
| 2011/0166650 A1 | 7/2011 | Busin | |
| 2012/0028933 A1* | 2/2012 | Baust | A61K 31/05 514/167 |
| 2012/0149598 A1* | 6/2012 | Inoue | C12N 5/0621 506/10 |
| 2012/0207744 A1* | 8/2012 | Mendlein | C12N 5/0696 424/130.1 |
| 2012/0219535 A1* | 8/2012 | Maxson, Jr. | C12N 5/0623 424/93.7 |
| 2012/0282318 A1* | 11/2012 | Nishida | A61L 27/222 424/443 |
| 2012/0288482 A1* | 11/2012 | Takahashi | A61K 9/0048 424/93.7 |
| 2013/0108590 A1* | 5/2013 | Takahashi | A61L 27/3808 424/93.7 |
| 2013/0302824 A1* | 11/2013 | Klimanskaya | G01N 33/56966 435/7.21 |
| 2014/0170751 A1* | 6/2014 | Hayashi et al. | 435/377 |

FOREIGN PATENT DOCUMENTS

| | | |
|---|---|---|
| WO | WO 2010/096496 A2 | 8/2010 |
| WO | WO 2011/041062 A1 | 4/2011 |
| WO | WO 2011/149762 A2 | 12/2011 |
| WO | WO 2012/012803 A2 | 1/2012 |

OTHER PUBLICATIONS

Crane et al. Annu. Rev. Cell Dev. Biol. 2006; 22:267-86.*
Hoppenreijs et al. IOVS 1994; 35:150-161.*
Li et al. PNAS, 2011; 108:8299-8304.*
Burgess et al. J of Cell Bio. 1990, 111:2129-2138.*
Bowie et al. Science, 1990, 247:1306-1310.*
Pawson et al. 2003, Science 300:445-452.*
International Search Report mailed May 30, 2013 for Application No. PCT/US2012/068305.
Extended European Search Report mailed Jun. 29, 2015 for Application No. EP 12856068.7.
Blauwkamp et al., Endogenous Wnt signalling in human embryonic stem cells generates an equilibrium of distinct lineage-specified progenitors. Nat Commun. 2012;3:1070. doi: 10.1038/ncomms2064.
Chen et al., Neutralization of mouse interleukin-17 bioactivity inhibits corneal allograft rejection. Mol Vis. 2011;17:2148-56. Epub Aug. 11, 2011.
Crane et al., Neural crest stem and progenitor cells. Annu Rev Cell Dev Biol. 2006;22:267-86. Abstract Only.
Da Silva et al., Smart thermoresponsive coatings and surfaces for tissue engineering: switching cell-material boundaries. Trends Biotechnol. Dec. 2007;25(12):577-83. Epub Nov. 8, 2007. Abstract Only.
Gage et al., The canonical Wnt signaling antagonist DKK2 is an essential effector of PITX2 function during normal eye development. Dev Biol. May 1, 2008;317(1):310-24. doi: 10.1016/j.ydbio.2008.02.030. Epub Mar. 4, 2008.
Gao et al., In vitro culture of human fetal corneal endothelial cells. Graefes Arch Clin Exp Ophthalmol May 2011;249(5):663-9. doi: 10.1007/s00417-010-1547-y. Epub Dec. 21, 2010.
Gospodarowicz et al., Transplantation of cultured bovine corneal endothelial cells to rabbit cornea: clinical implications for human studies. Proc Natl Acad Sci U S A. Jan. 1979;76(1):464-8.
Gwak et al., Small molecule-based promotion of PKCα-mediated β-catenin degradation suppresses the proliferation of CRT-positive cancer cells. PLoS One. 2012;7(10):e46697. doi: 10.1371/journal.pone.0046697. Epub Oct. 5, 2012.
Hasagawa et al., Wnt signaling orchestration with a small molecule DYRK inhibitor provides long-term xeno-free human pluripotent cell expansion. Stem Cells Transl Med. Jan. 2012;1(1):18-28. doi: 10.5966/sctm.2011-0033. Epub Dec. 7, 2011.
Hayashi et al., Immunologic mechanisms of corneal allografts reconstituted from cultured allogeneic endothelial cells in an immune-privileged site. Invest Ophthalmol Vis Sci. Jul. 2009;50(7):3151-8. doi: 10.1167/iovs.08-2530. Epub Feb. 28, 2009.
Hitani et al., Transplantation of a sheet of human corneal endothelial cell in a rabbit model. Mol Vis. Jan. 3, 2008;14:1-9.
Honda et al., Descemet stripping automated endothelial keratoplasty using cultured corneal endothelial cells in a rabbit model. Arch Ophthalmol. Oct. 2009;127(10):1321-6. doi: 10.1001/archophthalmol.2009.253.
Hsiue et al., A novel strategy for corneal endothelial reconstruction with a bioengineered cell sheet. Transplantation. Feb. 15, 2006;81(3):473-6. Abstract Only.
Ide et al., Structural characterization of bioengineered human corneal endothelial cell sheets fabricated on temperature-responsive culture dishes. Biomaterials. Feb. 2006;27(4):607-14. Epub Aug. 15, 2005. Abstract Only.
Iida et al., FH535 inhibited migration and growth of breast cancer cells. PLoS One. 2012;7(9):e44418. doi: 10.1371/journal.pone.0044418. Epub Sep. 11, 2012.
Joyce et al., Age-related gene response of human corneal endothelium to oxidative stress and DNA damage. Invest Ophthalmol Vis Sci. Mar. 1, 2011;52(3):1641-9. doi: 10.1167/iovs.10-6492.
Joyce et al., Decreasing expression of the G1-phase inhibitors, p21Cip1 and p16INK4a, promotes division of corneal endothelial cells from older donors. Mol Vis. May 25, 2010;16:897-906.
Ju et al., Derivation of corneal endothelial cell-like cells from rat neural crest cells in vitro. PLoS One. 2012;7(7):e42378. doi: 10.1371/journal.pone.0042378. Epub Jul. 31, 2012.
Koizumi et al., Cultivated corneal endothelial cell sheet transplantation in a primate model. Invest Ophthalmol Vis Sci. Oct. 2007;48(10):4519-26.
Koizumi et al., Cultivated corneal endothelial transplantation in a primate: possible future clinical application in corneal endothelial regenerative medicine. Cornea. Sep. 2008;27 Suppl 1:S48-55. doi: 10.1097/ICO.0b013e31817f2298. PubMed PMID: 18813075. Abstract Only.
Lai et al., Tissue-engineered human corneal endothelial cell sheet transplantation in a rabbit model using functional biomaterials. Transplantation. Nov. 27, 2007;84(10):1222-32. Abstract Only.
Lee et al., Directed differentiation and transplantation of human embryonic stem cell-derived motoneurons. Stem Cells. Aug. 2007;25(8):1931-9. Epub May 3, 2007.
Li et al., Rapid induction and long-term self-renewal of primitive neural precursors from human embryonic stem cells by small molecule inhibitors. Proc Natl Acad Sci U S A. May 17, 2011;108(20):8299-304. doi: 10.1073/pnas.1014041108. Epub Apr. 27, 2011.

(56) References Cited

OTHER PUBLICATIONS

Luo et al., Cloning, expression and functional analyses of human platelet-derived growth factor-B chain peptide for wound repair of cat corneal endothelial cells. Chin J Traumatol. Feb. 2009;12(1):31-7.

Menendez et al., Wnt signaling and a Smad pathway blockade direct the differentiation of human pluripotent stem cells to multipotent neural crest cells. Proc Natl Acad Sci U S A. Nov. 29, 2011;108(48):19240-5. doi: 10.1073/pnas.1113746108. Epub Nov. 14, 2011.

Mimura et al., Transplantation of corneas reconstructed with cultured adult human corneal endothelial cells in nude rats. Exp Eye Res. Aug. 2004;79(2):231-7. Abstract Only.

Mimura et al., Treatment of rabbit bullous keratopathy with precursors derived from cultured human corneal endothelium. Invest Ophthalmol Vis Sci. Oct. 2005;46(10):3637-44.

Nagoshi et al., Neural crest-derived stem cells display a wide variety of characteristics. J Cell Biochem. Aug. 15, 2009;107(6):1046-52. doi: 10.1002/jcb.22213. Abstract Only.

Nishida et al., Corneal reconstruction with tissue-engineered cell sheets composed of autologous oral mucosal epithelium. N Engl J Med. Sep. 16, 2004;351(12):1187-96.

Nishida et al., Functional bioengineered corneal epithelial sheet grafts from corneal stem cells expanded ex vivo on a temperature-responsive cell culture surface. Transplantation. Feb. 15, 2004;77(3):379-85. Abstract Only.

Okumura et al., Enhancement of corneal endothelium wound healing by Rho-associated kinase (ROCK) inhibitor eye drops. Br J Ophthalmol. Jul. 2011;95(7):1006-9. doi: 10.1136/bjo.2010.194571. Epub Mar. 11, 2011. Abstract Only.

Okumura et al., Enhancement on primate corneal endothelial cell survival in vitro by a ROCK inhibitor. Invest Ophthalmol Vis Sci. Aug. 2009;50(8):3680-7. doi: 10.1167/iovs.08-2634. Epub Apr. 22, 2009.

Peh et al., Human corneal endothelial cell expansion for corneal endothelium transplantation: an overview. Transplantation. Apr. 27, 2011;91(8):811-9. doi: 10.1097/TP.0b013e3182111f01.

Redmond et al., Age-related decrease in human corneal γ-glutamyltranspeptidase activity. Cornea. May 2013;32(5):e121-6. doi: 10.1097/ICO.0b013e3182656881. Abstract Only.

Senoo et al., EDTA: a promoter of proliferation in human corneal endothelium. Invest Ophthalmol Vis Sci. Sep. 2000;41(10):2930-5.

Shao et al., Bone marrow-derived endothelial progenitor cells: a promising therapeutic alternative for corneal endothelial dysfunction. Cells Tissues Organs. 2011;193(4):253-63. doi: 10.1159/000319797. Epub Oct. 20, 2010.

Shimmura et al., Transplantation of corneal endothelium with Descemet's membrane using a hyroxyethyl methacrylate polymer as a carrier. Br J Ophthalmol. Feb. 2005;89(2):134-7.

Sieber-Blum, Epidermal neural crest stem cells and their use in mouse models of spinal cord injury. Brain Res Bull. Oct. 30, 2010;83(5):189-93. doi: 10.1016/j.brainresbull.2010.07.002. Epub Jul. 14, 2010. Abstract Only.

Sugino et al., A method to enhance cell survival on Bruch's membrane in eyes affected by age and age-related macular degeneration. Invest Ophthalmol Vis Sci. Dec. 20, 2011;52(13):9598-609. doi: 10.1167/iovs.11-8400.

Sumide et al., Functional human corneal endothelial cell sheets harvested from temperature-responsive culture surfaces. FASEB J. Feb. 2006;20(2):392-4. Epub Dec. 9, 2005. 23 Pages.

Tchah, Heterologous corneal endothelial cell transplantation—human corneal endothelial cell transplantation in Lewis rats. J Korean Med Sci. Dec. 1992;7(4):337-42.

Wang et al., Derivation of smooth muscle cells with neural crest origin from human induced pluripotent stem cells. Cells Tissues Organs. 2012;195(1-2):5-14. doi: 10.1159/000331412. Epub Oct. 14, 2011.

Wang et al., High expression of pl6INK4a and low expression of Bmi1 are associated with endothelial cellular senescence in the human cornea. Mol Vis. 2012;18:803-15. Epub Apr. 3, 2012.

Wilson et al., Hepatocyte growth factor, keratinocyte growth factor, their receptors, fibroblast growth factor receptor-2, and the cells of the cornea. Invest Ophthalmol Vis Sci. Jul. 1993;34(8):2544-61.

Zhao et al., A high-throughput screen for Wnt/β-catenin signaling pathway modulators in human iPSC-derived neural progenitors. J Biomol Screen. Oct. 2012;17(9):1252-63. Epub Aug. 24, 2012.

Homma et al., "Induction of epithelial progenitors in vitro from mouse embryonic stem cells and application for reconstruction of damaged cornea in mice", Investigative Ophthalmology & Visual Science, Dec. 2004, 45(12):4320-26.

Shin et al., "Protective effect of clusterin on oxidative stress-induced cell death of human corneal endothelial cells," Molecular Vision, Dec. 12, 2009, 15:2789-95.

McCabe et al., Efficient Generation of Human Embryonic Stem Cell-Derived Corneal Endothelial Cells by Directed Differentiation PLoS One. Dec. 21, 2015;10(12):e0145266. doi: 10.1371/journal.pone.0145266. eCollection 2015.

* cited by examiner

FIG. 1
A
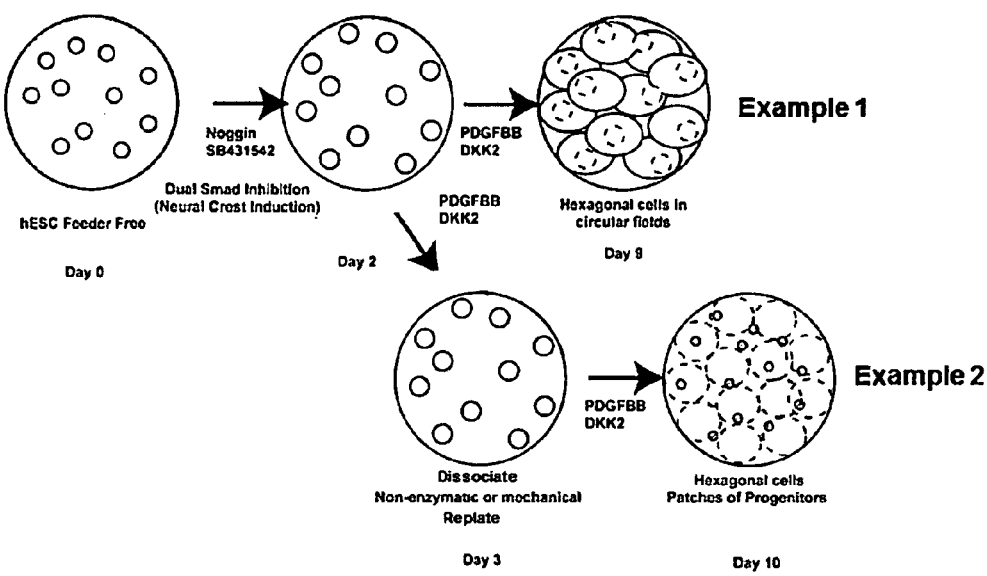
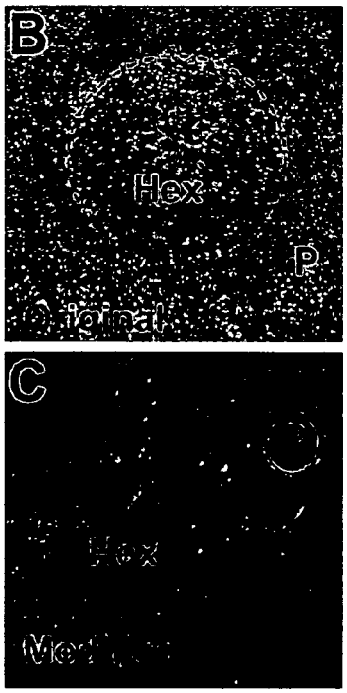

Figure 10. Corneal endothelial cells express the transcription factors PITX2 and FOXC1, markers of ocular neural crest during development. RQ= relative quantification by QPCR.

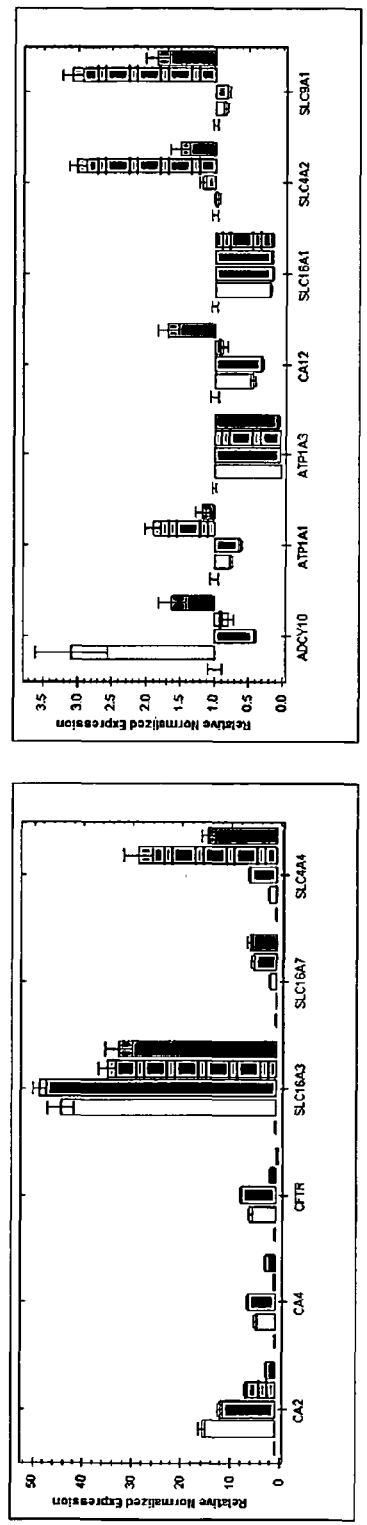
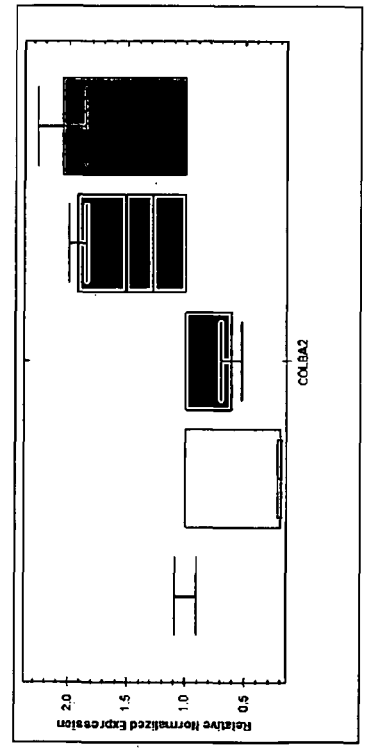
FIG. 16

FIG. 17
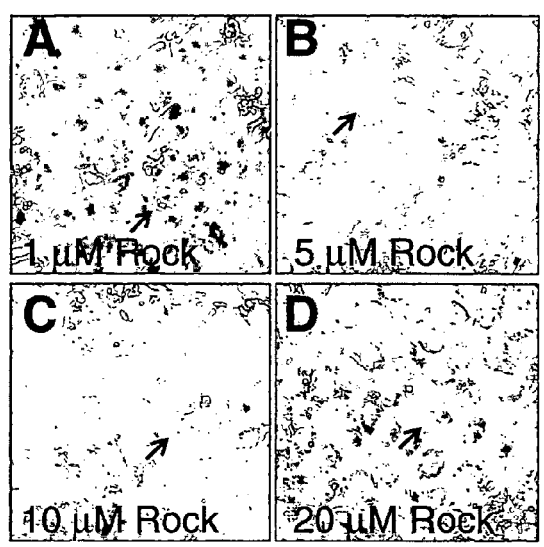
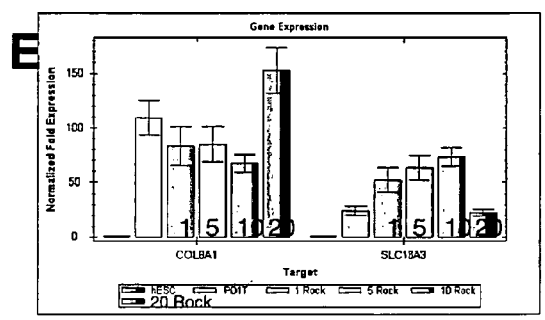
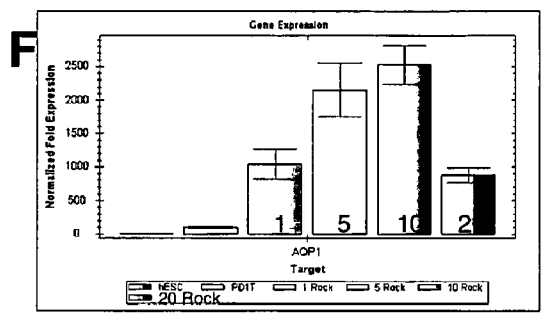

FIG. 20 (1)

| genesymbol | genedescription | Accession number | Fold Change |
|---|---|---|---|
| PRKCZ | protein kinase C, zeta | NM_002744 | 16.45 |
| GRHL3 | grainyhead-like 3 (Drosophila) | NM_198173 | 12.71 |
| CNKSR1 | connector enhancer of kinase suppressor of Ras 1 | NM_006314 | 11.10 |
| SFN | stratifin | NM_006142 | 10.50 |
| SCARNA1 | small Cajal body-specific RNA 1 | | 10.02 |
| TINAGL1 | tubulointerstitial nephritis antigen-like 1 | NM_022164 | 9.97 |
| PTPRF | protein tyrosine phosphatase, receptor type, F | NM_002840 | 9.85 |
| INADL | InaD-like (Drosophila) | NM_176877 | 9.79 |
| ARID3B | AT rich interactive domain 3B (BRIGHT-like) | NM_006465 | 9.66 |
| TMEM56 | transmembrane protein 56 | NM_152487 | 9.54 |
| LPPR4 | lipid phosphate phosphatase-related protein type 4 | NM_014839 | 9.42 |
| C1orf88 | chromosome 1 open reading frame 88 | | 9.41 |
| PHGDH | phosphoglycerate dehydrogenase | NM_006623 | 9.39 |
| Tr. 7904959 | | | 9.35 |
| BNIPL | BCL2/adenovirus E1B 19kD interacting protein like | NM_001159642 | 9.31 |
| CGN | cingulin | NM_020770 | 9.27 |
| RALGPS2 | Ral GEF with PH domain and SH3 binding motif 2 | NM_152663 | 9.22 |
| ELF3 | E74-like factor 3 (ets domain transcription factor, epithelial-specific) | NM_001114309 | 9.17 |
| FAM46B | family with sequence similarity 46, member B | | 8.78 |
| NKAIN1 | Na+/K+ transporting ATPase interacting 1 | | 8.76 |
| RSPO1 | R-spondin homolog (Xenopus laevis) | NM_001038633 | 8.52 |
| C1orf210 | chromosome 1 open reading frame 210 | | 8.10 |
| KANK4 | KN motif and ankyrin repeat domains 4 | | 8.07 |
| SYDE2 | synapse defective 1, Rho GTPase, homolog 2 (C. elegans) | NM_032184 | 8.03 |
| ABCA4 | ATP-binding cassette, sub-family A (ABC1), member 4 | NM_000350 | 8.03 |
| F3 | coagulation factor III (thromboplastin, tissue factor) | NM_001993 | 8.02 |
| FRRS1 | ferric-chelate reductase 1 | NM_001013660 | 7.98 |
| TBX15 | T-box 15 | NM_152380 | 7.94 |
| CRABP2 | cellular retinoic acid binding protein 2 | NM_001878 | 7.89 |
| F11R|TSTD1 | F11 receptor | thiosulfate sulfurtransferase (rhodanese)-like domain containing 1 | NM_016946 | 7.86 |
| PVRL4 | poliovirus receptor-related 4 | NM_030916 | 7.83 |
| APOA2 | apolipoprotein A-II | NM_001643 | 7.82 |
| TNNT2 | troponin T type 2 (cardiac) | NM_000364 | 7.80 |
| LAD1 | ladinin 1 | | 7.65 |
| LMOD1 | leiomodin 1 (smooth muscle) | NM_012134 | 7.59 |
| IRF6 | interferon regulatory factor 6 | NM_006147 | 7.58 |
| Tr. 7924069 | | | 7.49 |
| LBR | lamin B receptor | | 7.47 |
| C1orf198 | chromosome 1 open reading frame 198 | | 7.44 |
| FAM89A | family with sequence similarity 89, member A | | 7.38 |
| GNG4 | guanine nucleotide binding protein (G protein), gamma 4 | NM_001098721 | 7.34 |
| NET1 | neuroepithelial cell transforming 1 | NM_001047160 | 7.17 |
| BAMBI | BMP and activin membrane-bound inhibitor homolog (Xenopus laevis) | NM_012342 | 7.15 |

FIG. 20 (2)

| genesymbol | genedescription | Accession number | Fold Change |
|---|---|---|---|
| ANXA8L2\|ANXA8L1 | annexin A8-like 2 \| annexin A8 \| annexin A8-like 1 | | 7.09 |
| ANXA8\|ANXA8L1\|ANXA8L2 | annexin A8 \| annexin A8-like 1 \| annexin A8-like 2 | | 7.07 |
| TET1 | tet oncogene 1 | NM_030625 | 7.06 |
| ENTPD1 | ectonucleoside triphosphate diphosphohydrolase 1 | NM_001776 | 7.06 |
| ATRNL1 | attractin-like 1 | NM_207303 | 7.04 |
| ITIH5 | inter-alpha (globulin) inhibitor H5 | NM_030569 | 6.98 |
| ITGA8 | integrin, alpha 8 | NM_003638 | 6.97 |
| MPP7 | membrane protein, palmitoylated 7 (MAGUK p55 subfamily member 7) | | 6.96 |
| ANXA8L1\|ANXA8L2 | annexin A8-like 1 \| annexin A8 \| annexin A8-like 2 | | 6.96 |
| ACTA2 | actin, alpha 2, smooth muscle, aorta | NM_001141945 | 6.94 |
| ANKRD1 | ankyrin repeat domain 1 (cardiac muscle) | NM_014391 | 6.91 |
| CYP2C8\|CYP2C19 | cytochrome P450, family 2, subfamily C, polypeptide 8 \| cytochrome P450, family 2, subfamily C, polypeptide 19 | NM_000770 | 6.87 |
| PDLIM1 | PDZ and LIM domain 1 | NM_020992 | 6.85 |
| KIAA1598 | | NM_001127211 | 6.85 |
| C11orf35\|LOC692247 | chromosome 11 open reading frame 35 \| hypothetical locus LOC692247 | | 6.73 |
| IGF2\|INS-IGF2 | insulin-like growth factor 2 (somatomedin A) \| INS-IGF2 readthrough transcript | NM_000612 | 6.69 |
| SNORA3 | small nucleolar RNA, H/ACA box 3 | | 6.66 |
| SNORA23 | small nucleolar RNA, H/ACA box 23 | | 6.61 |
| PDE3B | phosphodiesterase 3B, cGMP-inhibited | NM_000922 | 6.58 |
| NAV2 | neuron navigator 2 | NM_182964 | 6.53 |
| TSPAN18 | tetraspanin 18 | | 6.50 |
| CREB3L1 | cAMP responsive element binding protein 3-like 1 | NM_052854 | 6.49 |
| PTPRJ | protein tyrosine phosphatase, receptor type, J | NM_002843 | 6.48 |
| STX3 | syntaxin 3 | NM_004177 | 6.46 |
| C11orf9 | chromosome 11 open reading frame 9 | NM_001127392 | 6.45 |
| CST6 | cystatin E/M | NM_001323 | 6.45 |
| P2RY2 | purinergic receptor P2Y, G-protein coupled, 2 | NM_176072 | 6.42 |
| P2RY6 | pyrimidinergic receptor P2Y, G-protein coupled, 6 | NM_176796 | 6.39 |
| PIWIL4 | piwi-like 4 (Drosophila) | NM_152431 | 6.38 |
| ST14 | suppression of tumorigenicity 14 (colon carcinoma) | NM_021978 | 6.36 |
| ANO9 | anoctamin 9 | NM_001012302 | 6.36 |
| SOX6 | SRY (sex determining region Y)-box 6 | NM_017508 | 6.34 |
| PLEKHA7 | pleckstrin homology domain containing, family A member 7 | NM_175058 | 6.30 |
| SLC5A12 | solute carrier family 5 (sodium/glucose cotransporter), member 12 | NM_178498 | 6.26 |
| RCOR2 | REST corepressor 2 | NM_173587 | 6.25 |
| SHANK2 | SH3 and multiple ankyrin repeat domains 2 | NM_012309 | 6.23 |
| EXPH5 | exophilin 5 | NM_015065 | 6.20 |
| DRD2 | dopamine receptor D2 | NM_000795 | 6.14 |
| FXYD6 | FXYD domain containing ion transport regulator 6 | NM_001164836 | 6.13 |
| USP2 | ubiquitin specific peptidase 2 | NM_004205 | 6.09 |

FIG. 20 (3)

| genesymbol | genedescription | Accession number | Fold Change |
|---|---|---|---|
| CACNA1C | calcium channel, voltage-dependent, L type, alpha 1C subunit | NM_199460 | 6.03 |
| CCND2 | cyclin D2 | NM_001759 | 6.03 |
| SCARNA10 | small Cajal body-specific RNA 10 | | 6.02 |
| PIK3C2G | phosphoinositide-3-kinase, class 2, gamma polypeptide | NM_004570 | 5.94 |
| METTL7A | methyltransferase like 7A | NM_014033 | 5.93 |
| ERBB3 | v-erb-b2 erythroblastic leukemia viral oncogene homolog 3 (avian) | NM_001982 | 5.93 |
| HMGA2 | high mobility group AT-hook 2 | NM_003483 | 5.93 |
| RAB3IP | RAB3A interacting protein (rabin3) | NM_175623 | 5.90 |
| MIR492\|KRT19P2 | microRNA 492 \| keratin 19 pseudogene 2 | NM_002276 | 5.87 |
| SLC2A3 | solute carrier family 2 (facilitated glucose transporter), member 3 | NM_006931 | 5.86 |
| CLEC1B | C-type lectin domain family 1, member B | NM_016509 | 5.82 |
| DUSP16 | dual specificity phosphatase 16 | NM_030640 | 5.80 |
| SOX5 | SRY (sex determining region Y)-box 5 | NM_152989 | 5.79 |
| FAM60A | family with sequence similarity 60, member A | | 5.78 |
| PRICKLE1 | prickle homolog 1 (Drosophila) | NM_153026 | 5.78 |
| ADAMTS20 | ADAM metallopeptidase with thrombospondin type 1 motif, 20 | NM_025003 | 5.73 |
| GALNT6 | UDP-N-acetyl-alpha-D-galactosamine:polypeptide N-acetylgalactosaminyltransferase 6 (GalNAc-T6) | NM_007210 | 5.71 |
| KRT8 | keratin 8 | NM_002273 | 5.71 |
| TAC3 | tachykinin 3 | NR_033654 | 5.71 |
| LUM | lumican | NM_002345 | 5.66 |
| NUAK1 | NUAK family, SNF1-like kinase, 1 | NM_014840 | 5.65 |
| RNU4-1 | RNA, U4 small nuclear 1 | | 5.65 |
| SGCG | sarcoglycan, gamma (35kDa dystrophin-associated glycoprotein) | NM_000231 | 5.64 |
| C13orf15 | chromosome 13 open reading frame 15 | NM_014059 | 5.62 |
| MIR622\|KRT18 | microRNA 622 \| keratin 18 | NM_000224 | 5.61 |
| MIR17HG\|MIR19A\|MIR19B1\|MIR20A\|MIR92A1\|MIR18A | MIR17 host gene (non-protein coding) \| microRNA 17 \| microRNA 19a \| microRNA 19b-1 \| microRNA 20a \| microRNA 92a-1 \| microRNA 18a | | 5.59 |
| GPC6 | glypican 6 | | 5.56 |
| FLT1 | fms-related tyrosine kinase 1 (vascular endothelial growth factor/vascular permeability factor receptor) | NM_002019 | 5.55 |
| SLC7A1 | solute carrier family 7 (cationic amino acid transporter, y+ system), member 1 | NM_003045 | 5.54 |
| PCDH9 | protocadherin 9 | NM_203487 | 5.54 |
| POTEM\|POTEG\|POTEE\|POTEF\|POTEH | POTE ankyrin domain family, member M \| POTE ankyrin domain family, member G \| POTE ankyrin domain family, member E \| POTE ankyrin domain family, member F \| POTE ankyrin domain family, member H | | 5.52 |
| SLC39A2 | solute carrier family 39 (zinc transporter), member 2 | NM_014579 | 5.52 |
| DACT1 | dapper, antagonist of beta-catenin, homolog 1 (Xenopus laevis) | NM_016651 | 5.52 |
| AKAP5 | A kinase (PRKA) anchor protein 5 | NM_004857 | 5.50 |
| DIO3 | deiodinase, iodothyronine, type III | NM_001362 | 5.43 |

FIG. 20 (4)

| genesymbol | genedescription | Accession number | Fold Change |
|---|---|---|---|
| POTEG\|POTEM\|POTEH | POTE ankyrin domain family, member G \| POTE ankyrin domain family, member M \| POTE ankyrin domain family, member H | | 5.39 |
| RNASE1 | ribonuclease, RNase A family, 1 (pancreatic) | | 5.39 |
| NID2 | nidogen 2 (osteonidogen) | NM_007361 | 5.38 |
| RAB15 | | NM_198686 | 5.37 |
| TC2N | tandem C2 domains, nuclear | | 5.36 |
| CLMN | calmin (calponin-like, transmembrane) | | 5.36 |
| SNORD116-25 | small nucleolar RNA, C/D box 116-25 | | 5.34 |
| SNORD116-26 | small nucleolar RNA, C/D box 116-26 | | 5.32 |
| SNORD115-1\|SNORD115-13\|SNORD115-16\|SNORD115-12\|SNORD115-26\|SNORD115-40\|SNORD115-41\|SNORD115-5\|SNORD115-9\|SNRPN | small nucleolar RNA, C/D box 115-1 \| small nucleolar RNA, C/D box 115-13 \| small nucleolar RNA, C/D box 115-16 \| small nucleolar RNA, C/D box 115-12 \| small nucleolar RNA, C/D box 115-26 \| small nucleolar RNA, C/D box 115-40 \| small nucleolar RNA, C/D box 115-41 \| small nucleolar RNA, C/D box 115-5 \| small nucleolar RNA, C/D box 115-9 \| small nuclear ribonucleoprotein polypeptide N | AF400495 | 5.25 |
| SNORD115-12\|SNORD115-5\|SNORD115-9\|SNORD115-11\|SNORD115-29\|SNORD115-36\|SNORD115-43\|SNORD115-20\|SNORD115-17\|SNORD115-18\|SNORD115-19\|SNORD115-13\|SNORD115-25\|SNORD115-40\|SNORD115-42\|SNORD115-10\|SNORD115-14\|SNORD115-15\|SNORD115-24 | small nucleolar RNA, C/D box 115-12 \| small nucleolar RNA, C/D box 115-5 \| small nucleolar RNA, C/D box 115-9 \| small nucleolar RNA, C/D box 115-11 \| small nucleolar RNA, C/D box 115-29 \| small nucleolar RNA, C/D box 115-36 \| small nucleolar RNA, C/D box 115-43 \| small nucleolar RNA, C/D box 115-20 \| small nucleolar RNA, C/D box 115-17 \| small nucleolar RNA, C/D box 115-18 \| small nucleolar RNA, C/D box 115-19 \| small nucleolar RNA, C/D box 115-1 \| small nucleolar RNA, C/D box 115-13 \| small nucleolar RNA, C/D box 115-25 \| small nucleolar RNA, C/D box 115-40 \| small nucleolar RNA, C/D box 115-4 \| small nucleolar RNA, C/D box 115-42 \| small nucleolar RNA, C/D box 115-10 \| small nucleolar RNA, C/D box 115-14 \| small nucleolar RNA, C/D box 115-15 \| small nucleolar RNA, C/D box 115-24 | | 5.25 |

FIG. 20 (5)

| genesymbol | genedescription | Accession number | Fold Change |
|---|---|---|---|
| SNORD115-12\|SNORD115-5\|SNORD115-9\|SNORD115-11\|SNORD115-29\|SNORD115-36\|SNORD115-43\|SNORD115-22\|SNORD115-20\|SNORD115-39\|SNORD115-17\|SNORD115-18\|SNORD115-19\|SNORD115-13\|SNORD115-16\|SNORD115-25\|SNORD115-40\|SNORD115-44\|SNORD115-34\|SNORD115-42\|SNORD115-6\|SNORD115-10\|SNORD115-14\|SNORD115-15\|SNORD115-21\|SNORD115-24 | small nucleolar RNA, C/D box 115-12 \| small nucleolar RNA, C/D box 115-5 \| small nucleolar RNA, C/D box 115-9 \| small nucleolar RNA, C/D box 115-11 \| small nucleolar RNA, C/D box 115-29 \| small nucleolar RNA, C/D box 115-36 \| small nucleolar RNA, C/D box 115-43 \| small nucleolar RNA, C/D box 115-22 \| small nucleolar RNA, C/D box 115-20 \| small nucleolar RNA, C/D box 115-39 \| small nucleolar RNA, C/D box 115-17 \| small nucleolar RNA, C/D box 115-18 \| small nucleolar RNA, C/D box 115-19 \| small nucleolar RNA, C/D box 115-3 \| small nucleolar RNA, C/D box 115-1 \| small nucleolar RNA, C/D box 115-13 \| small nucleolar RNA, C/D box 115-16 \| small nucleolar RNA, C/D box 115-25 \| small nucleolar RNA, C/D box 115-40 \| small nucleolar RNA, C/D box 115-44 \| small nucleolar RNA, C/D box 115-34 \| small nucleolar RNA, C/D box 115-4 \| small nucleolar RNA, C/D box 115-42 \| small nucleolar RNA, C/D box 115-6 \| small nucleolar RNA, C/D box 115-10 \| small nucleolar RNA, C/D box 115-14 \| small nucleolar RNA, C/D box 115-15 \| small nucleolar RNA, C/D box 115-21 \| small nucleolar RNA, C/D box 115-24 | | 5.24 |
| SNORD115-11\|SNORD115-12\|SNORD115-29\|SNORD115-36\|SNORD115-43\|SNORD115-5\|SNORD115-9\|SNORD115-26\|SNORD115-22\|SNORD115-20\|SNORD115-39\|SNORD115-41\|SNORD115-17\|SNORD115-18\|SNORD115-19\|SNORD115-13\|SNORD115-16\|SNORD115-40\|SNORD115-44\|SNORD115-10\|SNORD115-14\|SNORD115-34\|SNORD115-42\|SNORD115-6\|SNORD115-24 | small nucleolar RNA, C/D box 115-11 \| small nucleolar RNA, C/D box 115-12 \| small nucleolar RNA, C/D box 115-29 \| small nucleolar RNA, C/D box 115-36 \| small nucleolar RNA, C/D box 115-43 \| small nucleolar RNA, C/D box 115-5 \| small nucleolar RNA, C/D box 115-9 \| small nucleolar RNA, C/D box 115-26 \| small nucleolar RNA, C/D box 115-22 \| small nucleolar RNA, C/D box 115-20 \| small nucleolar RNA, C/D box 115-39 \| small nucleolar RNA, C/D box 115-3 \| small nucleolar RNA, C/D box 115-41 \| small nucleolar RNA, C/D box 115-17 \| small nucleolar RNA, C/D box 115-18 \| small nucleolar RNA, C/D box 115-19 \| small nucleolar RNA, C/D box 115-1 \| small nucleolar RNA, C/D box 115-13 \| small nucleolar RNA, C/D box 115-16 \| small nucleolar RNA, C/D box 115-40 \| small nucleolar RNA, C/D box 115-44 \| small nucleolar RNA, C/D box 115-10 \| small nucleolar RNA, C/D box 115-14 \| small nucleolar RNA, C/D box 115-34 \| small nucleolar RNA, C/D box 115-4 \| small nucleolar RNA, C/D box 115-42 \| small nucleolar RNA, C/D box 115-6 \| small nucleolar RNA, C/D box 115-24 | | 5.23 |

FIG. 20 (6)

| genesymbol | genedescription | Accession number | Fold Change |
|---|---|---|---|
| SNORD115-12\|SNORD115-5\|SNORD115-9\|SNORD115-11\|SNORD115-29\|SNORD115-36\|SNORD115-43\|SNORD115-22\|SNORD115-20\|SNORD115-39\|SNORD115-17\|SNORD115-18\|SNORD115-19\|SNORD115-13\|SNORD115-16\|SNORD115-25\|SNORD115-40\|SNORD115-44\|SNORD115-34\|SNORD115-42\|SNORD115-6\|SNORD115-10\|SNORD115-14\|SNORD115-15\|SNORD115-21\|SNORD115-24 | small nucleolar RNA, C/D box 115-12 \| small nucleolar RNA, C/D box 115-5 \| small nucleolar RNA, C/D box 115-9 \| small nucleolar RNA, C/D box 115-11 \| small nucleolar RNA, C/D box 115-29 \| small nucleolar RNA, C/D box 115-36 \| small nucleolar RNA, C/D box 115-43 \| small nucleolar RNA, C/D box 115-22 \| small nucleolar RNA, C/D box 115-20 \| small nucleolar RNA, C/D box 115-39 \| small nucleolar RNA, C/D box 115-17 \| small nucleolar RNA, C/D box 115-18 \| small nucleolar RNA, C/D box 115-19 \| small nucleolar RNA, C/D box 115-3 \| small nucleolar RNA, C/D box 115-1 \| small nucleolar RNA, C/D box 115-13 \| small nucleolar RNA, C/D box 115-16 \| small nucleolar RNA, C/D box 115-25 \| small nucleolar RNA, C/D box 115-40 \| small nucleolar RNA, C/D box 115-44 \| small nucleolar RNA, C/D box 115-34 \| small nucleolar RNA, C/D box 115-4 \| small nucleolar RNA, C/D box 115-42 \| small nucleolar RNA, C/D box 115-6 \| small nucleolar RNA, C/D box 115-10 \| small nucleolar RNA, C/D box 115-14 \| small nucleolar RNA, C/D box 115-15 \| small nucleolar RNA, C/D box 115-21 \| small nucleolar RNA, C/D box 115-24 | | 5.21 |
| SNORD115-1\|SNORD115-13\|SNORD115-16\|SNORD115-12\|SNORD115-40\|SNORD115-5\|SNORD115-9\|SNORD115-10\|SNORD115-14\|SNORD115-21\|SNORD115-42\|SNRPN | small nucleolar RNA, C/D box 115-1 \| small nucleolar RNA, C/D box 115-13 \| small nucleolar RNA, C/D box 115-16 \| small nucleolar RNA, C/D box 115-12 \| small nucleolar RNA, C/D box 115-40 \| small nucleolar RNA, C/D box 115-5 \| small nucleolar RNA, C/D box 115-9 \| small nucleolar RNA, C/D box 115-10 \| small nucleolar RNA, C/D box 115-14 \| small nucleolar RNA, C/D box 115-21 \| small nucleolar RNA, C/D box 115-4 \| small nucleolar RNA, C/D box 115-42 \| small nuclear ribonucleoprotein polypeptide N | AF400495 | 5.20 |
| SNORD115-1\|SNORD115-13\|SNORD115-16\|SNORD115-11\|SNORD115-26\|SNORD115-29\|SNORD115-36\|SNORD115-39\|SNORD115-40\|SNORD115-41\|SNORD115-43\|SNORD115-34\|SNORD115-6\|SNRPN | small nucleolar RNA, C/D box 115-1 \| small nucleolar RNA, C/D box 115-13 \| small nucleolar RNA, C/D box 115-16 \| small nucleolar RNA, C/D box 115-11 \| small nucleolar RNA, C/D box 115-26 \| small nucleolar RNA, C/D box 115-29 \| small nucleolar RNA, C/D box 115-36 \| small nucleolar RNA, C/D box 115-39 \| small nucleolar RNA, C/D box 115-40 \| small nucleolar RNA, C/D box 115-41 \| small nucleolar RNA, C/D box 115-43 \| small nucleolar RNA, C/D box 115-34 \| small nucleolar RNA, C/D box 115-6 \| small nuclear ribonucleoprotein polypeptide N | AF400495 | 5.15 |

FIG. 20 (7)

| genesymbol | genedescription | Accession number | Fold Change |
|---|---|---|---|
| SNORD115-11\|SNORD115-22\|SNORD115-29\|SNORD115-36\|SNORD115-43\|SNORD115-26\|SNORD115-39\|SNORD115-41\|SNORD115-16\|SNORD115-44\|SNORD115-34\|SNORD115-6\|SNORD115-7 | small nucleolar RNA, C/D box 115-11 \| small nucleolar RNA, C/D box 115-22 \| small nucleolar RNA, C/D box 115-29 \| small nucleolar RNA, C/D box 115-36 \| small nucleolar RNA, C/D box 115-43 \| small nucleolar RNA, C/D box 115-26 \| small nucleolar RNA, C/D box 115-39 \| small nucleolar RNA, C/D box 115-41 \| small nucleolar RNA, C/D box 115-16 \| small nucleolar RNA, C/D box 115-44 \| small nucleolar RNA, C/D box 115-34 \| small nucleolar RNA, C/D box 115-6 \| small nucleolar RNA, C/D box 115-7 | | 5.13 |
| SNORD115-26\|SNORD115-11\|SNORD115-12\|SNORD115-29\|SNORD115-36\|SNORD115-43\|SNORD115-5\|SNORD115-9\|SNORD115-22\|SNORD115-39\|SNORD115-41\|SNORD115-16\|SNORD115-44\|SNORD115-24\|SNRPN | small nucleolar RNA, C/D box 115-26 \| small nucleolar RNA, C/D box 115-11 \| small nucleolar RNA, C/D box 115-12 \| small nucleolar RNA, C/D box 115-29 \| small nucleolar RNA, C/D box 115-36 \| small nucleolar RNA, C/D box 115-43 \| small nucleolar RNA, C/D box 115-5 \| small nucleolar RNA, C/D box 115-9 \| small nucleolar RNA, C/D box 115-22 \| small nucleolar RNA, C/D box 115-39 \| small nucleolar RNA, C/D box 115-41 \| small nucleolar RNA, C/D box 115-3 \| small nucleolar RNA, C/D box 115-16 \| small nucleolar RNA, C/D box 115-44 \| small nucleolar RNA, C/D box 115-24 \| small nuclear ribonucleoprotein polypeptide N | AF400501 | 5.12 |
| SNORD115-11\|SNORD115-12\|SNORD115-29\|SNORD115-36\|SNORD115-43\|SNORD115-5\|SNORD115-9\|SNORD115-26\|SNORD115-22\|SNORD115-20\|SNORD115-39\|SNORD115-41\|SNORD115-17\|SNORD115-18\|SNORD115-19\|SNORD115-13\|SNORD115-16\|SNORD115-40\|SNORD115-44\|SNORD115-10\|SNORD115-14\|SNORD115-34\|SNORD115-42\|SNORD115-6\|SNORD115-24 | small nucleolar RNA, C/D box 115-11 \| small nucleolar RNA, C/D box 115-12 \| small nucleolar RNA, C/D box 115-29 \| small nucleolar RNA, C/D box 115-36 \| small nucleolar RNA, C/D box 115-43 \| small nucleolar RNA, C/D box 115-5 \| small nucleolar RNA, C/D box 115-9 \| small nucleolar RNA, C/D box 115-26 \| small nucleolar RNA, C/D box 115-22 \| small nucleolar RNA, C/D box 115-20 \| small nucleolar RNA, C/D box 115-39 \| small nucleolar RNA, C/D box 115-3 \| small nucleolar RNA, C/D box 115-41 \| small nucleolar RNA, C/D box 115-17 \| small nucleolar RNA, C/D box 115-18 \| small nucleolar RNA, C/D box 115-19 \| small nucleolar RNA, C/D box 115-1 \| small nucleolar RNA, C/D box 115-13 \| small nucleolar RNA, C/D box 115-16 \| small nucleolar RNA, C/D box 115-40 \| small nucleolar RNA, C/D box 115-44 \| small nucleolar RNA, C/D box 115-10 \| small nucleolar RNA, C/D box 115-14 \| small nucleolar RNA, C/D box 115-34 \| small nucleolar RNA, C/D box 115-4 \| small nucleolar RNA, C/D box 115-42 \| small nucleolar RNA, C/D box 115-6 \| small nucleolar RNA, C/D box 115-24 | | 5.12 |

FIG. 20 (8)

| genesymbol | genedescription | Accession number | Fold Change |
|---|---|---|---|
| SNORD115-11\|SNORD115-12\|SNORD115-29\|SNORD115-36\|SNORD115-43\|SNORD115-5\|SNORD115-9\|SNORD115-26\|SNORD115-22\|SNORD115-20\|SNORD115-39\|SNORD115-41\|SNORD115-17\|SNORD115-18\|SNORD115-19\|SNORD115-13\|SNORD115-16\|SNORD115-40\|SNORD115-44\|SNORD115-10\|SNORD115-14\|SNORD115-34\|SNORD115-42\|SNORD115-6\|SNORD115-24 | small nucleolar RNA, C/D box 115-11 \| small nucleolar RNA, C/D box 115-12 \| small nucleolar RNA, C/D box 115-29 \| small nucleolar RNA, C/D box 115-36 \| small nucleolar RNA, C/D box 115-43 \| small nucleolar RNA, C/D box 115-5 \| small nucleolar RNA, C/D box 115-9 \| small nucleolar RNA, C/D box 115-26 \| small nucleolar RNA, C/D box 115-22 \| small nucleolar RNA, C/D box 115-20 \| small nucleolar RNA, C/D box 115-39 \| small nucleolar RNA, C/D box 115-3 \| small nucleolar RNA, C/D box 115-41 \| small nucleolar RNA, C/D box 115-17 \| small nucleolar RNA, C/D box 115-18 \| small nucleolar RNA, C/D box 115-19 \| small nucleolar RNA, C/D box 115-1 \| small nucleolar RNA, C/D box 115-13 \| small nucleolar RNA, C/D box 115-16 \| small nucleolar RNA, C/D box 115-40 \| small nucleolar RNA, C/D box 115-44 \| small nucleolar RNA, C/D box 115-10 \| small nucleolar RNA, C/D box 115-14 \| small nucleolar RNA, C/D box 115-34 \| small nucleolar RNA, C/D box 115-4 \| small nucleolar RNA, C/D box 115-42 \| small nucleolar RNA, C/D box 115-6 \| small nucleolar RNA, C/D box 115-24 | | 5.12 |
| SNORD115-11\|SNORD115-26\|SNORD115-29\|SNORD115-36\|SNORD115-39\|SNORD115-43\|SNORD115-41\|SNORD115-22\|SNORD115-16\|SNORD115-14\|SNORD115-38\|SNORD115-44 | small nucleolar RNA, C/D box 115-11 \| small nucleolar RNA, C/D box 115-26 \| small nucleolar RNA, C/D box 115-29 \| small nucleolar RNA, C/D box 115-36 \| small nucleolar RNA, C/D box 115-39 \| small nucleolar RNA, C/D box 115-43 \| small nucleolar RNA, C/D box 115-41 \| small nucleolar.RNA, C/D box 115-22 \| small nucleolar RNA, C/D box 115-16 \| small nucleolar RNA, C/D box 115-14 \| small nucleolar RNA, C/D box 115-38 \| small nucleolar RNA, C/D box 115-44 \| small nucleolar RNA, C/D box 115-3 | | 5.08 |
| SNORD115-42\|SNORD115-6\|SNORD115-30\|SNORD115-34\|SNORD115-15\|SNORD115-21\|SNORD115-12\|SNORD115-13\|SNORD115-40\|SNORD115-5\|SNORD115-9\|SNORD115-10\|SNORD115-14\|SNORD115-24 | small nucleolar RNA, C/D box 115-42 \| small nucleolar RNA, C/D box 115-6 \| small nucleolar RNA, C/D box 115-4 \| small nucleolar RNA, C/D box 115-30 \| small nucleolar RNA, C/D box 115-34 \| small nucleolar RNA, C/D box 115-15 \| small nucleolar RNA, C/D box 115-21 \| small nucleolar RNA, C/D box 115-12 \| small nucleolar RNA, C/D box 115-13 \| small nucleolar RNA, C/D box 115-40 \| small nucleolar RNA, C/D box 115-5 \| small nucleolar RNA, C/D box 115-9 \| small nucleolar RNA, C/D box 115-10 \| small nucleolar RNA, C/D box 115-14 \| small nucleolar RNA, C/D box 115-24 | | 5.06 |

FIG. 20 (9)

| genesymbol | genedescription | Accession number | Fold Change |
|---|---|---|---|
| SNORD115-11\|SNORD115-12\|SNORD115-29\|SNORD115-36\|SNORD115-43\|SNORD115-5\|SNORD115-9\|SNORD115-26\|SNORD115-22\|SNORD115-20\|SNORD115-39\|SNORD115-41\|SNORD115-17\|SNORD115-18\|SNORD115-19\|SNORD115-13\|SNORD115-16\|SNORD115-40\|SNORD115-44\|SNORD115-34\|SNORD115-6\|SNORD115-10\|SNORD115-24 | small nucleolar RNA, C/D box 115-11 \| small nucleolar RNA, C/D box 115-12 \| small nucleolar RNA, C/D box 115-29 \| small nucleolar RNA, C/D box 115-36 \| small nucleolar RNA, C/D box 115-43 \| small nucleolar RNA, C/D box 115-5 \| small nucleolar RNA, C/D box 115-9 \| small nucleolar RNA, C/D box 115-26 \| small nucleolar RNA, C/D box 115-22 \| small nucleolar RNA, C/D box 115-20 \| small nucleolar RNA, C/D box 115-39 \| small nucleolar RNA, C/D box 115-3 \| small nucleolar RNA, C/D box 115-41 \| small nucleolar RNA, C/D box 115-17 \| small nucleolar RNA, C/D box 115-18 \| small nucleolar RNA, C/D box 115-19 \| small nucleolar RNA, C/D box 115-1 \| small nucleolar RNA, C/D box 115-13 \| small nucleolar RNA, C/D box 115-16 \| small nucleolar RNA, C/D box 115-40 \| small nucleolar RNA, C/D box 115-44 \| small nucleolar RNA, C/D box 115-34 \| small nucleolar RNA, C/D box 115-6 \| small nucleolar RNA, C/D box 115-10 \| small nucleolar RNA, C/D box 115-24 | | 5.05 |
| C15orf41 | chromosome 15 open reading frame 41 | | 5.03 |
| PAK6 | p21 protein (Cdc42/Rac)-activated kinase 6 | NM_020168 | 5.03 |
| SPINT1 | serine peptidase inhibitor, Kunitz type 1 | NM_181642 | 5.01 |
| CKMT1A\|CKMT1B | creatine kinase, mitochondrial 1A \| creatine kinase, mitochondrial 1B | NM_001015001 | 5.00 |
| CKMT1A\|CKMT1B | creatine kinase, mitochondrial 1A \| creatine kinase, mitochondrial 1B | NM_001015001 | 5.00 |
| SLC27A2 | solute carrier family 27 (fatty acid transporter), member 2 | NM_003645 | 4.99 |
| TLN2 | talin 2 | NM_015059 | 4.98 |
| TPM1 | tropomyosin 1 (alpha) | NM_000366 | 4.97 |
| NR2F2 | nuclear receptor subfamily 2, group F, member 2 | NM_021005 | 4.96 |
| Tr. 7987403 | | | 4.95 |
| RASGRP1 | RAS guanyl releasing protein 1 (calcium and DAG-regulated) | NM_005739 | 4.94 |
| GATM | glycine amidinotransferase (L-arginine:glycine amidinotransferase) | NM_001482 | 4.93 |
| CYP19A1 | cytochrome P450, family 19, subfamily A, polypeptide 1 | NM_031226 | 4.93 |
| MYO5C | myosin VC | | 4.93 |
| RBPMS2 | RNA binding protein with multiple splicing 2 | | 4.92 |
| GRAMD2 | GRAM domain containing 2 | | 4.92 |
| ATF7IP2 | activating transcription factor 7 interacting protein 2 | NM_024997 | 4.91 |
| ACSM3\|ERI2 | acyl-CoA synthetase medium-chain family member 3 \| ERI1 exoribonuclease family member 2 | NM_005622 | 4.90 |
| QPRT | quinolinate phosphoribosyltransferase | NM_014298 | 4.88 |
| LPCAT2 | lysophosphatidylcholine acyltransferase 2 | NM_017839 | 4.86 |
| GPR56 | G protein-coupled receptor 56 | NM_201524 | 4.86 |
| MMP15 | matrix metallopeptidase 15 (membrane-inserted) | NM_002428 | 4.83 |
| MARVELD3 | MARVEL domain containing 3 | | 4.82 |
| PPL | periplakin | NM_002705 | 4.82 |

FIG. 20 (10)

| genesymbol | genedescription | Accession number | Fold Change |
|---|---|---|---|
| GPRC5B | G protein-coupled receptor, family C, group 5, member B | | 4.79 |
| Tr. 8000480 | | | 4.78 |
| CDH8 | cadherin 8, type 2 | NM_001796 | 4.77 |
| ESRP2 | epithelial splicing regulatory protein 2 | NM_024939 | 4.75 |
| SLC7A5 | solute carrier family 7 (cationic amino acid transporter, y+ system), member 5 | NM_003486 | 4.75 |
| TMEM88 | transmembrane protein 88 | | 4.71 |
| RAB11FIP4 | RAB11 family interacting protein 4 (class II) | NM_032932 | 4.70 |
| MYL4 | myosin, light chain 4, alkali; atrial, embryonic | NM_001002841 | 4.70 |
| TBX4 | T-box 4 | NM_018488 | 4.69 |
| TANC2 | tetratricopeptide repeat, ankyrin repeat and coiled-coil containing 2 | | 4.69 |
| LLGL2 | lethal giant larvae homolog 2 (Drosophila) | NM_001031803 | 4.68 |
| ITGB4 | integrin, beta 4 | NM_000213 | 4.68 |
| NXN | nucleoredoxin | NM_022463 | 4.67 |
| LOC100130876 | | | 4.67 |
| SLC6A4 | solute carrier family 6 (neurotransmitter transporter, serotonin), member 4 | NM_001045 | 4.66 |
| SLFN13 | schlafen family member 13 | | 4.66 |
| KRT23 | keratin 23 (histone deacetylase inducible) | | 4.66 |
| KRT19 | keratin 19 | NM_002276 | 4.66 |
| WNT3 | wingless-type MMTV integration site family, member 3 | NM_030753 | 4.62 |
| HOXB2 | homeobox B2 | NM_002145 | 4.62 |
| HOXB3 | homeobox B3 | NM_002146 | 4.58 |
| RNF43 | ring finger protein 43 | | 4.57 |
| SLC16A6 | solute carrier family 16, member 6 (monocarboxylic acid transporter 7) | NM_001174166 | 4.57 |
| C17orf28 | chromosome 17 open reading frame 28 | | 4.57 |
| ZNF750 | zinc finger protein 750 | | 4.56 |
| ARHGAP28 | Rho GTPase activating protein 28 | NM_001010000 | 4.55 |
| DSG2 | desmoglein 2 | NM_001943 | 4.55 |
| TTR | transthyretin | NM_000371 | 4.54 |
| ASXL3 | additional sex combs like 3 (Drosophila) | NM_030632 | 4.54 |
| EPB41L3 | erythrocyte membrane protein band 4.1-like 3 | NM_012307 | 4.53 |
| LAMA1 | laminin, alpha 1 | NM_005559 | 4.53 |
| PSTPIP2 | proline-serine-threonine phosphatase interacting protein 2 | | 4.52 |
| MYO5B | myosin VB | NM_001080467 | 4.52 |
| ATP8B1 | ATPase, aminophospholipid transporter, class I, type 8B, member 1 | NM_005603 | 4.52 |
| ALPK2 | alpha-kinase 2 | NM_052947 | 4.52 |
| CCBE1 | collagen and calcium binding EGF domains 1 | NM_133459 | 4.51 |
| CYB5A | cytochrome b5 type A (microsomal) | NM_148923 | 4.51 |
| ARID3A | AT rich interactive domain 3A (BRIGHT-like) | NM_005224 | 4.50 |
| KIAA1543 | | NM_001080429 | 4.50 |
| ZNF93 | zinc finger protein 93 | NM_031218 | 4.48 |
| ZNF90|ZNF93 | zinc finger protein 90 | zinc finger protein 93 | NM_007138 | 4.48 |
| ZNF714 | zinc finger protein 714 | NM_182515 | 4.47 |

FIG. 20 (11)

| genesymbol | genedescription | Accession number | Fold Change |
|---|---|---|---|
| ZNF738 | zinc finger protein 738 | NR_027130 | 4.47 |
| RPSAP58 | ribosomal protein SA pseudogene 58 | | 4.47 |
| LSR | lipolysis stimulated lipoprotein receptor | NM_205834 | 4.45 |
| SPINT2 | serine peptidase inhibitor, Kunitz type, 2. | NM_021102 | 4.44 |
| CGB5\|CGB8\|CGB7\|CGB1 | chorionic gonadotropin, beta polypeptide 5 \| chorionic gonadotropin, beta polypeptide 8 \| chorionic gonadotropin, beta polypeptide 7 \| chorionic gonadotropin, beta polypeptide 1 | NM_000737 | 4.42 |
| FLJ45949 | | | 4.40 |
| FBN3 | fibrillin 3 | | 4.40 |
| RGL3 | ral guanine nucleotide dissociation stimulator-like 3 | NM_001161616 | 4.38 |
| NOTCH3 | notch 3 | NM_000435 | 4.35 |
| EPHX3 | epoxide hydrolase 3 | NM_024794 | 4.35 |
| ISYNA1 | inositol-3-phosphate synthase 1 | NM_016368 | 4.34 |
| RHPN2 | rhophilin, Rho GTPase binding protein 2 | NM_033103 | 4.33 |
| DMKN | dermokine | | 4.31 |
| CGB\|CGB5\|CGB8\|CGB7\|CGB2 | chorionic gonadotropin, beta polypeptide \| chorionic gonadotropin, beta polypeptide 5 \| chorionic gonadotropin, beta polypeptide 8 \| chorionic gonadotropin, beta polypeptide 7 \| chorionic gonadotropin, beta polypeptide 2 | NM_000737 | 4.29 |
| CGB1\|CGB5\|CGB8\|CGB2 | chorionic gonadotropin, beta polypeptide 1 \| chorionic gonadotropin, beta polypeptide 5 \| chorionic gonadotropin, beta polypeptide 8 \| chorionic gonadotropin, beta polypeptide 2 | BC106059 | 4.28 |
| CGB5\|CGB8\|CGB7 | chorionic gonadotropin, beta polypeptide 5 \| chorionic gonadotropin, beta polypeptide 8 \| chorionic gonadotropin, beta polypeptide 7 | NM_000737 | 4.28 |
| CGB7\|CGB5\|CGB2\|CGB8\|NTF4 | chorionic gonadotropin, beta polypeptide 7 \| chorionic gonadotropin, beta polypeptide 5 \| chorionic gonadotropin, beta polypeptide 2 \| chorionic gonadotropin, beta polypeptide 8 \| neurotrophin 4 | NM_000737 | 4.27 |
| ZNF702P | zinc finger protein 702, pseudogene | NR_003578 | 4.26 |
| MYCN | v-myc myelocytomatosis viral related oncogene, neuroblastoma derived (avian) | NM_005378 | 4.26 |
| PKDCC | protein kinase domain containing, cytoplasmic homolog (mouse) | NM_138370 | 4.26 |
| C2orf15\|MRPL30 | chromosome 2 open reading frame 15 \| mitochondrial ribosomal protein L30 | AK126402 | 4.25 |
| IL1R1 | interleukin 1 receptor, type I | NM_000877 | 4.25 |
| EPB41L5 | erythrocyte membrane protein band 4.1 like 5 | NM_020909 | 4.24 |
| C2orf14\|LOC440905\|LOC100128270 | chromosome 2 open reading frame 14 \| hypothetical LOC440905 \| Uncharacterized protein C2orf14-like 2 | | 4.24 |
| ACVR2A | activin A receptor, type IIA | NM_001616 | 4.24 |
| LYPD6 | LY6/PLAUR domain containing 6 | | 4.23 |
| GCA | grancalcin, EF-hand calcium binding protein | NM_012198 | 4.22 |
| CDCA7 | cell division cycle associated 7 | NM_031942 | 4.21 |
| FSIP2 | fibrous sheath interacting protein 2 | | 4.21 |
| FSIP2 | fibrous sheath interacting protein 2 | | 4.21 |
| COL3A1 | collagen, type III, alpha 1 | NM_000090 | 4.21 |
| SLC39A10 | solute carrier family 39 (zinc transporter), member 10 | NM_001127257 | 4.21 |
| CPS1 | carbamoyl-phosphate synthase 1, mitochondrial | NM_001875 | 4.20 |

FIG. 20 (12)

| genesymbol | genedescription | Accession number | Fold Change |
|---|---|---|---|
| CXCR7 | chemokine (C-X-C motif) receptor 7 | NM_020311 | 4.19 |
| FAM49A | family with sequence similarity 49, member A | | 4.17 |
| SLC8A1 | solute carrier family 8 (sodium/calcium exchanger), member 1 | NM_021097 | 4.16 |
| FSHR | follicle stimulating hormone receptor | NM_000145 | 4.15 |
| BCL11A | B-cell CLL/lymphoma 11A (zinc finger protein) | NM_022893 | 4.15 |
| PAIP2B | poly(A) binding protein interacting protein 2B | NM_020459 | 4.13 |
| AFF3 | AF4/FMR2 family, member 3 | NM_002285 | 4.12 |
| LOC440905 | | | 4.11 |
| C2orf14\|LOC440905\|LOC100128270 | chromosome 2 open reading frame 14 \| hypothetical LOC440905 \| Uncharacterized protein C2orf14-like 2 | | 4.10 |
| POTEE\|POTEF\|POTEH\|POTEM\|POTEG\|POTEB | POTE ankyrin domain family, member E \| POTE ankyrin domain family, member F \| POTE ankyrin domain family, member H \| POTE ankyrin domain family, member M \| POTE ankyrin domain family, member G \| POTE ankyrin domain family, member B | | 4.10 |
| FIGN | fidgetin | | 4.09 |
| COBLL1 | COBL-like 1 | | 4.09 |
| GALNT3 | UDP-N-acetyl-alpha-D-galactosamine:polypeptide N-acetylgalactosaminyltransferase 3 (GalNAc-T3) | NM_004482 | 4.09 |
| CHN1 | chimerin (chimaerin) 1 | NM_001822 | 4.09 |
| SLC19A3 | solute carrier family 19, member 3 | NM_025243 | 4.07 |
| KCNJ13 | potassium inwardly-rectifying channel, subfamily J, member 13 | NM_002242 | 4.06 |
| ARL4C | ADP-ribosylation factor-like 4C | NM_005737 | 4.06 |
| TGIF2 | TGFB-induced factor homeobox 2 | NM_021809 | 4.04 |
| WFDC2 | WAP four-disulfide core domain 2 | NM_006103 | 4.03 |
| TSHZ2 | teashirt zinc finger homeobox 2 | NM_173485 | 4.03 |
| TSHZ2 | teashirt zinc finger homeobox 2 | NM_173485 | 4.03 |
| TFAP2C | transcription factor AP-2 gamma (activating enhancer binding protein 2 gamma) | NM_003222 | 4.01 |
| FLRT3 | fibronectin leucine rich transmembrane protein 3 | NM_198391 | 4.01 |
| TGM2 | transglutaminase 2 (C polypeptide, protein-glutamine-gamma-glutamyltransferase) | NM_004613 | 4.00 |
| BMP7 | bone morphogenetic protein 7 | NM_001719 | 3.99 |
| HUNK | hormonally up-regulated Neu-associated kinase | NM_014586 | 3.99 |
| TIAM1 | T-cell lymphoma invasion and metastasis 1 | NM_003253 | 3.99 |
| CBS | cystathionine-beta-synthase | NM_001178008 | 3.98 |
| CECR2 | cat eye syndrome chromosome region, candidate 2 | NM_031413 | 3.97 |
| ADRBK2 | adrenergic, beta, receptor kinase 2 | NM_005160 | 3.97 |
| Tr. 8073680 | | | 3.95 |
| POTEM\|POTEH\|POTEG\|POTEE\|POTEF | POTE ankyrin domain family, member M \| POTE ankyrin domain family, member H \| POTE ankyrin domain family, member G \| POTE ankyrin domain family, member E \| POTE ankyrin domain family, member F | | 3.94 |
| Tr. 8075657 | | | 3.93 |
| C1QTNF6 | C1q and tumor necrosis factor related protein 6 | | 3.93 |
| LMCD1 | LIM and cysteine-rich domains 1 | NM_014583 | 3.92 |
| TRIM71 | tripartite motif-containing 71 | NM_001039111 | 3.91 |
| ACVR2B | activin A receptor, type IIB | NM_001106 | 3.91 |

FIG. 20 (13)

| genesymbol | genedescription | Accession number | Fold Change |
|---|---|---|---|
| NBEAL2 | neurobeachin-like 2 | | 3.90 |
| DOCK3 | dedicator of cytokinesis 3 | | 3.88 |
| ST3GAL6 | ST3 beta-galactoside alpha-2,3-sialyltransferase 6 | NM_006100 | 3.87 |
| UPK1B | uroplakin 1B | NM_006952 | 3.86 |
| SLC15A2 | solute carrier family 15 (H+/peptide transporter), member 2 | NM_021082 | 3.86 |
| MED12L | mediator complex subunit 12-like | NM_053002 | 3.85 |
| ARHGEF26 | Rho guanine nucleotide exchange factor (GEF) 26 | | 3.84 |
| NLGN1 | neuroligin 1 | NM_014932 | 3.84 |
| EPHB3 | EPH receptor B3 | NM_004443 | 3.83 |
| SATB1 | SATB homeobox 1 | NM_002971 | 3.83 |
| THRB | thyroid hormone receptor, beta (erythroblastic leukemia viral (v-erb-a) oncogene homolog 2, avian) | NM_001128176 | 3.83 |
| ADAMTS9 | ADAM metallopeptidase with thrombospondin type 1 motif, 9 | NM_182920 | 3.82 |
| VGLL3 | vestigial like 3 (Drosophila) | | 3.82 |
| FILIP1L | filamin A interacting protein 1-like | NM_182909 | 3.82 |
| IGSF10|MED12L | immunoglobulin superfamily, member 10 | mediator complex subunit 12-like | NM_178822 | 3.81 |
| SST | somatostatin | NM_001048 | 3.79 |
| D4S234E | DNA segment on chromosome 4 (unique) 234 expressed sequence | NM_014392 | 3.79 |
| CPZ|GPR78 | carboxypeptidase Z | G protein-coupled receptor 78 | NM_001014448 | 3.79 |
| SLIT2 | slit homolog 2 (Drosophila) | NM_004787 | 3.77 |
| C4orf19|RELL1 | chromosome 4 open reading frame 19 | RELT-like 1 | | 3.76 |
| NSUN7 | NOP2/Sun domain family, member 7 | | 3.76 |
| SHROOM3 | shroom family member 3 | NM_020859 | 3.75 |
| FRAS1 | Fraser syndrome 1 | NM_025074 | 3.74 |
| CDS1 | CDP-diacylglycerol synthase (phosphatidate cytidylyltransferase) 1 | NM_001263 | 3.74 |
| FAM190A | family with sequence similarity 190, member A | | 3.72 |
| DAPP1 | dual adaptor of phosphotyrosine and 3-phosphoinositides | NM_014395 | 3.71 |
| MAB21L2 | mab-21-like 2 (C. elegans) | NM_006439 | 3.71 |
| FHDC1 | FH2 domain containing 1 | NM_033393 | 3.71 |
| GUCY1B3 | guanylate cyclase 1, soluble, beta 3 | NM_000857 | 3.71 |
| CPE | carboxypeptidase E | NM_001873 | 3.70 |
| NBLA00301 | Nbla00301 | | 3.70 |
| LDB2 | LIM domain binding 2 | NM_001130834 | 3.69 |
| ARAP2 | ArfGAP with RhoGAP domain, ankyrin repeat and PH domain 2 | NM_015230 | 3.69 |
| RBM47 | RNA binding motif protein 47 | . | 3.69 |
| RASGEF1B | RasGEF domain family, member 1B | NM_152545 | 3.68 |
| MOP-1 | | | 3.68 |
| ABCG2 | ATP-binding cassette, sub-family G (WHITE), member 2 | NM_004827 | 3.67 |
| PRSS12 | protease, serine, 12 (neurotrypsin, motopsin) | NM_003619 | 3.66 |
| TMEM154 | transmembrane protein 154 | | 3.66 |
| FGA | fibrinogen alpha chain | NM_000508 | 3.66 |
| AADAT | aminoadipate aminotransferase | NM_016228 | 3.64 |
| HAND2 | heart and neural crest derivatives expressed 2 | NM_021973 | 3.64 |

FIG. 20 (14)

| genesymbol | genedescription | Accession number | Fold Change |
|---|---|---|---|
| MGC45800 | hypothetical LOC90768 | | 3.64 |
| TRIML2 | tripartite motif family-like 2 | | 3.63 |
| FAM105A | family with sequence similarity 105, member A | | 3.62 |
| SKP2 | S-phase kinase-associated protein 2 (p45) | NM_005983 | 3.62 |
| EGFLAM | EGF-like, fibronectin type III and laminin G domains | NM_152403 | 3.62 |
| MAP3K1 | mitogen-activated protein kinase kinase kinase 1 | NM_005921 | 3.61 |
| MARVELD2 | MARVEL domain containing 2 | NM_001038603 | 3.61 |
| IQGAP2 | IQ motif containing GTPase activating protein 2 | NM_006633 | 3.61 |
| CRHBP | corticotropin releasing hormone binding protein | NM_001882 | 3.59 |
| C5orf30 | chromosome 5 open reading frame 30 | | 3.58 |
| ADRA1B | adrenergic, alpha-1B-, receptor | NM_000679 | 3.57 |
| WWC1 | WW and C2 domain containing 1 | NM_001161661 | 3.56 |
| Tr. 8110668 | | | 3.56 |
| ELOVL7 | ELOVL family member 7, elongation of long chain fatty acids (yeast) | NM_024930 | 3.55 |
| ENC1 | ectodermal-neural cortex 1 (with BTB-like domain) | NM_003633 | 3.55 |
| FAM169A | family with sequence similarity 169, member A | | 3.54 |
| GCNT4 | glucosaminyl (N-acetyl) transferase 4, core 2 | NM_016591 | 3.54 |
| MEF2C | myocyte enhancer factor 2C | NM_002397 | 3.53 |
| EPB41L4A | erythrocyte membrane protein band 4.1 like 4A | NM_022140 | 3.52 |
| PPP2R2B | protein phosphatase 2, regulatory subunit B, beta | NM_004576 | 3.52 |
| SLIT3 | slit homolog 3 (Drosophila) | NM_003062 | 3.51 |
| SYCP2L|TMEM14B | synaptonemal complex protein 2-like | transmembrane protein 14B | | 3.49 |
| HIST1H3E | histone cluster 1, H3e | | 3.47 |
| HIST1H2BH | histone cluster 1, H2bh | NM_003524 | 3.47 |
| ANKS1A | ankyrin repeat and sterile alpha motif domain containing 1A | | 3.46 |
| SCUBE3 | signal peptide, CUB domain, EGF-like 3 | NM_152753 | 3.46 |
| SH3BGRL2 | SH3 domain binding glutamic acid-rich protein like 2 | | 3.45 |
| PRSS35 | protease, serine, 35 | NM_001170423 | 3.45 |
| PKIB | protein kinase (cAMP-dependent, catalytic) inhibitor beta | NM_181794 | 3.44 |
| RSPO3 | R-spondin 3 homolog (Xenopus laevis) | NM_032784 | 3.44 |
| TCF21 | transcription factor 21 | NM_003206 | 3.44 |
| TIAM2 | T-cell lymphoma invasion and metastasis 2 | NM_012454 | 3.44 |
| SMOC2 | SPARC related modular calcium binding 2 | | 3.43 |
| SERPINB9 | serpin peptidase inhibitor, clade B (ovalbumin), member 9 | NM_004155 | 3.42 |
| TUBB2B | tubulin, beta 2B | NM_178012 | 3.40 |
| HIST1H3F | histone cluster 1, H3f | NM_021018 | 3.40 |
| ZNF204P | zinc finger protein 204, pseudogene | | 3.39 |
| Tr. 8124604 | | | 3.39 |
| C6orf132 | chromosome 6 open reading frame 132 | | 3.38 |
| KHDRBS2 | KH domain containing, RNA binding, signal transduction associated 2 | NM_152688 | 3.37 |
| SRSF12 | serine/arginine-rich splicing factor 12 | NM_080743 | 3.37 |
| BACH2 | BTB and CNC homology 1, basic leucine zipper transcription factor 2 | NM_021813 | 3.36 |
| FYN | | NM_002037 | 3.36 |

FIG. 20 (15)

| genesymbol | genedescription | Accession number | Fold Change |
|---|---|---|---|
| MAP7 | microtubule-associated protein 7 | NM_003980 | 3.35 |
| EZR | ezrin | NM_003379 | 3.35 |
| SNORA20 | small nucleolar RNA, H/ACA box 20 | | 3.33 |
| SDK1 | sidekick homolog 1, cell adhesion molecule (chicken) | NM_152744 | 3.32 |
| GLCCI1 | glucocorticoid induced transcript 1 | | 3.31 |
| TSPAN13 | tetraspanin 13 | | 3.31 |
| SNX10 | sorting nexin 10 | NM_013322 | 3.31 |
| PRR15 | proline rich 15 | NM_175887 | 3.31 |
| AQP1 | aquaporin 1 (Colton blood group) | NM_198098 | 3.31 |
| WBSCR17 | Williams-Beuren syndrome chromosome region 17 | | 3.30 |
| GNAI1 | guanine nucleotide binding protein (G protein), alpha inhibiting activity polypeptide 1 | NM_002069 | 3.29 |
| FLNC | filamin C, gamma | | 3.29 |
| MEST | mesoderm specific transcript homolog (mouse) | NM_002402 | 3.27 |
| TRIM24 | tripartite motif-containing 24 | NM_015905 | 3.27 |
| ARHGEF5\|LOC728377 | Rho guanine nucleotide exchange factor (GEF) 5 \| Rho guanine nucleotide exchange factor (GEF) 5 pseudogene | NM_005435 | 3.27 |
| ICA1 | islet cell autoantigen 1, 69kDa | NM_004968 | 3.27 |
| SKAP2 | src kinase associated phosphoprotein 2 | NM_003930 | 3.26 |
| HOXA1 | homeobox A1 | NM_005522 | 3.26 |
| TRIL | TLR4 interactor with leucine-rich repeats | NM_014817 | 3.26 |
| ELMO1 | engulfment and cell motility 1 | NM_014800 | 3.26 |
| TNS3 | tensin 3 | NM_022748 | 3.26 |
| COBL | cordon-bleu homolog (mouse) | | 3.26 |
| DLX5 | distal-less homeobox 5 | NM_005221 | 3.25 |
| BAIAP2L1 | BAI1-associated protein 2-like 1 | NM_018842 | 3.25 |
| WNT2 | wingless-type MMTV integration site family member 2 | NM_003391 | 3.25 |
| TSPAN12 | tetraspanin 12 | NM_012338 | 3.25 |
| ARHGEF5\|ARHGEF35\|LOC728377\|OR2A7 | Rho guanine nucleotide exchange factor (GEF) 5 \| Rho guanine nucleotide exchange factor (GEF) 35 \| Rho guanine nucleotide exchange factor (GEF) 5 pseudogene \| olfactory receptor, family 2, subfamily A, member 7 | NM_005435 | 3.24 |
| OR2A7\|OR2A4\|LOC728377 | olfactory receptor, family 2, subfamily A, member 7 \| olfactory receptor, family 2, subfamily A, member 4 \| Rho guanine nucleotide exchange factor (GEF) 5 pseudogene | NM_001005328 | 3.24 |
| XKR4 | XK, Kell blood group complex subunit-related family, member 4 | | 3.24 |
| ADHFE1 | alcohol dehydrogenase, iron containing, 1 | NM_144650 | 3.23 |
| CRISPLD1 | cysteine-rich secretory protein LCCL domain containing 1 | | 3.23 |
| MATN2 | matrilin 2 | NM_002380 | 3.23 |
| C8orf42 | chromosome 8 open reading frame 42 | NM_175075 | 3.23 |
| SGK223 | homolog of rat pragma of Rnd2 | NM_001080826 | 3.23 |
| PPP1R3B | protein phosphatase 1, regulatory (inhibitor) subunit 3B | NM_024607 | 3.22 |
| MTMR7 | myotubularin related protein 7 | NM_004686 | 3.20 |
| SFRP1 | secreted frizzled-related protein 1 | NM_003012 | 3.20 |
| TOX | thymocyte selection-associated high mobility group box | | 3.19 |
| PDE7A | phosphodiesterase 7A | NM_002603 | 3.19 |
| JPH1 | junctophilin 1 | NM_020647 | 3.18 |

FIG. 20 (16)

| genesymbol | genedescription | Accession number | Fold Change |
|---|---|---|---|
| ZNF704 | zinc finger protein 704 | | 3.18 |
| PAG1 | phosphoprotein associated with glycosphingolipid microdomains 1 | NM_018440 | 3.18 |
| RUNX1T1 | runt-related transcription factor 1; translocated to, 1 (cyclin D-related) | NM_001198625 | 3.18 |
| RSPO2 | R-spondin 2 homolog (Xenopus laevis) | NM_178565 | 3.17 |
| KCNV1 | potassium channel, subfamily V, member 1 | NM_014379 | 3.16 |
| KANK1 | KN motif and ankyrin repeat domains 1 | NM_153186 | 3.16 |
| TEK | | NM_000459 | 3.16 |
| KRT18 | keratin 18 | NM_000224 | 3.16 |
| TJP2 | tight junction protein 2 (zona occludens 2) | NM_004817 | 3.16 |
| PCSK5 | proprotein convertase subtilisin/kexin type 5 | NM_001190482 | 3.16 |
| PSAT1 | phosphoserine aminotransferase 1 | NM_058179 | 3.15 |
| TMEFF1 | transmembrane protein with EGF-like and two follistatin-like domains 1 | NM_003692 | 3.14 |
| RALGPS1 | Ral GEF with PH domain and SH3 binding motif 1 | NM_014636 | 3.13 |
| GARNL3 | GTPase activating Rap/RanGAP domain-like 3 | NM_032293 | 3.13 |
| AIF1L | allograft inflammatory factor 1-like | | 3.12 |
| FAM69B | family with sequence similarity 69, member B | | 3.12 |
| MOBKL2B | MOB1, Mps One Binder kinase activator-like 2B (yeast) | | 3.11 |
| KIAA1161 | | NM_020702 | 3.11 |
| RASEF | RAS and EF-hand domain containing | NM_152573 | 3.11 |
| ROR2 | receptor tyrosine kinase-like orphan receptor 2 | NM_004560 | 3.11 |
| CORO2A | coronin, actin binding protein, 2A | NM_003389 | 3.10 |
| NOTCH1 | notch 1 | NM_017617 | 3.10 |
| CSF2RA | colony stimulating factor 2 receptor, alpha, low-affinity (granulocyte-macrophage) | | 3.09 |
| TBL1X | transducin (beta)-like 1X-linked | NM_005647 | 3.09 |
| SHROOM2 | shroom family member 2 | NM_001649 | 3.09 |
| SYTL5 | synaptotagmin-like 5 | NM_138780 | 3.09 |
| CLCN5 | chloride channel 5 | NM_001127899 | 3.08 |
| XAGE2|XAGE2B | X antigen family, member 2 | X antigen family, member 2B | | 3.07 |
| LPAR4 | lysophosphatidic acid receptor 4 | NM_005296 | 3.07 |
| PCDH11X|PCDH11Y | protocadherin 11 X-linked | protocadherin 11 Y-linked | NM_032967 | 3.06 |
| Tr. 8168674 | | | 3.06 |
| PLP1 | proteolipid protein 1 | NM_000533 | 3.05 |
| NRK | Nik related kinase | NM_198465 | 3.05 |
| MST4 | | NM_016542 | 3.05 |
| CSAG2|CSAG3 | CSAG family, member 2 | CSAG family, member 3 | NM_001080848 | 3.04 |
| MID1 | midline 1 (Opitz/BBB syndrome) | NM_000381 | 3.04 |
| TMEM27 | transmembrane protein 27 | NM_020665 | 3.04 |
| AKAP4 | A kinase (PRKA) anchor protein 4 | NM_003886 | 3.04 |
| XAGE2|XAGE2B | X antigen family, member 2 | X antigen family, member 2B | | 3.04 |
| ITM2A | integral membrane protein 2A | | 3.04 |
| BEX1 | brain expressed, X-linked 1 | NM_018476 | 3.03 |
| HS6ST2 | heparan sulfate 6-O-sulfotransferase 2 | NM_001077188 | 3.01 |
| MIR503 | microRNA 503 | | 3.01 |

FIG. 20 (17)

| genesymbol | genedescription | Accession number | Fold Change |
|---|---|---|---|
| GABRA3 | gamma-aminobutyric acid (GABA) A receptor, alpha 3 | NM_000808 | 3.01 |
| CSAG2|CSAG3 | CSAG family, member 2 | CSAG family, member 3 | NM_001080848 | 3.01 |
| CSF2RA | colony stimulating factor 2 receptor, alpha, low-affinity (granulocyte-macrophage) | | 3.01 |
| PCDH11Y|PCDH11X | protocadherin 11 Y-linked | protocadherin 11 X-linked | NM_032971 | 3.01 |
| CD24 | | NM_013230 | 3.00 |
| MARVELD2 | MARVEL domain containing 2 | NM_001038603 | 3.00 |
| ZNF471 | zinc finger protein 471 | NM_020813 | -3.01 |
| PRAF2|WDR45 | PRA1 domain family, member 2 | WD repeat domain 45 | NM_007213 | -3.01 |
| PFKFB3 | 6-phosphofructo-2-kinase/fructose-2,6-biphosphatase 3 | NM_004566 | -3.02 |
| HERC6 | hect domain and RLD 6 | NM_017912 | -3.04 |
| SAMD15 | sterile alpha motif domain containing 15 | | -3.04 |
| HRH1 | histamine receptor H1 | NM_001098213 | -3.04 |
| SPOCK1 | sparc/osteonectin, cwcv and kazal-like domains proteoglycan (testican) 1 | NM_004598 | -3.04 |
| COPZ2 | coatomer protein complex, subunit zeta 2 | NM_016429 | -3.05 |
| NR4A1 | nuclear receptor subfamily 4, group A, member 1 | NM_002135 | -3.05 |
| LOC645166|LOC654342 | lymphocyte-specific protein 1 pseudogene | | -3.05 |
| CLIP4 | CAP-GLY domain containing linker protein family, member 4 | | -3.06 |
| LRRK2 | leucine-rich repeat kinase 2 | NM_198578 | -3.06 |
| GXYLT2 | glucoside xylosyltransferase 2 | NM_001080393 | -3.07 |
| DHRS3 | dehydrogenase/reductase (SDR family) member 3 | NM_004753 | -3.07 |
| C1orf54 | chromosome 1 open reading frame 54 | | -3.07 |
| ABCC4 | ATP-binding cassette, sub-family C (CFTR/MRP), member 4 | NM_005845 | -3.08 |
| PSMB8 | proteasome (prosome, macropain) subunit, beta type, 8 (large multifunctional peptidase 7) | NM_004159 | -3.09 |
| PSMB8 | proteasome (prosome, macropain) subunit, beta type, 8 (large multifunctional peptidase 7) | NM_004159 | -3.09 |
| PSMB8 | proteasome (prosome, macropain) subunit, beta type, 8 (large multifunctional peptidase 7) | NM_004159 | -3.09 |
| MDGA1 | MAM domain containing glycosylphosphatidylinositol anchor 1 | NM_153487 | -3.09 |
| ZNF562 | zinc finger protein 562 | NM_001130031 | -3.09 |
| NDP | Norrie disease (pseudoglioma) | NM_000266 | -3.10 |
| TSPO | translocator protein (18kDa) | NM_000714 | -3.10 |
| Tr. 8163253 | | | -3.10 |
| ITPRIP | inositol 1,4,5-triphosphate receptor interacting protein | | -3.11 |
| PAK3 | p21 protein (Cdc42/Rac)-activated kinase 3 | NM_002578 | -3.11 |
| CD97 | | NM_078481 | -3.11 |
| GLS | glutaminase | NM_014905 | -3.12 |
| Tr. 8037387 | | | -3.12 |
| ZNFX1 | zinc finger, NFX1-type containing 1 | | -3.12 |
| TAP2 | transporter 2, ATP-binding cassette, sub-family B (MDR/TAP) | NM_018833 | -3.13 |
| MORC4 | MORC family CW-type zinc finger 4 | | -3.13 |
| NRP1 | neuropilin 1 | NM_003873 | -3.14 |

FIG. 20 (18)

| genesymbol | genedescription | Accession number | Fold Change |
|---|---|---|---|
| STAT1 | signal transducer and activator of transcription 1, 91kDa | NM_007315 | -3.15 |
| PCDHB13 | protocadherin beta 13 | NM_018933 | -3.15 |
| PC | pyruvate carboxylase | NM_001040716 | -3.16 |
| FKBP5|LOC285847 | FK506 binding protein 5 | hypothetical LOC285847 | NM_001145775 | -3.16 |
| MPHOSPH6 | M-phase phosphoprotein 6 | NM_005792 | -3.16 |
| NIPAL2 | NIPA-like domain containing 2 |  | -3.17 |
| SLC9A7 | solute carrier family 9 (sodium/hydrogen exchanger), member 7 | NM_032591 | -3.17 |
| ANO5 | anoctamin 5 | NM_213599 | -3.17 |
| SLCO3A1 | solute carrier organic anion transporter family, member 3A1 | NM_013272 | -3.17 |
| C16orf45 | chromosome 16 open reading frame 45 |  | -3.17 |
| DNAJB4 | DnaJ (Hsp40) homolog, subfamily B, member 4 | NM_007034 | -3.17 |
| SNX25 | sorting nexin 25 | NM_031953 | -3.17 |
| BDNF | brain-derived neurotrophic factor | NM_170732 | -3.19 |
| TBC1D8B | TBC1 domain family, member 8B (with GRAM domain) | NM_017752 | -3.19 |
| C1GALT1C1 | C1GALT1-specific chaperone 1 |  | -3.20 |
| WDR52 | WD repeat domain 52 |  | -3.21 |
| Tr. 8043500 |  |  | -3.21 |
| NR3C1 | nuclear receptor subfamily 3, group C, member 1 (glucocorticoid receptor) | NM_000176 | -3.21 |
| PDE8A | phosphodiesterase 8A | NM_002605 | -3.21 |
| CMPK2 | cytidine monophosphate (UMP-CMP) kinase 2, mitochondrial | NM_207315 | -3.22 |
| ANKRD42 | ankyrin repeat domain 42 |  | -3.22 |
| TBX2 | T-box 2 | NM_005994 | -3.24 |
| SMAP2 | small ArfGAP2 | NM_022733 | -3.24 |
| AEBP1 | AE binding protein 1 | NM_001129 | -3.25 |
| PRKCA | protein kinase C, alpha | NM_002737 | -3.25 |
| WDR35 | WD repeat domain 35 |  | -3.25 |
| ADAM15 | ADAM metallopeptidase domain 15 | NM_207196 | -3.26 |
| SNORD56B | small nucleolar RNA, C/D box 56B |  | -3.28 |
| ARSB | arylsulfatase B | NM_000046 | -3.28 |
| DYRK3 | dual-specificity tyrosine-(Y)-phosphorylation regulated kinase 3 | NM_001004023 | -3.28 |
| PDLIM5 | PDZ and LIM domain 5 | NM_006457 | -3.29 |
| QSOX1|FLJ23867 | quiescin Q6 sulfhydryl oxidase 1 | hypothetical protein FLJ23867 | NM_002826 | -3.29 |
| ZNF585B | zinc finger protein 585B | NM_152279 | -3.30 |
| CNTNAP1 | contactin associated protein 1 | NM_003632 | -3.31 |
| NAV1 | neuron navigator 1 | NM_020443 | -3.32 |
| PODNL1 | podocan-like 1 |  | -3.32 |
| NFIB | nuclear factor I/B | NM_001190737 | -3.32 |
| G6PD | glucose-6-phosphate dehydrogenase | NM_000402 | -3.33 |
| SYNC | syncoilin, intermediate filament protein | NM_030786 | -3.33 |
| ICAM1 | intercellular adhesion molecule 1 | NM_000201 | -3.34 |
| PITX2 | paired-like homeodomain 2 | NM_153426 | -3.34 |
| NTN4 | netrin 4 | NM_021229 | -3.37 |

FIG. 20 (19)

| genesymbol | genedescription | Accession number | Fold Change |
|---|---|---|---|
| TAPBPL\|VAMP1 | TAP binding protein-like \| vesicle-associated membrane protein 1 (synaptobrevin 1) | NM_018009 | -3.38 |
| GNG12 | guanine nucleotide binding protein (G protein), gamma 12 | NM_018841 | -3.40 |
| NHSL1 | NHS-like 1 | | -3.40 |
| FLJ38109 | hypothetical LOC386627 | | -3.40 |
| AVPI1 | arginine vasopressin-induced 1 | NM_021732 | -3.41 |
| PLCD3 | phospholipase C, delta 3 | NM_133373 | -3.42 |
| SGIP1 | SH3-domain GRB2-like (endophilin) interacting protein 1 | NM_032291 | -3.42 |
| SIAE | sialic acid acetylesterase | | -3.44 |
| ABCA10 | ATP-binding cassette, sub-family A (ABC1), member 10 | NM_080282 | -3.44 |
| FAM46C | family with sequence similarity 46, member C | | -3.44 |
| NRG1\|LOC100507358 | neuregulin 1 \| hypothetical protein LOC100507358 | AF176921 | -3.44 |
| RNF112 | ring finger protein 112 | | -3.45 |
| ELL2 | elongation factor, RNA polymerase II, 2 | NM_012081 | -3.45 |
| CDH2 | cadherin 2, type 1, N-cadherin (neuronal) | NM_001792 | -3.46 |
| STEAP4 | STEAP family member 4 | NM_024636 | -3.46 |
| Tr. 8079163 | | | -3.46 |
| ID3 | inhibitor of DNA binding 3, dominant negative helix-loop-helix protein | NM_002167 | -3.47 |
| EFR3B | EFR3 homolog B (S. cerevisiae) | | -3.48 |
| GLB1L | galactosidase, beta 1-like | NM_024506 | -3.48 |
| PODN | podocan | NM_153703 | -3.49 |
| C19orf66\|ANGPTL6 | chromosome 19 open reading frame 66 \| angiopoietin-like 6 | NM_031917 | -3.49 |
| ZNF596 | zinc finger protein 596 | NM_001042416 | -3.49 |
| PLCB4 | phospholipase C, beta 4 | NM_001172646 | -3.50 |
| SP110 | | NM_080424 | -3.51 |
| PAPPA\|PAPPAS | pregnancy-associated plasma protein A, pappalysin 1 \| PAPPA antisense RNA (non-protein coding) | NM_002581 | -3.52 |
| EML6 | echinoderm microtubule associated protein like 6 | | -3.52 |
| ADAM12 | ADAM metallopeptidase domain 12 | NM_003474 | -3.53 |
| Tr. 7919749 | | | -3.53 |
| KCNAB2 | potassium voltage-gated channel, shaker-related subfamily, beta member 2 | NM_003636 | -3.54 |
| MICB | MHC class I polypeptide-related sequence B | NM_005931 | -3.54 |
| ABCA8 | ATP-binding cassette, sub-family A (ABC1), member 8 | NM_007168 | -3.54 |
| SLC12A2 | solute carrier family 12 (sodium/potassium/chloride transporters), member 2 | NM_001046 | -3.55 |
| ULBP2 | UL16 binding protein 2 | NM_025217 | -3.55 |
| DNAJC12 | DnaJ (Hsp40) homolog, subfamily C, member 12 | | -3.56 |
| TAP2 | transporter 2, ATP-binding cassette, sub-family B (MDR/TAP) | NM_000544 | -3.56 |
| CASP4 | caspase 4, apoptosis-related cysteine peptidase | NM_033306 | -3.58 |
| SPON1 | spondin 1, extracellular matrix protein | NM_006108 | -3.58 |
| GLIS1 | GLIS family zinc finger 1 | NM_147193 | -3.59 |
| APOBEC3G | apolipoprotein B mRNA editing enzyme, catalytic polypeptide-like 3G | NM_021822 | -3.59 |
| PSD3 | pleckstrin and Sec7 domain containing 3 | NM_015310 | -3.60 |

FIG. 20 (20)

| genesymbol | genedescription | Accession number | Fold Change |
|---|---|---|---|
| IFIT5 | interferon-induced protein with tetratricopeptide repeats 5 | NM_012420 | -3.60 |
| ARHGAP26 | Rho GTPase activating protein 26 | NM_015071 | -3.61 |
| C3orf55 | chromosome 3 open reading frame 55 | | -3.61 |
| BLID | BH3-like motif containing, cell death inducer | NM_001001786 | -3.62 |
| GAP43 | growth associated protein 43 | NM_001130064 | -3.62 |
| Tr. 7977951 | | | -3.62 |
| USP18 | ubiquitin specific peptidase 18 | NM_017414 | -3.63 |
| TAP2 | transporter 2, ATP-binding cassette, sub-family B (MDR/TAP) | NM_000544 | -3.63 |
| APBA1 | amyloid beta (A4) precursor protein-binding, family A, member 1 | NM_001163 | -3.63 |
| SUSD2 | sushi domain containing 2 | NM_019601 | -3.63 |
| ANKRD44 | ankyrin repeat domain 44 | | -3.64 |
| ACVR1 | activin A receptor, type I | NM_001105 | -3.64 |
| ME1 | malic enzyme 1, NADP(+)-dependent, cytosolic | NM_002395 | -3.64 |
| PARP3 | poly (ADP-ribose) polymerase family, member 3 | NM_001003931 | -3.64 |
| DYNC1I1 | dynein, cytoplasmic 1, intermediate chain 1 | NM_004411 | -3.64 |
| TIPARP | TCDD-inducible poly(ADP-ribose) polymerase | NM_015508 | -3.65 |
| FLI1\|EWSR1 | Friend leukemia virus integration 1 \| Ewing sarcoma breakpoint region 1 | NM_002017 | -3.66 |
| RGS4 | regulator of G-protein signaling 4 | NM_001102445 | -3.66 |
| C4orf26 | chromosome 4 open reading frame 26 | | -3.66 |
| UBA7 | ubiquitin-like modifier activating enzyme 7 | NM_003335 | -3.67 |
| NTM | neurotrimin | NM_016522 | -3.68 |
| AMIGO2 | adhesion molecule with Ig-like domain 2 | NM_001143668 | -3.70 |
| TBC1D19 | TBC1 domain family, member 19 | NM_018317 | -3.71 |
| MRC2 | mannose receptor, C type 2 | NM_006039 | -3.73 |
| CCPG1 | cell cycle progression 1 | NM_004748 | -3.74 |
| CPEB4 | cytoplasmic polyadenylation element binding protein 4 | | -3.74 |
| DCC | deleted in colorectal carcinoma | NM_005215 | -3.76 |
| CTSF | cathepsin F | NM_003793 | -3.76 |
| FAM101B | family with sequence similarity 101, member B | | -3.77 |
| PSD3 | pleckstrin and Sec7 domain containing 3 | NM_015310 | -3.77 |
| NME5 | non-metastatic cells 5, protein expressed in (nucleoside-diphosphate kinase) | NM_003551 | -3.78 |
| CPEB2 | cytoplasmic polyadenylation element binding protein 2 | NM_182485 | -3.78 |
| APOL2 | apolipoprotein L, 2 | NM_030882 | -3.79 |
| TRIM14 | tripartite motif-containing 14 | NM_014788 | -3.80 |
| RBFOX1 | RNA binding protein, fox-1 homolog (C. elegans) 1 | NM_018723 | -3.80 |
| WNT5A | wingless-type MMTV integration site family, member 5A | NM_003392 | -3.81 |
| ZNF248 | zinc finger protein 248 | NM_021045 | -3.81 |
| DUSP4 | dual specificity phosphatase 4 | NM_001394 | -3.81 |
| FGF2\|NUDT6 | fibroblast growth factor 2 (basic) \| nudix (nucleoside diphosphate linked moiety X)-type motif 6 | NM_002006 | -3.84 |
| KLF9 | Kruppel-like factor 9 | NM_001206 | -3.85 |
| SPRY4 | sprouty homolog 4 (Drosophila) | NM_030964 | -3.85 |
| INSIG1 | insulin induced gene 1 | NM_005542 | -3.86 |

FIG. 20 (21)

| genesymbol | genedescription | Accession number | Fold Change |
|---|---|---|---|
| ZEB1 | zinc finger E-box binding homeobox 1 | NM_030751 | -3.87 |
| ACAD11|NPHP3 | acyl-CoA dehydrogenase family, member 11 | nephronophthisis 3 (adolescent) | NM_032169 | -3.87 |
| MICB | MHC class I polypeptide-related sequence B | NM_005931 | -3.88 |
| AP1S3 | adaptor-related protein complex 1, sigma 3 subunit | NM_001039569 | -3.88 |
| LPXN | leupaxin | NM_004811 | -3.90 |
| CXCL11 | chemokine (C-X-C motif) ligand 11 | NM_005409 | -3.91 |
| SMAD9 | SMAD family member 9 | NM_001127217 | -3.94 |
| SLC9A3R2 | solute carrier family 9 (sodium/hydrogen exchanger), member 3 regulator 2 | NM_001130012 | -3.95 |
| PDGFRA | platelet-derived growth factor receptor, alpha polypeptide | NM_006206 | -3.96 |
| AOX1 | aldehyde oxidase 1 | NM_001159 | -3.96 |
| Tr. 8045347 | | | -3.96 |
| CNTN6 | contactin 6 | NM_014461 | -3.96 |
| LMO7 | LIM domain 7 | NM_005358 | -3.98 |
| ADAMTSL1 | ADAMTS-like 1 | | -3.98 |
| TMEM22 | transmembrane protein 22 | | -4.00 |
| C18orf1 | chromosome 18 open reading frame 1 | NM_181481 | -4.02 |
| TMEM100 | transmembrane protein 100 | NM_001099640 | -4.03 |
| BMP2 | bone morphogenetic protein 2 | NM_001200 | -4.04 |
| Tr. 7969091 | | | -4.05 |
| CHRNA5 | cholinergic receptor, nicotinic, alpha 5 | NM_000745 | -4.05 |
| PID1 | phosphotyrosine interaction domain containing 1 | | -4.05 |
| SNED1 | sushi, nidogen and EGF-like domains 1 | NM_001080437 | -4.09 |
| TRIM22 | tripartite motif-containing 22 | NM_006074 | -4.10 |
| KCNJ15 | potassium inwardly-rectifying channel, subfamily J, member 15 | NM_002243 | -4.10 |
| DDX58 | DEAD (Asp-Glu-Ala-Asp) box polypeptide 58 | NM_014314 | -4.11 |
| Tr. 8058201 | | | -4.12 |
| FBN1 | fibrillin 1 | NM_000138 | -4.13 |
| CNRIP1 | cannabinoid receptor interacting protein 1 | | -4.13 |
| NR1D1|THRA | nuclear receptor subfamily 1, group D, member 1 | thyroid hormone receptor, alpha (erythroblastic leukemia viral (v-erb-a) oncogene homolog, avian) | NM_021724 | -4.13 |
| TGFBR3 | transforming growth factor, beta receptor III | NM_003243 | -4.15 |
| IL1RAP | interleukin 1 receptor accessory protein | NM_002182 | -4.17 |
| HIST1H1A | histone cluster 1, H1a | NM_005325 | -4.19 |
| C9orf150 | chromosome 9 open reading frame 150 | | -4.20 |
| NFASC | neurofascin | NM_001005388 | -4.21 |
| MEGF9 | multiple EGF-like-domains 9 | NM_001080497 | -4.21 |
| IFIH1 | interferon induced with helicase C domain 1 | NM_022168 | -4.22 |
| MIR155|MIR155HG | microRNA 155 | MIR155 host gene (non-protein coding) | | -4.22 |
| ASAM | adipocyte-specific adhesion molecule | | -4.22 |
| ABCA6 | ATP-binding cassette, sub-family A (ABC1), member 6 | NM_080284 | -4.24 |
| ZSWIM5 | zinc finger, SWIM-type containing 5 | | -4.24 |
| NOG | noggin | NM_005450 | -4.25 |
| FLRT2 | fibronectin leucine rich transmembrane protein 2 | NM_013231 | -4.26 |

FIG. 20 (22)

| genesymbol | genedescription | Accession number | Fold Change |
|---|---|---|---|
| SRXN1 | sulfiredoxin 1 | NM_080725 | -4.27 |
| FAIM2 | Fas apoptotic inhibitory molecule 2 | NM_012306 | -4.29 |
| DUSP1 | dual specificity phosphatase 1 | NM_004417 | -4.29 |
| MIR29A | microRNA 29a | | -4.29 |
| RORA | RAR-related orphan receptor A | NM_134260 | -4.30 |
| KGFLP2\|KGFLP1\|FGF7\|FLJ20444 | keratinocyte growth factor-like protein 2 \| keratinocyte growth factor-like protein 1 \| fibroblast growth factor 7 \| hypothetical protein FLJ20444 | NR_003670 | -4.31 |
| KAT2B | K(lysine) acetyltransferase 2B | NM_003884 | -4.31 |
| Tr. 8099393 | | | -4.31 |
| ACOX2 | acyl-CoA oxidase 2, branched chain | NM_003500 | -4.32 |
| STIM2 | stromal interaction molecule 2 | NM_001169118 | -4.33 |
| CD248 | | NM_020404 | -4.35 |
| MGAT5 | mannosyl (alpha-1,6-)-glycoprotein beta-1,6-N-acetyl-glucosaminyltransferase | NM_002410 | -4.35 |
| Tr. 8002301 | | | -4.36 |
| PLOD2 | procollagen-lysine, 2-oxoglutarate 5-dioxygenase 2 | NM_182943 | -4.37 |
| HIST2H2BF\|HIST2H2BA\|HIST2H2BE | histone cluster 2, H2bf \| histone cluster 2, H2ba \| histone cluster 2, H2be | NM_001024599 | -4.38 |
| PTPRG | protein tyrosine phosphatase, receptor type, G | NM_002841 | -4.38 |
| GK | glycerol kinase | NM_001128127 | -4.39 |
| Tr. 8121884 | | | -4.39 |
| SAT1 | spermidine/spermine N1-acetyltransferase 1 | NR_027783 | -4.40 |
| COMT | catechol-O-methyltransferase | NM_000754 | -4.41 |
| ELTD1 | EGF, latrophilin and seven transmembrane domain containing 1 | NM_022159 | -4.45 |
| MCAM | melanoma cell adhesion molecule | NM_006500 | -4.45 |
| SLC20A1 | solute carrier family 20 (phosphate transporter), member 1 | NM_005415 | -4.46 |
| Tr. 8163255 | | | -4.47 |
| LTBP3 | latent transforming growth factor beta binding protein 3 | NM_001130144 | -4.48 |
| SNORD116-21\|SNORD116@ | small nucleolar RNA, C/D box 116-21 \| small nucleolar RNA, C/D box 116 cluster | | -4.48 |
| Tr. 8165692 | | | -4.49 |
| TGFB1 | transforming growth factor, beta 1 | NM_000660 | -4.49 |
| SLC7A8 | solute carrier family 7 (amino acid transporter, L-type), member 8 | NM_012244 | -4.51 |
| VDR | vitamin D (1,25- dihydroxyvitamin D3) receptor | NM_001017535 | -4.51 |
| GK\|GK3P | glycerol kinase \| glycerol kinase 3 pseudogene | NM_001128127 | -4.52 |
| SLC6A6 | solute carrier family 6 (neurotransmitter transporter, taurine), member 6 | NM_003043 | -4.52 |
| CPEB1 | cytoplasmic polyadenylation element binding protein 1 | NM_030594 | -4.54 |
| PCBP3 | poly(rC) binding protein 3 | NM_020528 | -4.54 |
| PRNP | prion protein | NM_000311 | -4.55 |
| IGFBP4 | insulin-like growth factor binding protein 4 | NM_001552 | -4.55 |
| ZNF454 | zinc finger protein 454 | NM_001178089 | -4.57 |
| LGALS1 | lectin, galactoside-binding, soluble, 1 | NM_002305 | -4.59 |
| CSGALNACT2 | chondroitin sulfate N-acetylgalactosaminyltransferase 2 | NM_018590 | -4.60 |
| HBEGF | heparin-binding EGF-like growth factor | NM_001945 | -4.60 |

FIG. 20 (23)

| genesymbol | genedescription | Accession number | Fold Change |
|---|---|---|---|
| GEM | GTP binding protein overexpressed in skeletal muscle | NM_005261 | -4.65 |
| ZNF676 | zinc finger protein 676 | NM_001001411 | -4.65 |
| LOC100128252\|LOC100288114 | hypothetical LOC100128252 \| hypothetical LOC100288114 | | -4.68 |
| C13orf31 | chromosome 13 open reading frame 31 | | -4.70 |
| VEPH1 | ventricular zone expressed PH domain homolog 1 (zebrafish) | | -4.72 |
| DDX60L | DEAD (Asp-Glu-Ala-Asp) box polypeptide 60-like | | -4.74 |
| PLAT | plasminogen activator, tissue | NM_000930 | -4.77 |
| NHEDC2 | Na+/H+ exchanger domain containing 2 | NM_178833 | -4.79 |
| Tr. 8009073 | | | -4.79 |
| CORO2B | coronin, actin binding protein, 2B | NM_006091 | -4.80 |
| BHMT2 | betaine--homocysteine S-methyltransferase 2 | NM_017614 | -4.81 |
| GMDS | GDP-mannose 4,6-dehydratase | NM_001500 | -4.81 |
| TMEM173 | transmembrane protein 173 | NM_198282 | -4.82 |
| TFPI2 | tissue factor pathway inhibitor 2 | NM_006528 | -4.83 |
| IGFBP6 | insulin-like growth factor binding protein 6 | NM_002178 | -4.85 |
| AHR | aryl hydrocarbon receptor | NM_001621 | -4.87 |
| MAP1A | microtubule-associated protein 1A | | -4.90 |
| PROCR | protein C receptor, endothelial | NM_006404 | -4.90 |
| ETV5 | ets variant 5 | NM_004454 | -4.95 |
| ABCA5 | ATP-binding cassette, sub-family A (ABC1), member 5 | NM_018672 | -4.95 |
| Tr. 8043502 | | | -4.97 |
| ATOH8 | atonal homolog 8 (Drosophila) | NM_032827 | -5.02 |
| CTSK | cathepsin K | NM_000396 | -5.02 |
| LGALS3BP | lectin, galactoside-binding, soluble, 3 binding protein | NM_005567 | -5.02 |
| C10orf116\|AGAP11 | chromosome 10 open reading frame 116 \| ankyrin repeat and GTPase domain Arf GTPase activating protein 11 | NM_006829 | -5.05 |
| ENG | endoglin | NM_000118 | -5.11 |
| PGCP | plasma glutamate carboxypeptidase | NM_016134 | -5.13 |
| CDYL2 | chromodomain protein, Y-like 2 | NM_152342 | -5.17 |
| PARP12 | poly (ADP-ribose) polymerase family, member 12 | | -5.19 |
| MGP | matrix Gla protein | NM_001190839 | -5.21 |
| SULF1 | sulfatase 1 | NM_001128205 | -5.24 |
| CDH13 | cadherin 13, H-cadherin (heart) | NM_001257 | -5.25 |
| Tr. 8079742 | | | -5.27 |
| PLAUR | plasminogen activator, urokinase receptor | NM_002659 | -5.28 |
| LY96 | lymphocyte antigen 96 | NM_015364 | -5.30 |
| EMX2 | empty spiracles homeobox 2 | NM_004098 | -5.34 |
| BICC1 | bicaudal C homolog 1 (Drosophila) | NM_001080512 | -5.36 |
| DDX60 | DEAD (Asp-Glu-Ala-Asp) box polypeptide 60 | | -5.37 |
| TMTC1 | transmembrane and tetratricopeptide repeat containing 1 | | -5.37 |
| PARP9 | poly (ADP-ribose) polymerase family, member 9 | NM_031458 | -5.40 |
| SERPINB8 | serpin peptidase inhibitor, clade B (ovalbumin), member 8 | NM_002640 | -5.42 |
| SRPX2 | sushi-repeat-containing protein, X-linked 2 | NM_014467 | -5.43 |
| CD44 | | NM_000610 | -5.44 |
| NNMT | nicotinamide N-methyltransferase | | -5.44 |

FIG. 20 (24)

| genesymbol | genedescription | Accession number | Fold Change |
|---|---|---|---|
| NCAM1 | neural cell adhesion molecule 1 | NM_181351 | -5.47 |
| GLIS3 | GLIS family zinc finger 3 | NM_152629 | -5.52 |
| CPB2 | carboxypeptidase B2 (plasma) | NM_001872 | -5.53 |
| CLCA2 | chloride channel accessory 2 | NM_006536 | -5.56 |
| GPR1 | G protein-coupled receptor 1 | NM_005279 | -5.60 |
| MAMLD1 | mastermind-like domain containing 1 | NM_005491 | -5.63 |
| QPCT | glutaminyl-peptide cyclotransferase | NM_012413 | -5.64 |
| AHI1 | Abelson helper integration site 1 | | -5.65 |
| SAMD5 | sterile alpha motif domain containing 5 | | -5.67 |
| PAPSS2 | 3'-phosphoadenosine 5'-phosphosulfate synthase 2 | NM_004670 | -5.68 |
| IFI35 | interferon-induced protein 35 | NM_005533 | -5.68 |
| DKK1 | dickkopf homolog 1 (Xenopus laevis) | NM_012242 | -5.70 |
| RANBP3L | RAN binding protein 3-like | NM_001161429 | -5.73 |
| LRP8 | low density lipoprotein receptor-related protein 8, apolipoprotein e receptor | NM_004631 | -5.80 |
| PTPRM | protein tyrosine phosphatase, receptor type, M | NM_001105244 | -5.82 |
| EPHX4 | epoxide hydrolase 4 | | -5.82 |
| MALL | mal, T-cell differentiation protein-like | NM_005434 | -5.86 |
| ARHGAP20 | Rho GTPase activating protein 20 | NM_020809 | -5.90 |
| MFSD2A | major facilitator superfamily domain containing 2A | NM_001136493 | -5.96 |
| CYP1B1 | cytochrome P450, family 1, subfamily B, polypeptide 1 | NM_000104 | -5.98 |
| MX2 | myxovirus (influenza virus) resistance 2 (mouse) | NM_002463 | -6.03 |
| FGF10 | fibroblast growth factor 10 | NM_004465 | -6.08 |
| NFIC | nuclear factor I/C (CCAAT-binding transcription factor) | NM_205843 | -6.09 |
| PGM2L1 | phosphoglucomutase 2-like 1 | NM_173582 | -6.10 |
| SYT11 | synaptotagmin XI | | -6.14 |
| TEX15 | testis expressed 15 | NM_031271 | -6.16 |
| USP18\|USP41 | ubiquitin specific peptidase 18 \| ubiquitin specific peptidase 41 | NM_017414 | -6.35 |
| CD302\|LY75 | CD302 molecule \| lymphocyte antigen 75 | ENST00000409803 | -6.37 |
| CD68 | | | -6.39 |
| PDCD1LG2 | programmed cell death 1 ligand 2 | NM_025239 | -6.41 |
| MICA | MHC class I polypeptide-related sequence A | NM_001177519 | -6.42 |
| FHL1 | four and a half LIM domains 1 | NM_001159702 | -6.51 |
| MR1 | major histocompatibility complex, class I-related | NM_001531 | -6.63 |
| LMF1 | lipase maturation factor 1 | NM_022773 | -6.70 |
| B2M | beta-2-microglobulin | NM_004048 | -6.72 |
| DUSP6 | dual specificity phosphatase 6 | NM_001946 | -6.73 |
| IFIT2 | interferon-induced protein with tetratricopeptide repeats 2 | NM_001547 | -6.77 |
| TM4SF18 | transmembrane 4 L six family member 18 | | -7.11 |
| NR4A2 | nuclear receptor subfamily 4, group A, member 2 | NM_006186 | -7.14 |
| C5orf62 | chromosome 5 open reading frame 62 | | -7.16 |
| XYLT1 | xylosyltransferase I | NM_022166 | -7.16 |
| Tr. 8048976 | | | -7.27 |
| MICA | MHC class I polypeptide-related sequence A | NM_000247 | -7.35 |
| NQO1 | NAD(P)H dehydrogenase, quinone 1 | NM_000903 | -8.06 |

FIG. 20 (25)

| genesymbol | genedescription | Accession number | Fold Change |
|---|---|---|---|
| ABI3BP | ABI family, member 3 (NESH) binding protein |  | -8.14 |
| SNCA | synuclein, alpha (non A4 component of amyloid precursor) | NM_000345 | -8.21 |
| CA2 | carbonic anhydrase II | NM_000067 | -8.30 |
| TLR4 | toll-like receptor 4 | NR_024168 | -8.50 |
| PLCD4 | phospholipase C, delta 4 | NM_032726 | -8.60 |
| C1R | complement component 1, r subcomponent | NM_001733 | -9.89 |

FIG. 21
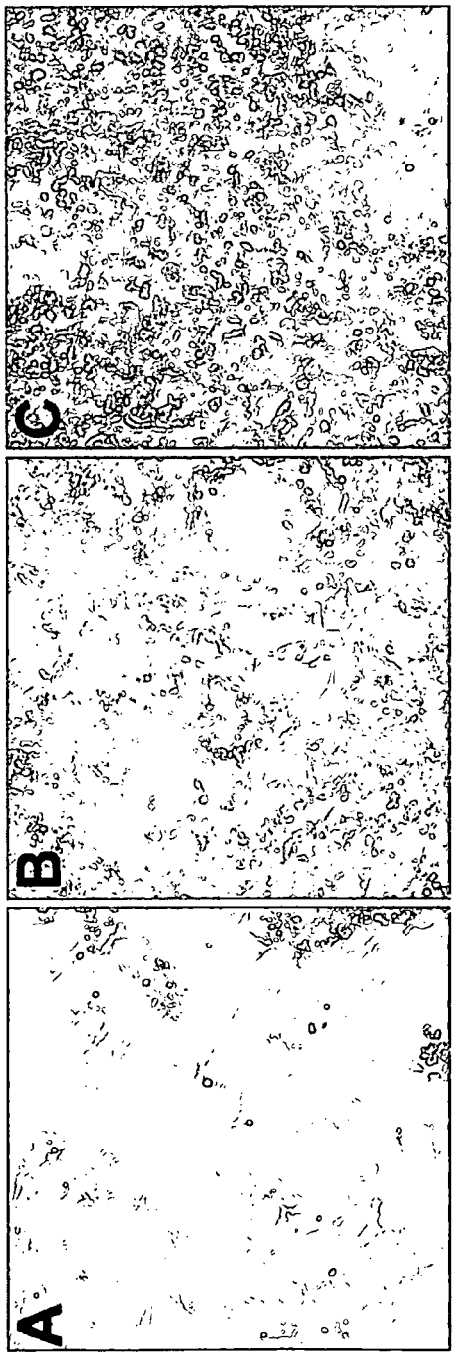
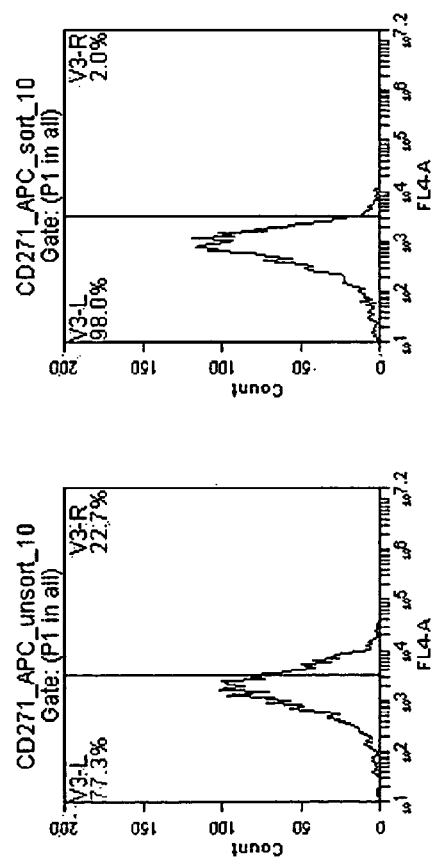

METHOD OF DIRECTED DIFFERENTIATION PRODUCING CORNEAL ENDOTHELIAL CELLS FROM NEURAL CREST STEM CELLS BY PDGFB AND DKK2, COMPOSITIONS THEREOF, AND USES THEREOF

RELATED APPLICATION DISCLOSURE

This application is a national stage filing under 35 U.S.C. §371 of International Application No. PCT/US2012/068305, filed Dec. 6, 2012, which was published under PCT Article 21(2) in English, and which claims the benefit under 35 U.S.C. §119(e) of U.S. Provisional Application Ser. No. 61/567,479, filed Dec. 6, 2011, each of which is incorporated by reference herein in its entirety.

FIELD

This disclosure generally relates to methods for directed differentiation of corneal cells from stem cells. Compositions of corneal endothelial cells, including pharmaceutical compositions, and uses thereof, are also disclosed. Also exemplified are cell-based therapies for treatment of visual disorders, including disorders of the cornea.

BACKGROUND

The cornea performs functions critical for normal vision and maintenance of eye health, including providing about two-thirds of the optical power of the eye and protecting the eye from injury or infection. Corneal disease and injury is a leading cause of blindness worldwide. Many corneal disease and injuries can be treated by transplantation of donor corneas. The cornea is the most transplanted organ in the body and has a high success rate over 15 years. For example, approximately 40,000 corneal transplantations are performed per year in the U.S. However, demand for corneas for transplantation greatly exceeds the current supply worldwide, and the limited quality and quantity of available donor tissue hinders treatment. One factor contributing to the inadequate supply of donated corneas is that up to 30% of donated corneas are rejected for transplantation due to poor quality of the corneal endothelium. Quality of the corneal endothelium generally decreases with donor age because, as the cornea ages or is injured, the endothelial cells die and are not replaced. Therefore, as the population ages, the supply of donor tissue having suitably healthy corneal endothelium decreases. Moreover, the number and quality of donated corneas is expected to decline as the popularity of LASIK surgery increases (these corneas are rejected for transplantation).

Diseases of the cornea may involve one or more of the cornea's five layers: the corneal epithelium, Bowman's layer, the corneal stroma, Descemet's membrane, and the corneal endothelium. The corneal epithelium, corneal stroma, and corneal endothelium are cellular layers, while Bowman's layer and Descemet's membrane are primarily composed of collagen fibrils. The corneal endothelium is a single layer of cells on the inner surface of the cornea. It faces the chamber formed between the cornea and the iris and keeps the cornea transparent by regulating fluid levels. Without functional corneal endothelium, the cornea becomes cloudy and vision is lost. Properly functioning corneal endothelial cells maintain the proper fluid levels in the cornea, e.g., the balance between "leakage" of fluid into the stroma and active pumping that continuously operates to move fluid from the stroma to the anterior chamber of the eye.

Corneal endothelial cells have been reported to have little or no capacity to proliferate in vivo, such that they are not replaced when injured or otherwise lost. In humans, the corneal endothelial cell layer is most densely packed at birth and cell density thereafter decreases rapidly as the eyes grow (reflecting the same number of cells covering a larger area). Thereafter, corneal cell density gradually declines with age, apparently reflecting the gradual loss of cells which are not replaced. As cell density decreases, each cell spreads out and covers a larger area to maintain the cell layer's barrier and pump functions. However, once the cell density drops too low (lower than about 500 to 1000 cells/mm$^2$) its function is compromised, resulting in corneal clouding, stromal edema, loss of visual acuity and eventual blindness. Specifically, the cell density of tightly packed corneal endothelium in vivo has been reported to be as high as 5624 cells/mm$^2$ in infants two months of age, falling to 4252 cells/mm$^2$ within the first year from birth, and subsequently decreasing rapidly during early childhood (associated with the increase in corneal size as eyes grow). By 5 years of age, corneal endothelium density falls to approximately 3591 plus or minus 399 cells/mm$^2$, and falls farther to approximately 2697 plus or minus 246 cells/mm$^2$ by 10 years of age, and further declines by approximately 0.6% per year throughout adulthood. See Peh et al., Transplantation. 2011 Apr. 27; 91(8):811-9.

Primary diseases that affect the corneal endothelium include Fuch's dystrophy, iridocorneal endothelial syndrome, posterior polymorphous dystrophy, and congenital hereditary endothelial dystrophy. Secondary diseases for which the most effective treatment is replacement of the corneal endothelium include several corneal dystrophies, contact lens usage, cataract surgery, and late endothelial failure in cornea transplantation. The preferred treatment when only the corneal endothelium is compromised is Descemet's stripping with endothelial keratoplasty (DSEK), which includes the removal of Descemet's membrane and the corneal endothelium, and subsequent transplantation of donor tissue. Alternatively, in penetrating keratoplasty (PKP) the entire cornea is removed and replaced.

Generally, corneal transplantation includes obtaining a donor cornea (e.g., from a post-mortem anatomical gift), determining whether the donor cornea is of sufficient quality and otherwise suitable for use, and surgical replacement of the damaged or diseased cornea. Procedures have been developed to replace the entire cornea (penetrating keratoplasty) or leave the patient's Descemet's membrane and endothelium and replace the remaining layers with donated tissue (lamellar keratoplasty); the latter procedure may decrease the risk of transplant rejection but may also give inferior visual acuity post-transplant. Additionally, lamellar keratoplasty may not be suitable for treatment of some conditions for which replacement of the patient's corneal endothelium and/or Descemet's membrane may be the indicated treatment. See, generally, U.S. Pat. No. 5,755,785, U.S. Pat. No. 5,649,944, U.S. Pat. No. 7,147,648, U.S. Pat. No. 7,300,653, U.S. Pat. No. 5,584,881, U.S. Pat. No. 5,686,414, U.S. Pat. No. 7,300,654, U.S. patent application Ser. No. 10/525,391, each of which is incorporated by reference in its entirety. Additional methods of corneal endothelial surgical replacement are under development, including Descemet's Membrane Endothelial Keratoplasty (DMEK), in which the donor tissue consists only of Descemet's membrane and corneal endothelium. Another potentially promising therapeutic avenue is corneal endothelial reconstruction, in which corneal endothelial cells are cultured in vitro prior to transplantation. For example, donated human corneal cells were cultured on a polymer, released onto a bioadhesive gelatin disc, and then successfully integrated into denuded rabbit corneas, with the gelatin disc dissolving after transplantation (Hsiue et al., Transplantation. 2006 Feb. 15; 81(3):473-6, which is incorporated by reference herein in its entirety). However, methods utilizing culture cells presuppose a source of said cells, and thus are affected by the shortage of suitable donated tissues as described above. Additionally, due to differences among donated cells, it may prove difficult to produce corneal endothelial cell cultures of consistent quality and efficacy. Regulatory hurdles may also make such methods logistically difficult to perform on a large scale, due to the possibility that extensive testing for safety and/or efficacy may be required for the cells obtained from each donor. These and additional therapeutic methods are further described in Thomas John, Corneal Endothelial Transplant: DSAEK, DMEK & DLEK (JP Medical Ltd, 2010), which is incorporated by reference herein in its entirety.

Additional disclosures generally related to methods of obtaining and using corneal cells, including therapeutic methods, culture methods, preservation methods, compositions containing or that may be used in conjunction therewith, and the like are included in U.S. 2007/0275365, US 2010/0209402, US 2010/0233240, US 2011/0009488, US 2009/0232772, U.S. Pat. No. 5,166,048, US 2007/0092550, US 2005/0214259, US 2007/0148137, U.S. Pat. No. 4,959,319, U.S. Pat. No. 5,310,728, U.S. Pat. No. 5,589,451, US 2010/0215717, U.S. Pat. No. 5,703,047, US 2009/0222086, US 2009/0263465, US 2006/0228693, US 2006/0240552, US 2009/0270982, U.S. Pat. No. 5,269,812, U.S. Pat. No. 7,371,513, US 2010/0069915, and US 2011/0166650, each of which is incorporated by reference herein in its entirety.

SUMMARY

It may be one object of the present disclosure to provide a method of producing corneal endothelial cells (CEC), which may comprise (a) contacting neural crest stem cells (NCSCs) with at least one factor that induces differentiation of said neural crest cells into CEC.

The at least one factor that induces differentiation of said neural crest cells into CEC may comprise at least one DKK2 agonist and/or at least one PDGFB agonist.

The at least one DKK2 agonist may include a factor selected from the group consisting of: LRP5/6 antagonists; Kremen antagonists; Dkk 1; Dkk 3; Dkk 4; Soggy; secreted frizzled related proteins (Frzb); Wnt inhibitor factor (WIF); a Wnt modulator; Casein Kinase 1-7β catenin antagonists; LEF/TCF transcription factor members modulators; IWR; pyrvinium; ICG-001; PKF115-584; IWP; Ant1.4Br/Ant 1.4Cl; Niclosamide; apicularen; bafilomycin; XAV939; NSC668036; 2,4-diamino-quinazoline; Quercetin; and any combination thereof.

The at least one DKK2 agonist may include a factor selected from the group consisting of: Wnt proteins, nucleic acids encoding Wnt proteins, LiCl, Axin antagonists; APC antagonists; norrin; R-spondin2; (hetero)arylpyrimidines; IQ1; BIO(6-bromoindirubin-3'-oxime); 2-amino-4-[3,4-(methylenedioxy)benzyl-amino]-6-(3-methoxyphenyl)pyrimidine; a Wnt modulator; WAY-316606; QS11; SB-216763; SB-216763; DCA; and any combination thereof.

The at least one PDGFB agonist may include a factor selected from the group consisting of: a PDGFRβ agonist, a PKC pathway agonist, PDGFAA polypeptide, a nucleic acid encoding PDGFAA, PDGFAB polypeptide, a nucleic acid encoding PDGFAB, Phorbol 12-myristate 13-acetate (PMA), VEGF, and any combination thereof.

The at least one factor that induces differentiation of said neural crest cells into CEC may comprise at least one DKK2 agonist and at least one PDGFB agonist.

The at least one DKK2 agonist may comprise DKK2 polypeptide.

The at least one PDGFB agonist may comprise PDGFB polypeptide.

The at least one DKK2 agonist may comprise DKK2 polypeptide and said at least one PDGFB agonist may comprise PDGFB polypeptide.

The concentration of said DKK2 polypeptide may be between 1 ng/ml and 15 µg/ml, between 10 ng/ml and 15 µg/ml, between 1 ng/ml and 1 µg/ml, between 1 ng/ml and 100 ng/ml, between 2 ng/ml and 20 ng/ml, between 5 ng/ml and 20 ng/ml, or about 10 ng/ml.

The concentration of said PDGFB polypeptide may be between 0.1 ng/ml and 250 ng/ml, between 0.5 ng/ml and 150 ng/ml, between 1 ng/ml and 50 ng/ml, between 2 ng/ml and 20 ng/ml, or about 10 ng/ml.

The method may comprise culturing said CEC on a matrix.

The matrix may be selected from the group consisting of: laminin, fibronectin, vitronectin, proteoglycan, entactin, collagen, collagen I, collagen IV, collagen VIII, heparan sulfate, Matrigel (a soluble preparation from Engelbreth-Holm-Swarm (EHS) mouse sarcoma cells), a human basement membrane extract, and any combination thereof.

The matrix may be of human or non-human animal origin.

The matrix may be of bovine, mouse or rat origin.

The matrix may comprise Matrigel.

The subsequent to commencement of step (a), said cells may be passaged.

The passaging may be effected between 1 hour and 5 days, between 2 hours and 4 days, between 3 hours and 3 days, between 4 hours and 2 days, or about 1 day subsequent to commencement of step (a).

The passaging may be effected by a method which may comprise contacting the cells with a cell dissociation buffer, or by a method which may comprise mechanical dissociation of the cells or a subset thereof, or by a method which may comprise optical isolation the cells or a subset thereof.

The cell dissociation buffer may be non-enzymatic.

The cell dissociation buffer may comprise ethylenediaminetetraacetic acid (EDTA).

The duration of said contacting NCSCs with a factor that induces differentiation of said neural crest cells into CEC may be at least 2 days, between 2 and 25 days, or may be between 2 and 10 days.

In another exemplary embodiment, the CEC may be purified using affinity-based depletion of other cell types, which may be effected concurrently with passaging or at an earlier or later time. Depletion methods may utilize a binding molecule having affinity for a marker of a non-CEC cell type, e.g., an antibody or fragment thereof, which may be directly or indirectly coupled to a bead or other substrate, such as a magnetic microbead. For example, a substrate may be coupled to one or more antibodies that can deplete stem cells or fibroblasts. Exemplary markers that may be utilized include CD271, SSEA-1, TRA-1-60, SSEA-4, and/or CD326. Potentially suitable commercially available reagents include Anti-SSEA-1 MicroBeads (Miltenyi Biotech, cat#130-094-530), Anti-TRA-1-60 MicroBead Kit (Miltenyi Biotech, cat#130-095-816), Anti-SSEA-4 MicroBeads (Miltenyi Biotech, cat#130-097-855), and Anti-fibroblast CD326 (Miltenyi Biotech, cat#130-050-601).

Step (a) further may comprise culturing said NCSCs on a matrix, which may be selected from the group consisting of: laminin, fibronectin, vitronectin, proteoglycan, entactin, collagen, collagen I, collagen IV, collagen VIII, heparan sulfate, Matrigel (a soluble preparation from Engelbreth-Holm-Swarm (EHS) mouse sarcoma cells), a human basement membrane extract, and any combination thereof, may be of human or non-human animal origin, may be of bovine, mouse or rat origin, or may comprise Matrigel.

The NCSCs may be obtained from an animal tissue, which may be selected from the group consisting of: the gut, dorsal root ganglia, bone marrow, skin, heart, cornea, caratoid body, neural tube, teeth, and sciatic nerve. The animal tissue may be human tissue.

The NCSCs may be produced by transdifferentiation of a somatic cell.

The NCSCs may be obtained from cultures of neural rosettes.

The neural crest stem cells may be produced from ES cells by a method which may comprise culturing ES cells with MS5 stromal feeder cells.

The NCSCs may be produced from ES cells.

The neural crest stem cells may be produced from ES cells by a method which may comprise contacting ES cells with one or more inhibitors of SMA/Mothers Against Decapentaplegic (SMAD) protein signaling.

The one or more inhibitors of SMAD protein signaling may prevent the binding of a TGF-β family ligands to its corresponding receptor.

The one or more inhibitors of SMAD protein signaling may prevent the activation of a TGF-β receptor.

The one or more inhibitors of SMAD protein signaling inhibits one or more SMAD intracellular proteins/transcription factors.

The one or more inhibitors of SMAD protein signaling may comprise Leukemia Inhibitory Factor (LIF), GSK3 inhibitor (CHIR 99021), Compound E (γ secretase inhibitor XXI), SB431542, or any combination thereof.

The one or more inhibitors of SMAD protein signaling may comprise Chordin, Follistatin, dominant negative receptors or blocking antibodies that sequester BMP2, BMP4, and/or BMP7, dorsomorphin (or Compound C), SIS3 (6,7-Dimethoxy-2-((2E)-3-(1-methyl-2-phenyl-1H-pyrrolo[2,3-b]pyridin-3-yl-prop-2-enoyl))-1,2,3,4-tetrahydroisoquinoline, Specific Inhibitor of Smad3 (SIS3), an inhibitor SMAD, SMAD6, SMAD7, SMAD10, an antagonist of a receptor SMAD, an antagonist of SMAD1, an antagonist of SMAD2, an antagonist of SMAD3, an antagonist of SMAD5, an antagonist of SMAD8/9, or any combination thereof.

The duration of said contacting ES cells with one or more inhibitors of SMAD protein signaling may be at least 2 days, between 1 and 10 days, or may be between 2 and 6 days.

The neural crest stem cells may be produced from ES cells by a method further which may comprise contacting ES cells with at least one Wnt agonist.

The neural crest stem cells may be produced from ES cells by a method further which may comprise contacting ES cells with at least one Wnt agonist which may comprise (2'Z, 3'E)-6-bromoindirubin-3'-oxime (BIO) and/or Wnt3a.

The neural crest stem cells may be produced from ES cells by a method further which may comprise contacting ES cells with at least one Wnt agonist selected from the group consisting of: Wnt proteins, nucleic acids encoding Wnt proteins, LiCl, Axin antagonists; APC antagonists; norrin; R-spondin2; (hetero)arylpyrimidines; IQ1; BIO(6-bromoindirubin-3'-oxime); 2-amino-4-[3,4-(methylenedioxy)benzyl-amino]-6-(3-methoxyphenyl)pyrimidine; WAY-316606; QS11; SB-216763; SB-216763; DCA; and any combination thereof.

The neural crest stem cells may be produced from ES cells by a method which may comprise contacting ES cells with a first inhibitor of SMAD protein signaling and a second inhibitor of SMAD protein signaling.

The first inhibitor of SMAD protein signaling may be selected from the group consisting of: Noggin polypeptide, dorsomorphin, LDN-193189, and any combination thereof.

The first inhibitor of SMAD protein may comprise Noggin polypeptide.

The Noggin polypeptide may be present in a concentration between 10 ng/ml and 5,000 ng/ml, between 100 ng/ml and 700 ng/ml, between 400 ng/ml and 600 ng/ml, or about 500 ng/ml.

The first inhibitor of SMAD protein signaling may be selected from the group consisting of: antagonists of BMP2; antagonists of BMP4; antagonists of BMP7; and antagonists of TGFβ;

The second inhibitor of SMAD protein signaling may comprise an inhibitor of an anaplastic lymphoma kinase signaling pathway.

The second inhibitor of SMAD protein signaling inhibits a signaling pathway selected from the group consisting of Lefty, Activin, and TGFbeta.

The second inhibitor of SMAD protein signaling inhibits both activin and nodal signaling.

The second inhibitor of SMAD protein signaling inhibits the Lefty/Activin/TGFbeta pathways by blocking phosphorylation of the ALK4, ALK5 and ALK7 receptors.

The second inhibitor of SMAD protein signaling may be an ALK4 receptor inhibitor.

The second inhibitor of SMAD protein signaling may be selected from the group consisting of: 4-[4-(1,3-benzodioxol-5-yl)-5-(2-pyridinyl)-1H-imidazol-2-yl]benzamide (SB431542) and derivatives thereof.

The second inhibitor of SMAD protein signaling may comprise SB431542.

The SB431542 may be present in a concentration between 10 nM and 100 μM, between 0.1 μM and 50 μM, between 0.1 and 20 μM, between 1 and 20 μM, or about 10 μM.

The second inhibitor of SMAD protein signaling blocks phosphorylation of ACTRIB, TGFβR1, and ACTRIC receptors.

The second inhibitor of SMAD protein signaling inhibits TGFβ/Activin/Nodal signaling.

The second inhibitor of SMAD protein signaling blocks endogenous Activin and BMP signals.

The first inhibitor of SMAD protein signaling and/or said second inhibitor of SMAD protein signaling may be each selected from the group consisting of: Chordin, Follistatin, dominant negative receptors or blocking antibodies that sequester BMP2, BMP4, and/or BMP7, dorsomorphin (or Compound C), SIS3 (6,7-Dimethoxy-2-((2E)-3-(1-methyl-2-phenyl-1H-pyrrolo[2,3-b]pyridin-3-yl-prop-2-enoyl))-1,2,3,4-tetrahydroisoquinoline, Specific Inhibitor of Smad3 (SIS3), an inhibitor SMAD, SMAD6, SMAD7, SMAD10, an antagonist of a receptor SMAD, an antagonist of SMAD1, an antagonist of SMAD2, an antagonist of SMAD3, an antagonist of SMAD5, and an antagonist of SMAD8/9.

The first inhibitor of SMAD protein signaling may comprise Noggin and said second inhibitor of SMAD protein signaling may comprise SB431542.

The duration of said contacting ES cells with said first inhibitor of SMAD protein signaling and said second inhibitor of SMAD protein signaling may be at least 2 days, between 1 and 10 days, or may be between 2 and 6 days.

The ES cells may be human ES cells.

The ES cells may be iPS cells.

The ES cells may not exhibit changes or mutations in genes associated with a disease of corneal endothelial cells.

The ES cells may exhibit a normal karyotype.

Prior to differentiation into NCSCs, said ES cells may be maintained in culture in the absence of feeder cells.

Prior to differentiation into NCSCs said ES cells may be cultured on a matrix, which may be selected from the group consisting of: laminin, fibronectin, vitronectin, proteoglycan, entactin, collagen, collagen I, collagen IV, heparan sulfate, Matrigel (a soluble preparation from Engelbreth-Holm-Swarm (EHS) mouse sarcoma cells), a human basement membrane extract, and any combination thereof, or may be of human or non-human animal origin, or may be of bovine, mouse or rat origin, or may comprise Matrigel.

The NCSCs may express one or more markers selected from the group consisting of: Sox10, AP2, HNK1, PAX7, p75 (NGFR), and any combination thereof.

The CEC may express one or more markers selected from the group consisting of: Na+/K+ ATPase, ZO-1, KLF13, AQP1, Collagen VIII, SLC16A3, CFTR, NBC1, CA2, AE2/SCL4A2, SCL16A1, CA12, CA4, FoxC1, and any combination thereof.

The CEC may express the markers Collagen VIII, Na+K+ ATPase pump, and ZO-1, and may not express the markers vWF and CD31.

The CEC may express one or more corneal endothelial pump markers.

The CEC may express one or more periocular neural crest markers.

The CEC may express one or more cell adhesion and matrix proteins.

The CEC may express at least one corneal endothelial pump marker, at least one periocular neural crest marker, and at least one cell adhesion and matrix protein.

The one or more corneal endothelial pump markers may be selected from the group consisting of: AQP1, CA2, CA4, CA12, SCL14A2, SLC16A1, SLC16A3, SLC16A7, CFTR, NHE1, ADCY10, voltage-dependent anion channels VDAC2 and VDAC3, chloride channel proteins CLCN2 and CLC.

The periocular neural crest markers may be selected from the group consisting of: PITX2, and FOXC1.

The cell adhesion and matrix proteins may be selected from the group consisting of: Occludin, Connexin 43, 9.3E antigen, Collagen III, Collagen IV, N cadherin, VE cadherin, E cadherin, beta catenin, p120, p190 Laminin alpha 4, Nidogen-2, and Netrin 4.

The CEC may express the markers Collagen VIII, Na+K+ ATPase pump, AQP1, CA2, CA4, CA12, SCL14A2, SLC16A1, SLC16A3, SLC16A7, CFTR, NHE1, ADCY10, PITX2, and FOXC1, and may not express the markers vWF and CD31.

The CEC may form a monolayer of uniformly sized cells with a predominantly hexagonal shape, such as at least 50%, at least 60%, at least 70%, at least 80%, or at least 90% of said CEC may exhibit said hexagonal shape.

The CEC may allow unidirectional leakage of solutes and nutrients.

The CEC may actively pump water in the opposite direction of said unidirectional leakage.

The CEC may exhibit a high level of metabolic activity that may be comparable to animal-derived CEC.

The CEC may be human CEC.

The CEC may exhibit a culture density of at least 1000 cells/mm$^2$, at least 2000 cells/mm$^2$, at least 3000 cells/mm$^2$, at least 4000 cells/mm$^2$, at least 5000 cells/mm$^2$, at least 6000 cells/mm$^2$, at least 7000 cells/mm$^2$, at least 8000 cells/mm$^2$, at least 9000 cells/mm$^2$, between 2000 and 9000 cells/mm$^2$ between 2000 and 8000 cells/mm$^2$ between 2000 and 7000 cells/mm$^2$, between 2000 and 6000 cells/mm$^2$, between 2000 and 5,000 cells/mm$^2$, between 2000 and 4000 cells/mm$^2$, between 2000 and 3500 cells/mm$^2$, or about 2500 cells/mm$^2$.

The CEC may exhibit a decreased level of accumulated oxidative stress and/or DNA damage compared to CEC isolated from a living host.

The level of oxidative stress and/or DNA damage may be detected by measuring the quantity of one or more of: nuclear DNA damage foci; level of expression of p21Cip1, level of expression of p16INK4a; level of expression of cytoglobin protein, level of expression of GPX-1 protein, and level of 8-hydroxy-2_-deoxyguanosine (8-OHdG).

The CEC may comprise at least 50%, at least 60%, at least 70%, at least 80%, or at least 90% of the cells in the resulting culture.

In another aspect, the present disclosure provides a composition comprising corneal endothelial cells (CEC) produced according to any method as described herein.

In another aspect, the present disclosure provides a composition comprising a sheet of CEC having a culture density of at least 1000 cells/mm$^2$, at least 2000 cells/mm$^2$, between 2000 and 6000 cells/mm$^2$, between 2000 and 5,000 cells/mm$^2$, between 2000 and 4000 cells/mm$^2$, between 2000 and 3500 cells/mm$^2$, or about 2500 cells/mm$^2$.

In another aspect, the present disclosure provides a composition comprising CEC that exhibit a decreased level of accumulated oxidative stress and/or DNA damage compared to CEC isolated from a living host.

In another aspect, the present disclosure provides a composition comprising corneal endothelial cells (CEC) produced from neural crest stem cells (NCSCs).

The NCSCs may be produced from embryonic stem (ES) cells.

The NCSCs may be produced from ES cells by a method which may comprise contacting said ES cells with one or more inhibitors of SMAD signaling.

In another aspect, the present disclosure provides a composition comprising corneal endothelial cells (CEC) produced from embryonic stem (ES) cells.

The ES cells may be human ES cells.

The ES cells may be iPS cells.

The ES cells may not exhibit changes or mutations in genes associated with a disease of corneal endothelial cells.

The ES cells may exhibit a normal karyotype.

Prior to differentiation into NCSCs, said ES cells may be maintained in culture in the absence of feeder cells.

Prior to differentiation into NCSCs said ES cells may be cultured on a matrix, such as a matrix may be selected from the group consisting of: laminin, fibronectin, vitronectin, proteoglycan, entactin, collagen, collagen I, collagen IV, heparan sulfate, Matrigel (a soluble preparation from Engelbreth-Holm-Swarm (EHS) mouse sarcoma cells), a human basement membrane extract, and any combination thereof, which may be of human or non-human animal origin, such as bovine, mouse or rat origin, or Matrigel.

The NCSCs may express one or more markers selected from the group consisting of: Sox10, AP2, HNK1, PAX7, p75 (NGFR), and any combination thereof.

The CEC may express one or more markers selected from the group consisting of: Na+/K+ ATPase, ZO-1, KLF13, AQP1, Collagen VIII, SLC16A3, CFTR, NBC1, CA2, AE2/SCL4A2, SCL16A1, CA12, CA4, FoxC1, and any combination thereof.

The CEC may express the markers Collagen VIII, Na+K+ ATPase pump, and ZO-1, and may not express the markers vWF and CD31.

The CEC may express one or more corneal endothelial pump markers.

The CEC may express one or more periocular neural crest markers.

The CEC may express one or more cell adhesion and matrix proteins.

The CEC may express at least one corneal endothelial pump marker, at least one periocular neural crest marker, and at least one cell adhesion and matrix protein.

The one or more corneal endothelial pump markers may be selected from the group consisting of: AQP1, CA2, CA4, CA12, SCL14A2, SLC16A, SLC16A3, SLC16A7, CFTR, NHE1, ADCY10, voltage-dependent anion channels VDAC2 and VDAC3, chloride channel proteins CLCN2 and CLC.

The periocular neural crest markers may be selected from the group consisting of: PITX2, and FOXC1.

The cell adhesion and matrix proteins may be selected from the group consisting of: Occludin, Connexin 43, 9.3E antigen, Collagen III, Collagen IV, N cadherin, VE cadherin, E cadherin, beta catenin, p120, p190 Laminin alpha 4, Nidogen-2, and Netrin 4.

The CEC may express the markers Collagen VIII, Na+K+ ATPase pump, AQP1, CA2, CA4, CA12, SCL14A2, SLC16A1, SLC16A3, SLC16A7, CFTR, NHE1, ADCY10, PITX2, and FOXC1, and may not express the markers vWF and CD31.

The CEC may form a monolayer of uniformly sized cells with a predominantly hexagonal shape, such as at least 50%, at least 60%, at least 70%, at least 80%, or at least 90% of said CEC may exhibit said hexagonal shape.

The CEC may allow unidirectional leakage of solutes and nutrients.

The CEC may actively pump water in the opposite direction of said unidirectional leakage.

The CEC may exhibit a high level of metabolic activity that may be comparable to animal-derived CEC.

The CEC may be human CEC.

The CEC may exhibit a culture density of at least 1000 cells/mm$^2$, at least 2000 cells/mm$^2$, at least 3000 cells/mm$^2$, at least 4000 cells/mm$^2$, at least 5000 cells/mm$^2$, at least 6000 cells/mm$^2$, at least 7000 cells/mm$^2$, at least 8000 cells/mm$^2$, at least 9000 cells/mm$^2$, between 2000 and 9000 cells/mm$^2$ between 2000 and 8000 cells/mm$^2$ between 2000 and 7000 cells/mm$^2$, between 2000 and 6000 cells/mm$^2$, between 2000 and 5,000 cells/mm$^2$, between 2000 and 4000 cells/mm$^2$, between 2000 and 3500 cells/mm$^2$, or about 2500 cells/mm$^2$.

The CEC may exhibit a decreased level of accumulated oxidative stress and/or DNA damage compared to CEC isolated from a living host, which may for example be detected by measuring the quantity of one or more of: nuclear DNA damage foci; level of expression of p21Cip1, level of expression of p16INK4a; level of expression of cytoglobin protein, level of expression of GPX-1 protein, and level of 8-hydroxy-2_-deoxyguanosine (8-OHdG).

The CEC may comprise at least 50%, at least 60%, at least 70%, at least 80%, or at least 90% of the cells in the culture in which they are contained.

The CEC may be contained in a sheet of CEC.

The sheet of cells may comprise or consists essentially of an approximately circular disc of cells having a diameter of at least 1, 2, 3, 4, 5, 6, 7, 8, 9, 10, 11, or 12 mm.

The CEC may exhibit a culture density of at least 1000 cells/mm$^2$, at least 2000 cells/mm$^2$, at least 3000 cells/mm$^2$, at least 4000 cells/mm$^2$, at least 5000 cells/mm$^2$, at least 6000 cells/mm$^2$, at least 7000 cells/mm$^2$, at least 8000 cells/mm$^2$, at least 9000 cells/mm$^2$, between 2000 and 9000 cells/mm$^2$ between 2000 and 8000 cells/mm$^2$ between 2000 and 7000 cells/mm$^2$, between 2000 and 6000 cells/mm$^2$, between 2000 and 5,000 cells/mm$^2$, between 2000 and 4000 cells/mm$^2$, between 2000 and 3500 cells/mm$^2$, or about 2500 cells/mm$^2$.

The total number of cells (for example in a sheet or dissociated cells) may be between about 800 and about 800,000 cells, e.g., at least about 10,000, at least about 20,000, at least about 50,000, at least about 100,000, at least about 200,000, at least about 300,000, at least about 400,000, at least about 500,000, at least about 600,000 or at least about 700,000 cells, such between about 100,000 and about 800,000 cells, between about 150,000 cells and about 675,000 cells, between about 250,000 cells and about 550,000 cells, as well as other numerical ranges within these values.

The CEC may be situated on a carrier.

The CEC may be cultured on a substrate and released onto a carrier.

The substrate may comprise a thermoresponsive polymer or a thermoresponsive poly(N-isopropylacrylamide) (PNI-PAAm)-grafted surface.

The carrier may comprise gelatin, fibrin-based matrixes, endothelium-denuded corneal buttons, denuded Descemet's membrane, devitalized stromal cornea, fresh corneal stromal discs, and/or an amniotic membrane.

The CEC may be in suspension.

The composition may further comprise an inhibitor of Rho-associated kinase (ROCK).

The inhibitor of Rho-associated kinase may comprise Y-27632.

The CEC may exhibit a decreased level of accumulated oxidative stress and/or DNA damage compared to CEC isolated from a living host, which may for example be detected by measuring the quantity of one or more of: nuclear DNA damage foci; level of expression of p21Cip1, level of expression of p16INK4a; level of expression of cytoglobin protein, level of expression of GPX-1 protein, and level of 8-hydroxy-2_-deoxyguanosine (8-OHdG).

The composition may comprise at least 2000, at least 3000, at least 8000, at least 1000, at least 18000, at least 25000, at least 31000, at least 44000, at least 49000, at least 69000, at least 71000, at least 96000, at least 99000, at least 126000, at least 135000, at least 159000, at least 176000, at least 196000, at least 223000, at least 275000, at least 237000, at least 283000, at least 332000, or at least 396000 CEC.

The composition may comprise at least 50%, at least 60%, at least 70%, at least 80%, or at least 90% CEC.

The composition may further comprise a pharmaceutically acceptable excipient.

The composition may further comprise an immunosuppressive or immune tolerizing agent.

The immunosuppressive or immune tolerizing agent may comprise one or more of: mesenchymal stem cells, anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, tacrolimus, mycophemolate mofetil, and corticosteroids.

The composition may be free of detectable bacterial contaminants, mycoplasmal contaminants, and viruses.

The composition may comprise human CEC.

The composition may be suitable for transplantation into the eye of a patient in need thereof, such as a human patient.

The composition may be used in the manufacture of a medicament.

The medicament may be for the treatment of a disease of corneal endothelial cells.

The disease of corneal endothelial cells may comprise Fuch's dystrophy, iridocorneal endothelial syndrome, posterior polymorphous dystrophy, or congenital hereditary endothelial dystrophy, and/or secondary diseases for which an effective treatment may be replacement of the corneal endothelium including corneal dystrophies, contact lens usage, cataract surgery, and late endothelial failure in cornea transplantation.

The disease of corneal endothelial cells may comprise pleomorphism, a significant disruption in the regular hexagonal pattern of the endothelium that can cause a decrease in endothelial mosaic stability. Pleomorphism may occur secondary to another disease of the cornea, such as physiological stress from ocular disease, contact lens wear or normal aging changes.

The medicament may be adapted for administration by a method which may comprise Descemet's stripping with endothelial keratoplasty (DSEK), Penetrating Keratoplasty (PKP), lamellar keratoplasty, Descemet's Membrane Endothelial Keratoplasty (DMEK), DSAEK, and DLEK.

In a further aspect, the disclosure provides a method of treatment of a disease of corneal endothelial cells or injured corneal endothelial cells, which may comprise administering a composition comprising CEC to a patient in need thereof.

The CEC may be administered by a method which may comprise Descemet's stripping with endothelial keratoplasty (DSEK), Penetrating Keratoplasty (PKP), lamellar keratoplasty, Descemet's Membrane Endothelial Keratoplasty (DMEK), DSAEK, DMEK and DLEK.

The disease of corneal endothelial cells may be selected from the group consisting of: Fuch's dystrophy, iridocorneal endothelial syndrome, posterior polymorphous dystrophy, and congenital hereditary endothelial dystrophy, and secondary diseases for which an effective treatment may be replacement of the corneal endothelium including corneal dystrophies, contact lens usage, cataract surgery, and late endothelial failure in cornea transplantation.

The method of treatment may comprise administering an immunosuppressive agent or immune tolerizing agent to said patient.

The immunosuppressive agent or immune tolerizing agent may be administered in an amount sufficient to reduce the risk of rejection of said CEC.

The immunosuppressive agent or immune tolerizing agent may be administered prior to, concurrently with, and/or subsequent to administration of said CEC to said patient.

The composition comprising CEC further may comprise an immunosuppressive agent or immune tolerizing agent.

The immunosuppressive or immune tolerizing agent may comprise one or more of: mesenchymal stem cells, anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, tacrolimus, mycophemolate mofetil, and corticosteroids.

BRIEF DESCRIPTION OF THE DRAWINGS

FIG. 1A schematically illustrates two methods that were used to generate corneal endothelial cells from embryonic stem cells. FIG. 1B is a phase micrograph showing a circular field of hES-derived corneal endothelium (outlined by a dashed circle), which were identifiable by their hexagonal morphology (Hex). The circular field of corneal endothelium was surrounded by non-hexagonal cells (P) which were thought to include progenitor cells that had not adopted a hexagonal corneal morphology. The corneal endothelial cells in FIG. 1B were generated from hESCs using the method described in Example 1 and are shown at day 9. FIG. 1C is a micrograph showing a field of hESC-derived corneal endothelium (Hex) that was generated using the method described in Example 2 (i.e., with the passaging step). Relative to the method described in Example 1, the Method described in Example 2 produced a greater proportion of corneal endothelial cells, with small patches of non-hexagonal cells (P) present among the corneal endothelial cells.

FIG. 2A shows cell populations produced using the method described in Example 1, in which at day 9, corneal endothelial cells formed circular colonies (arrow), with isolated corneal endothelial cells also present outside of the circular colonies (4× magnification). FIG. 2B shows representative cells derived using the method described in Example 1 at higher magnification (20×) to illustrate the hexagonal or polygonal shape indicative of endothelial cells (arrow). FIG. 2C shows cell populations produced as described in Example 2, in which at day 10, culture corneal endothelial cells were predominant in the culture (4× magnification). FIG. 2D shows representative cells derived as described in Example 2 at higher magnification (20×) to illustrate the hexagonal or polygonal shape indicative of endothelial cells (arrow).

FIG. 3A, 10×; FIG. 3D, 40×) and using the nuclear stain DAPI (blue; FIG. 3B, 10×; FIG. 3E, 40×). ZO-1 exhibited a polygonal or hexagonal localization consistent with the expected staining of tight junctions. Merged views (FIG. 3C, 10×; FIG. 3F, 40×) demonstrate the expected spatial relationship between ZO-1 and DAPI staining, i.e., generally a single nucleus contained within each polygonal or hexagonal ZO-1 stained cell. The corneal endothelial cells in this figure were produced using the method described in Example 1 and are shown at day 9.

FIG. 4B, DAPI staining shown in blue; FIG. 4C, merged view of panels A and B). By contrast, CEC (differentiated from the hESC line H1GFP) exhibited a localized distribution of Na+K+ATPase (FIG. 4D, Na+K+ATPase staining shown in red; FIG. 4E, DAPI staining shown in blue; FIG. 4F, merged view of panels D and E). The Na+K+ATPase staining in the CEC exhibited a polygonal or hexagonal localization consistent with the expected staining of tight junctions, generally with a single nucleus within each cell. The corneal endothelial cells in this figure were produced as described in Example 1 and are shown at day 9.

FIG. 10 shows expression of the transcription factors PITX2 and FOXC1 (markers of ocular neural crest) at day 9 of induction of corneal endothelial cell differentiation using the method as described in Example 1. RQ indicates quantity detected relative to the amount detected from hESCs and the endogenous control PGK1, i.e., the level of expression in hESC is set to 1. RQ values shown are the average of multiple measurements, with error bars indicating the minimum and maximum of the RQ).

FIG. 16. Many corneal endothelial pumps are upregulated over 1-4 weeks of culture. All samples were normalized to stem cells (hESC). "PD1T" indicates cells produced as in Example 2, i.e. with the replating step during differentiation. A. Expression of upregulated pumps over time. B. Corneal endothelial pump markers that are present, but not at increased levels compared to hESC. C. Expression of COL8A2 is lower than the related gene, COL8A1.

FIG. 17. Rock inhibitor improves morphology of hESC CEC after harvesting and replating and changes levels of corneal endothelial genes by QPCR. A-D. Phase contrast pictures of hESC CEC cells that have been trypsinized and then replated in the presence of Rock inhibitor. A. The morphology of the hESC CEC is variable with the presence of 1 µM Rock inhibitor. B. The hESC CEC are somewhat more uniform with 5 µM Rock inhibitor. C. The hESC CEC are uniform and polygonal/hexagonal with 10 µM Rock inhibitor. D. The hESC CEC are uniform and polygonal/hexagonal with 20 µM Rock inhibitor. E-F. All samples were normalized to stem cells (hESC). E. COL8A1 expression is relatively unchanged with the presence of Rock inhibitor compared to PD1T that has not been harvested. SLC16A3 is upregulated for 1-10 µM Rock inhibitor, but unchanged for 20 µM Rock inhibitor, compared to PD1T that has not been harvested. ("PD1T" indicates cells produced as in Example 2, i.e. with the replating step during differentiation.)

FIG. 20. Global comparison of gene expression between hESC CEC and adult-derived CEC. The genes shown exhibited at least a 3-fold difference in expression between hESC CEC and Adult CEC at a significance threshold of $p<0.05$. Gene symbol, gene description, accession number, and fold difference are listed for each gene. The microarray additionally included positions which were not annotated and the results for these positions is included in the able with the designation "Tr." (e.g., "Tr. 7904959") indicating the expression result for the specified Transcripts Cluster Id on the array. A negative value indicates that the expression is lower in the adult CEC compared to the hESC CEC.

FIG. 21. Improved purity of hESC-derived CEC using magnetic bead subtraction. CD271+ positive cells were removed from corneal endothelial cultures. Phase contrast (20×) view of cells that have been cultured for a total of 2 weeks of differentiation. A. Control cells produced as in Example 2 but not passaged at Day 10. B. Control for CD271 subtraction. Cells were trypsinized on Day 10 and immediately replated. C. The majority of the CD271+ cells were removed by magnetic bead separation. The processing of the cells has altered the morphology of the corneal endothelial cells. D. Flow Cytometry analysis of CD271+ cells on unsorted by magnetic beads. Approximately 23% of all cells expressed CD271 at relatively low levels. E. CD271+ cells were depleted by magnetic bead separation. FLA4 is the APC channel where CD271 was detected. CD271 is also known as neural crest gene NGFR.

DETAILED DESCRIPTION

Figure 2:
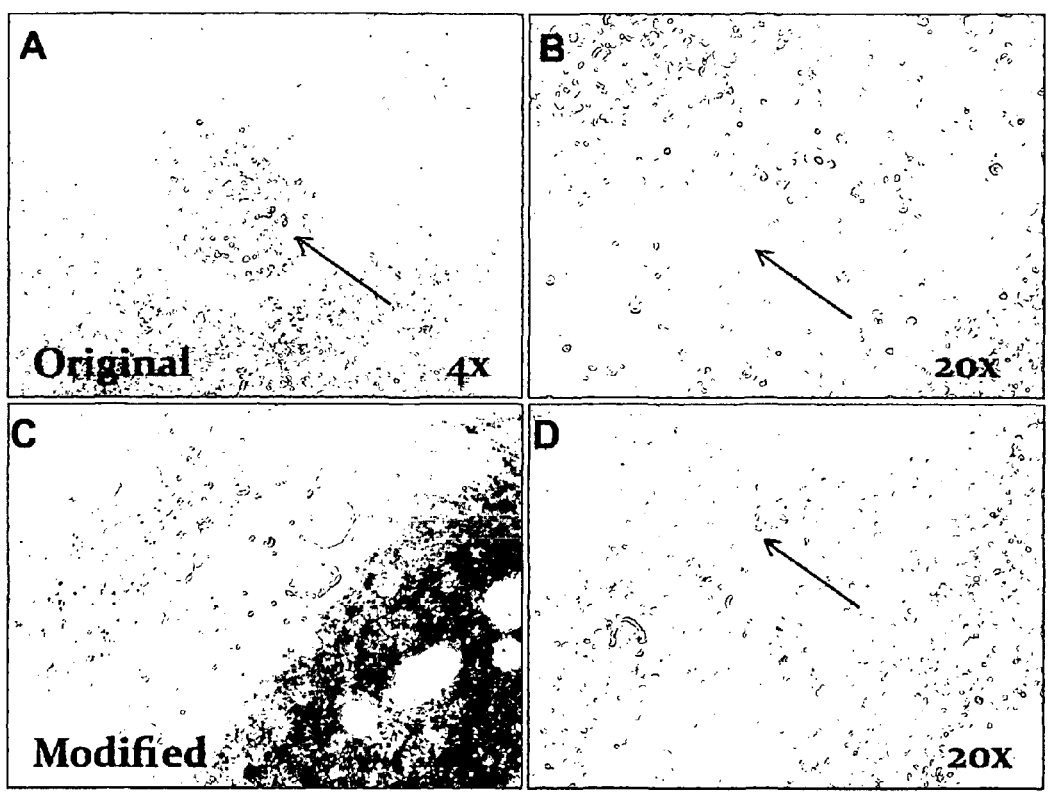
FIG. 2A-D shows populations of recently differentiated corneal endothelial cells.

The present application provides methods for obtaining corneal endothelial cells through directed differentiation of pluripotent or multipotent stem cells, including human embryonic stem cells (hESC), somatic cells (including transdifferentiated cells and stem cells such as neural crest stem cells), and induced human pluripotent stem cells (hiPSC). It is expected that these cells can provide an alternative to the burdensome collection of donated corneas for therapeutic use.

As further detailed below, monolayers of corneal endothelium were produced by directed differentiation of human embryonic stem cells (hESC). hESC were induced to differentiate into neural crest progenitors, and subsequently, the neural crest progenitors were exposed to growth factors that induced the formation of corneal endothelial cells. Corneal endothelial cell identity was confirmed based on characteristic morphological features and gene expression, including presence of markers of corneal endothelial cells, and absence of certain markers of vascular endothelial cells (whose marker expression has some overlap with corneal endothelial cells).

In exemplary embodiments, populations of corneal endothelial cells may be tested for presence of other cell types, e.g., any remaining pluripotent cells and/or neural crest stem cells. Exemplary methods that may be used to detect other cell types in a corneal endothelial cell population include methods that can detect expression of markers of pluripotent cells, such as Northern blotting, Western blotting, immunostaining, PCR, and other methods known in the art. See, generally, Ausubel, Current Protocols in Molecular Biology (Current Protocols, 1988); Ausubel et al., Short Protocols in Molecular Biology (Current Protocols; 5th Edition, 2002); Sambrook et al., Molecular Cloning: A Laboratory Manual (Cold Spring Harbor Laboratory Press, 3rd edition, 2001); Sambrook et al., The Condensed Protocols from Molecular Cloning: A Laboratory Manual (Cold Spring Harbor Laboratory Press, 2006), each of which is incorporated by reference herein in its entirety.

In exemplary embodiments cells (e.g., hES cells, NCSCs, and/or CEC) may be cultured on a matrix. The matrix may comprise one or more of: transforming growth factor beta (TGF-beta), epidermal growth factor (EGF), insulin-like growth factor 1, fibroblast growth factor 2 (FGF2, sometimes also referred to as bFGF), platelet-derived growth factor (PDGF), laminin (e.g., laminin-511, which may be recombinant), fibronectin, vitronectin (e.g., recombinant zebrafish modified vitronectin), proteoglycan, entactin, collagen, collagen I, collagen IV, collagen VIII, heparan sulfate, Matrigel (a soluble preparation from Engelbreth-Holm-Swarm (EHS) mouse sarcoma cells, the major components of which include laminin, collagen IV, entactin and heparan sulfate proteoglycan and which also includes growth factors, collagenases, plasminogen activators and may include other components), a human basement membrane extract, or any combination thereof. In another embodiment, the matrix is from human or non-human animal (e.g., bovine, mouse or rat origin). In exemplary embodiments, cells (e.g., hES cells, NCSCs, and/or CEC) may be cultured on feeder cells (including but not limited to MEFs, NHDFs, other fibroblasts, or other non-fibroblast cell types), which may be mitotically inactivated (e.g., by gamma irradiation, Mitomycin C treatment, or other methods known in the art). Suitable matrixes and/or feeder cells generally permit the maintenance of hES cells, hES cell differentiation into NCSCs, or differentiation of NCSCs into CEC.

Additional exemplary embodiments may include sensitive and specific detection of other cell types (e.g., ES cells and/or neural crest stem cells) in a CEC cell population, using methods disclosed in co-owned international application ser. no. PCT/US11/45232 and U.S. Provisional Application Ser. Nos. 61/414,770 and 61/367,038, each of which is incorporated by reference herein in its entirety. For example, a cell population may be stained for two markers indicative of ES cells (e.g., stained for alkaline phosphatase (AP) expression and stained expression of an ES cell-specific marker such as Oct-4, Nanog, etc.), and cells may be examined to detect any cells that express those ES cell markers. Likewise, the population may be stained for the presence of two or more markers indicative of neural crest stem cells and examined to detect any cells that express those neural crest stem cell markers. As described in the aforementioned applications, highly sensitive detection can be attained using these methods through examination of a sufficiently large numbers of cells, e.g., between at least one million cells and at least 10 million cells. Preferably, at least one stain is detectable under visible light, permitting the cells to be viewed under visible light to detect at least one of the markers, which may greatly increase throughput; the second marker may be visible under UV light and any cell positive for said first marker may be visualized under UV light to detect expression of said second marker, wherein a cell detected to express both markers is scored as a cell of the type to be detected.

Alternatives and Additional Factors for Production of Corneal Endothelial Cells from Embryonic Stem Cells As further described in the Examples below, Applicants have demonstrated methods for production of corneal endothelial cells (CEC) by differentiation of hES cells through contact with certain factors. In addition to the specific factors used in the examples, it is expected that other factors, e.g., equivalents, agonists, etc. may be used in place of or in addition to any of the identified factors. Suitable combinations of factors can be readily and concentrations thereof can be readily determined by those of ordinary skill in the art. For example, hES cell populations can be readily contacted with candidate compositions and monitored for adoption of neural crest stem cell fate, such as expression of genetic markers thereof including those identified herein and in WO/2010/096496, which is incorporated by reference herein in its entirety. Additionally, neural crest stem cell populations (including populations of ES cells undergoing the process of neural crest induction) can be contacted with candidate compositions and monitored for adoption of corneal endothelial cell fate, such as the characteristic morphology (see, e.g., FIG. 2), as well as expression of one or more markers characteristic of corneal endothelial cells, including those identified herein and others known in the art. Cells may be further monitored for decreased or absent expression of one or more markers indicative of one or more other cell types, said decreased or absent expression typically being evaluated relative to the expression level of cells of said other type, for example, decreased or absent expression of one or more vascular endothelial cell markers (such as VWF and/or CD31/PECAM-1), and/or decreased or absent expression of one or more ES cell markers, and/or decreased or absent expression of neural crest stem cell markers in CEC. Cells such as hES cells or neural crest stem cells may be exposed to different factors or combinations of factors and may be monitored for adoption of CEC phenotypes, optionally together with suitable positive and negative controls, to identify operative factors and concentrations thereof, or to determine operative or optimal concentrations of factors.

Dual Smad Inhibitors

Exemplary embodiments of the presently disclosed method include differentiating hESC in the presence of Noggin (e.g., human Noggin polypeptide, such as NP_005441.1 or the mature polypeptide contained therein) and SB431542 (collectively, "dual SMAD inhibitors"). Such cultures may produce neural crest stem cells, and further culturing (e.g., in the presence of additional factors) may produce CEC or other cell types. Applicants envision that alternative factors (individually and/or in combination) could be used in the disclosed methods in place of either or both of the dual SMAD inhibitors, and/or be used in addition to one or both of these factors. Though these factors are sometimes referred to as "dual" SMAD inhibitors, more or fewer than two factors may be utilized within the scope of these methods.

Noggin is a secreted BMP inhibitor that reportedly binds BMP2, BMP4, and BMP7 with high affinity to block TGFβ family activity. SB431542 is a small molecule that reportedly inhibits TGFβ/Activin/Nodal by blocking phosphorylation of ACTRIB, TGFβR1, and ACTRIC receptors. SB431542 is thought to destabilize the Activin- and Nanogmediated pluripotency network as well as suppress BMP induced trophoblast, mesoderm, and endodermal cell fates by blocking endogenous Activin and BMP signals. It is expected that agents having one or more of the aforementioned activities could replace or augment the functions of one or both of Noggin and SB431542, e.g., as they are used in the context of the disclosed methods. For example, applicants envision that the protein Noggin and/or the small molecule SB4312542 could be replaced or augmented by one or more inhibitors that affect any or all of the following three target areas: 1) preventing the binding of the ligand to the receptor; 2) blocking activation of receptor (e.g., dorsomorphin), and 3) inhibition of SMAD intracellular proteins/transcription factors. Exemplary potentially suitable factors include the natural secreted BMP inhibitors Chordin (which blocks BMP4) and Follistatin (which blocks Activin), as well as analogs or mimetics thereof. Additional exemplary factors that may mimic the effect of Noggin include use of dominant negative receptors or blocking antibodies that would sequester BMP2, BMP4, and/or BMP7. Additionally, with respect to blocking receptor phosphorylation, dorsomorphin (or Compound C) has been reported to have similar effects on stem cells. Inhibition of SMAD proteins may also be effected using soluble inhibitors such as SIS3 (6,7-Dimethoxy-2-((2E)-3-(1-methyl-2-phenyl-1H-pyrrolo[2,3-b]pyridin-3-yl-prop-2-enoyl))-1,2,3,4-tetrahydroisoquinoline, Specific Inhibitor of Smad3, SIS3), overexpression of one or more of the inhibitor SMADs (e.g., SMAD6, SMAD7, SMAD10) or RNAi for one of the receptor SMADs (SMAD1, SMAD2, SMAD3, SMAD5, SMAD8/9). Another combination of factors expected to be suitable for generating neural progenitors comprises a cocktail of Leukemia Inhibitory Factor (LIF), GSK3 inhibitor (CHIR 99021), Compound E (γ secretase inhibitor XXI) and the TGFβ inhibitor SB431542 which has been previously shown to be efficacious for generating neural crest stem cells (Li et al., Proc Natl Acad Sci USA. 2011 May 17; 108(20):8299-304). Additional exemplary factors may include derivatives of SB431542, e.g., molecules that include one or more added or different substituents, analogous functional groups, etc. and that have a similar inhibitory effect on one or more SMAD proteins. Suitable factors or combinations of factors may be identified, for example, by contacting hESC with said factor(s) and monitoring for adoption of neural crest stem cell phenotypes, such as characteristic gene expression (including expression of the markers described herein, expression of a reporter gene coupled to a neural crest stem cell promoter, or the like) or the ability to form CEC or another cell type capable of differentiating from neural crest stem cells.

In exemplary embodiments, hES cells, such as hES cells undergoing neural crest induction, may be cultured in the presence of SB431542, which may be present in the culture media in a concentration as low as 10 nM, 20 nM, 50 nM, 0.1 μM, or lower, or as high as 20 μM, 50 μM, 100 μM, or higher, such as 10 nM to 100 μM, 0.1 μM to 50 μM, 0.1-20 μM, or 1-20 μM, preferably about 10 μM. In exemplary embodiments, hES cells, such as hES cells undergoing neural crest induction, may be cultured in the presence of Noggin, which may be present in the culture media in a concentration as low as 10 ng, 20 ng/ml, 50 ng/ml, 100 ng/ml, or lower, or as high as 700 ng/ml, 1000 ng/ml, 1500 ng/ml, 2000 ng/ml, 3000 ng/ml, 4000 ng/ml, 5000 ng/ml, or higher, such as 10 ng/ml to 5,000 ng/ml, 100 ng/ml to 700 ng/ml, or 400 ng/ml to 600 ng/ml, preferably about 500 ng/ml. hES cells may also be cultured with combinations of SB431542 and Noggin, e.g., combinations of the foregoing concentrations.

PDGFB

Exemplary embodiments of the presently disclosed method include culturing neural crest stem cells in the presence of PDGFB (e.g., human PDGFB polypeptide, such as NP_002599.1 or the mature polypeptide contained therein), and culture media comprising PDGFB (sometimes referred to in the literature as PDGFBB due to its existence as a dimer). It is envisioned that one or more additional factors may be used in addition to or instead of PDGFB. For example, PDGFB reportedly signals through PDGFRβ, which then activates the PKC pathway. Both PDGFRα and PDGFRβ are expressed in the developing cornea, so PDGFAA or PDGFAB may be suitable for use in addition or alternative to PDGFB. As an additional example, Phorbol 12-myristate 13-acetate (PMA) (which is thought to activate PKC) may be used instead of or in addition to PDGFB. VEGF is structurally related to PDGF and therefore may also be used instead of or in addition to PDGFB.

In exemplary embodiments, cultures comprising neural crest stem cells, such as in a culture comprising hES cells after commencing neural crest induction or during neural crest induction, are cultured in the presence of PDGFB which may be present in the culture media in a concentration as low as 0.1 ng/ml, 0.2 ng/ml, 0.5 ng/ml, 1 ng/ml, or lower, or as high as 10 ng/ml, 20 ng/ml, 30 ng/ml, 50 ng/ml, 75 ng/ml, 100 ng/ml, 125 ng/ml, 150 ng/ml, 200 ng/ml, 250 ng/ml, or higher, such as 0.1 ng/ml to 250 ng/ml, 0.5 ng/ml to 150 ng/ml, 1-50 ng/ml, 2-20 ng/ml, preferably about 10 ng/ml.

DKK2

Exemplary embodiments of the presently disclosed method include culturing cells in the presence of DKK2 (e.g., human DKK2 polypeptide, such as NP_055236.1 or the mature polypeptide contained therein), and culture media comprising DKK2. For example, neural crest stem cells (whether obtained from differentiating hES cells or other sources) and/or differentiating hES cells cultured under conditions expected to produced neural crest stem cells (e.g., culture in the presence of dual SMAD inhibitors) may be cultured in the presence of DKK2. It is envisioned that one or more additional factors may be used in addition to or instead of DKK2, e.g., a DKK2 agonist. DKK2 has been shown to be both an inhibitor and activator of the Wnt pathway in various cell-dependent contexts. Exemplary DKK2 agonists include any Wnt pathway activators and/or inhibitors that may functionally replace DKK2 in the differentiation of CEC. When DKK2 acts as an inhibitor it reportedly binds to the co-receptor LRP5/6 and Kremen, which then causes the receptor to be internalized and degraded. For example, RNAi that targets and knocks down the expression of LRP5/6 or Kremen, may be used in addition to or instead of DKK2. Wnt pathway inhibitors such as DKK 1, 3, 4 and Soggy, secreted frizzled related proteins (Frzb), and Wnt inhibitor factor (WIF) may also be used in addition to or instead of DKK2. Another potentially suitable Wnt pathway inhibitor is Casein Kinase 1-7 which is expected to block signal transduction. Factors (such as small molecules) affecting β catenin, for example factors that stabilize or destabilize β catenin, may also be used in addition to or instead of DKK2. Additionally, modulating the LEF/TCF transcription factor members may be used in addition to or instead of DKK2. Exemplary Wnt pathway activators include Wnt proteins, nucleic acids encoding Wnt proteins, LiCl, inhibitors of negative regulators of Wnt pathway (e.g., RNAi or other inhibitors targeting Axin and/or APC), norrin, R-spondin2. Small molecule Wnt pathway activators include: (hetero)arylpyrimidines, IQ1, BIO (6-bromoindirubin-3'-oxime), 2-amino-4-[3,4-(methylenedioxy)benzyl-amino]-6-(3-methoxyphenyl)pyrimidine, WAY-316606, QS11, SB-216763, SB-216763, and DCA. Small molecule Wnt pathway inhibitors include: IWR, pyrvinium, ICG-001, PKF115-584 (and several other compounds), IWP, Ant1.4Br/Ant 1.4Cl, Niclosamide, apicularen and bafilomycin, XAV939, NSC668036, 2,4-diamino-quinazoline, and Quercetin. Additional exemplary WNT pathway inhibitors which may be utilized include ID8 (Hasagawa et al., Stem Cells Transl Med. 2012 January; 1(1):18-28), Wnt C59 (Proffitt Cancer Res Published OnlineFirst Nov. 27, 2012; DOI:10.1158/0008-5472.CAN-12-2258), CGK062 (Gwak et al., PLoS ONE. 2012; 7(10):e46697), IWP2 (Blauwkamp et al., Nat Commun. 2012; 3:1070), FH535 (Iida et al., PLoS One. 2012; 7(9):e44418), and Riluzole (Zhao et al., J Biomol Screen. 2012 October; 17(9):1252-63). Combinations of the foregoing factors may also be used in addition to or instead of DKK2, e.g., combinations comprising more than one Wnt pathway activator, more than one Wnt pathway inhibitor, or at least one Wnt pathway activator and at least one Wnt pathway inhibitor.

In exemplary embodiments, cultures comprising neural crest stem cells, such as in a culture comprising hES cells after commencing neural crest induction or during neural crest induction, are cultured in the presence of DKK2, which may be present in the culture media in a concentration as low as 1 ng/ml, 2 ng/ml, 3 ng/ml, 4 ng/ml, 5 ng/ml, 6 ng/ml, or lower, or as high as 10 ng/ml, 20 ng/ml, 50 ng/ml, 100 ng/ml, 1 µg/ml, 5 µg/ml, 10 µg/ml, 15 ug/ml, or higher, such as 1 ng/ml-15 µg/ml, 10 ng/ml-15 µg/ml, 1 ng/ml-1 µg/ml, 1 ng/ml-100 ng/ml, 2 ng/ml-20 ng/ml, or 5 ng/ml-20 ng/ml, preferably about 10 ng/ml.

Angiopoietin-Like Protein 7 (ANGPL7)

In additional experimental results obtained by the present inventors in which ANGPL7 was included in the culture media (in combination with DKK2 and PDGFB) in the methods disclosed in Example 1, the resulting CEC exhibited tighter packing and more hexagonal morphology. These results indicate that ANGPL7 may be a positive factor for generating corneal endothelial cells, particularly for producing CEC in a high-density sheet or layer which may be preferred for transplant. Accordingly, ANGPL7 may optionally be used in the differentiation of corneal endothelial cells, for example by its inclusion in the culture during and/or after formation of corneal endothelial cells. ANGPL1-8 may be used in place of or in addition to ANGPL7.

FGF2

In exemplary embodiments, FGF2 may be present in cultures of hES cells, e.g., during neural crest induction, which may be present in the culture media in a concentration as low as 1 ng/ml, 2 ng/ml, 3 ng/ml, 4 ng/ml, 5 ng/ml, 6 ng/ml, or lower, or up to 10 ng/ml, 20 ng/ml, 50 ng/ml, 100 ng/ml, 500 ng/ml, or 1 µg/ml, such as 1 ng/ml-1 ug/ml, 1 ng/ml-100 ng/ml, 2 ng/ml-10 ng/ml, 6 ng/ml-100 ng/ml, preferably about 6 ng/ml.

In exemplary embodiments, FGF2 may be present in cultures of neural crest stem cells or CEC, e.g., during CEC differentiation from neural crest stem cells or in cultures comprising CEC, which may be present in the culture media in a concentration as low as 0.1 ng/ml, 0.2 ng/ml, 0.5 ng/ml, 1 ng/ml, 2 ng/ml, 3 ng/ml, 4 ng/ml, 5 ng/ml, 6 ng/ml, or lower, or up to 10 ng/ml, 20 ng/ml, 50 ng/ml, 100 ng/ml, 500 ng/ml, or 1 µg/ml, such as 0.1 ng/ml-1 ug/ml, 0.1 ng/ml-400 ng/ml, 0.1 ng/ml-100 ng/ml, 0.1 ng/ml-10 ng/ml, 1 ng/ml-100 ng/ml, preferably about 6 ng/ml.

B27

B27 (B-27 Serum-Free Supplement (50×) liquid, Invitrogen cat #17504-044) is a culture medium supplement containing d-Biotin, BSA, L-Carnitine HC, Corticosterone, Ethanolamine HCl, D-Galactose (Anhyd.), Insulin (Human, Zn), Linoleic Acid, Linolenic Acid, Progesterone, Putrescine.2HCl, Sodium Selenite (1000×), T-3/Albumin Complex, Transferrin (Human, Iron-Poor), and Vitamin A Acetate, which is prepared in distilled water (Brewer et al., J. Neurosci. Res. 35:567-576 (1993)). In exemplary embodiments, CEC may be cultured in a medium comprising B27 (such as after differentiation or during differentiation) in a concentration as low as 0.01×, 0.02×, 0.05×, 0.1×, or lower, or as high as 0.5×, 1×, 2×, 3×, 5×, 10×, or higher, such as 0.01×-10×, 0.02×-5×, 0.05×-1×, or 0.1×-1×, preferably about 0.1×.

TGFβ2

Applicants envision that TGFβ2 may be used to promote differentiation of neural crest stem cells into corneal endothelial cells. For example, in mice lacking both copies of TGFβ2, the corneal endothelium is absent. Although the neural crest migrates at the correct time and place, the corneal endothelium does not form. Additionally, TGFβ2 is highly expressed in the lens at the time the neural crest are adjacent to the lens. Based in part on the foregoing, Applicants envision that in exemplary embodiments, TGFβ2 may be used to promote the differentiation of neural crest into corneal endothelial cells.

Factors that Promote Corneal Endothelial Cell Proliferation

Exemplary embodiments may include the use of one or more factors that promote corneal endothelial cell proliferation. For example, such factors may be included in a culture of cells during and/or subsequent to formation of corneal endothelial cells. Particular exemplary factors include Hepatocyte growth factor (HGF) and/or Keratinocyte growth factor (KGF), which have been shown to induce proliferation in cultured corneal endothelial cells (Wilson et al., Invest Ophthalmol Vis Sci. 1993 July; 34(8):2544-61).

IL1α

IL1α has been shown to upregulate HGF and KGF in corneal stromal fibroblasts. Applicants envision that IL1α may contribute to the formation and/or maintenance of corneal endothelial cells as well. Accordingly, in exemplary embodiments, IL1α may be included in a culture of cells during and/or subsequent to formation of corneal endothelial cells.

Sheets, Monolayers, Cultures, and Pharmaceutical Preparations

Exemplary embodiments provide a culture of corneal endothelial cells, such as a sheet or monolayer of CEC, wherein the CEC are produced by differentiation of embryonic stem cells. The sheet or monolayer may have a cell density of at least 1,000 cells/mm$^2$, at least 1,500 cells/mm$^2$, 2,000 cells/mm$^2$, at least 2,500 cells/mm$^2$, at least 3,000 cells/mm$^2$, at least 3,500 cells/mm$^2$, at least 4,000 cells/mm$^2$, at least 4,500 cells/mm$^2$, at least 5,000 cells/mm$^2$, or higher. Optionally, the sheet or monolayer of corneal endothelial cells may further comprise a Descemet's membrane or other matrix produced by the corneal endothelial cells. For example, a matrix may be prepared from media conditioned by CEC (e.g., CEC produced from hES cells), e.g., by concentrating proteins in said media, and optionally adding matrix components, growth factors, or the like.

Donor-derived CEC reportedly accumulate numerous markers and changes in gene expression that are thought to result from accumulated oxidative damage and other insults. See Joyce et al., Invest. Ophthalmol. Vis. Sci. Mar. 24, 2011 vol. 52 no. 3 1641-1649, which is incorporated by reference herein in its entirety. CEC produced by the present methods are expected to exhibit one or more attributes of "youthful" CEC. For example, as compared to donor-derived CEC (especially adult-derived CEC) it is expected that the CEC may exhibit decreased levels of oxidative damage; nuclear DNA damage foci; decreased levels of expression of p21Cip1; decreased levels of expression of p16INK4a; decreased levels of expression of cytoglobin protein; decreased levels of expression of GPX-1 protein, and decreased levels of 8-hydroxy-2_-deoxyguanosine (8-OHdG).

Also provided are methods of culturing CEC, or precursors thereof, of the present disclosure, said methods comprising culturing said CEC or precursors thereof on a carrier, wherein said methods may optionally include transferring or releasing a sheet or monolayer of CEC or precursors thereof onto said carrier. Further provided are methods of preparing a composition comprising CEC, or precursors thereof, of the present disclosure, said methods comprising culturing said CEC or precursors thereof on a carrier, which may optionally include transferring or releasing a sheet or monolayer of CEC or precursors thereof onto said carrier, wherein said composition may be suitable for transplantation. Additionally provided are cultures of CEC, or precursors thereof, of the present disclosure, said cultures comprising CEC, or precursors thereof, that are adherent to a carrier. Exemplary carriers may be suitable for transplantation. Exemplary carriers include carriers that may dissolve or otherwise disappear in vivo when the sheet or monolayer of corneal endothelial cells is transplanted into a host organism, such as gelatin (see Hsiue et al., supra). Additional exemplary carriers include fibrin-based matrixes, endothelium-denuded corneal buttons, denuded Descemet's membrane, directly onto the stromal layer, e.g., devitalized stromal cornea (e.g., from a human cadaver or non-human animal), fresh corneal stromal discs (from a human or non-human animal), and/or an amniotic membrane (preferably without amniotic cells). The dimensions and/or thickness of the carrier are preferably suitable for implantation into the eye, e.g., about 100 microns thick or less.

For example, the CEC or precursor thereof may be cultured on a substrate from which an intact sheet or monolayer of cells can be released, e.g., a substrate such as a thermoresponsive polymer such as a thermoresponsive poly(N-isopropylacrylamide) (PNIPAAm)-grafted surface, upon which cells adhere and proliferate at the culture temperature, and then upon a temperature shift, the surface characteristics are altered causing release the cultured cell sheets (e.g., by cooling to below the lower critical solution temperature (LCST) (see da Silva et al., Trends Biotechnol. 2007 December; 25(12):577-83; Hsiue et al., Transplantation. 2006 Feb. 15; 81(3):473-6; Ide, T. et al. (2006); Biomaterials 27, 607-614, Sumide, T. et al. (2005), FASEB J. 20, 392-394; Nishida, K. et al. (2004), Transplantation 77, 379-385; and Nishida, K. et al. (2004), N. Engl. J. Med. 351, 1187-1196 each of which is incorporated by reference herein in its entirety). For example, cultured CEC may be released onto a carrier, such as a carrier suitable for transplantation, e.g., as described in the preceding paragraph.

As a further example, the CEC or precursor thereof may be contained in a laminate, which may comprise a transparent type I collagen sheet that optionally has been coated with an adhesive factor or a bioadhesive and a cultured layer of CEC or precursor thereof provided on said transparent type I collagen sheet, wherein said transparent type I collagen sheet may have a thickness ranging from 5 to 50 micrometers. The adhesive factor or bioadhesive layer may be on the opposite side from the cultured layer of human corneal endothelial cells, and/or between said transparent type I collagen sheet and said CEC or precursor thereof. The adhesive factor may be a fibronectin, e.g., human plasma fibronectin. For example, a laminate may be prepared by placing or releasing a sheet or monolayer of CEC or precursors thereof onto a transparent type I collagen sheet that optionally has been coated with an adhesive factor or a bioadhesive, and/or by culturing a suspension comprising CEC or precursors thereof in contact with said transparent type I collagen sheet and allowing said cells to form a laminate comprising CEC or a precursor thereof. Further exemplary compositions, substrates, methods, and the like, in which the cells of the present disclosure may be used, are described in U.S. Pat. No. 7,959,939 and US 2010/0233240, each of which is incorporated by reference herein in its entirety.

In one aspect, the present disclosure provides cultures comprising corneal endothelial cells. As further described herein, CEC of the present disclosure may be maintained in culture for prolonged periods of time and may form a population that is non-dividing.

Exemplary compositions may include an inhibitor of Rho-associated kinase (ROCK), such as Y-27632 (also referred to as (+)-trans-4-(1-aminoethyl)-1-(4-pyridyl carbamoyl)cyclohexane or by its IUPAC name (1R,4r)-4-((R)-1-aminoethyl)-N-(pyridin-4-yl)cyclohexanecarboxamide; see Watanabe et al., Nat Biotechnol. 2007 June; 25(6):681-6)), preferably in an amount sufficient to promote survival of the cells. See, e.g., Okumura et al., Invest Ophthalmol Vis Sci. 2009; 50:3680-3687, Okumura et al., Br J Ophthalmol. 2011 July; 95(7):1006-9, published U.S. patent applications 2010/0209402 and 2010/0233240, each of which is incorporated by reference herein in its entirety.

In a further aspect the CEC may be cultured in the presence of Y-27632 and/or another ROCK inhibitor, for example before, during and/or after passaging, which may improve cell viability. Additional exemplary ROCK inhibitors include small molecules, siRNAs, miRNAs, antisense RNA, or the like, that may target a rho-associated kinase or member of the ROCK signaling pathway. Exemplary ROCK inhibitors include H-1152, Y-30141, Wf-536, HA-1077, hydroxyl-HA-1077, GSK269962A and SB-772077-B, 1-(5-isoquinolinesulfonyl)homopiperazine (fasudil), (+)-trans-4-(1-aminoethyl)-1-(4-pyridylcarbamoyl)cyclohexane (Y-27632), as well as salts thereof, preferably pharmaceutically acceptable salts such as hydrochloride salts. In exemplary embodiments, the ROCK inhibitor may have a concentration of about 0.05 to about 50 microM, for example, at least or about 0.05, 0.1, 0.2, 0.5, 0.8, 1, 1.5, 2, 2.5, 5, 7.5, 10, 15, 20, 25, 30, 35, 40, 45, or 50 microM, including any range derivable therein, or any concentration effective for promoting cell growth and/or survival.

The CEC of the present disclosure may also be cultured under conditions that promote proliferation. For example, the CEC may be contacted with an effective amount of at least one growth factor that promotes proliferation of corneal endothelial cells (e.g., an antibody that specifically binds to a cell surface protein on the corneal adult human corneal endothelial cell that is involved in cell-cell adhesion, such as antibody that specifically binds to a protein selected from the group consisting of a cadherin, ZO-1 protein, and connexin-43, which may results in interruption in cell-cell contacts in at least 15%, at least 50%, or at least 80% of the CEC, wherein the concentration of said growth factor may be about 0.02-3.0 mg/ml or about 0.2-2.0 mg/ml); and subsequently exposed to an effective amount of at least one agent that promotes interruption of cell-cell contacts between adjacent corneal endothelial cells (such as a calcium chelator, e.g., ethylenediaminetetraacetic acid (EDTA) or ethylene glycol-bis[beta-aminoethylether]-N,N,N',N'-tetraacetic acid (EGTA)), and, optionally, subsequently contacting the CEC with an effective amount of at least one growth factor that promotes proliferation of corneal endothelial cells (e.g., an antibody that specifically binds to a cell surface protein on the corneal adult human corneal endothelial cell that is involved in cell-cell adhesion, such as antibody that specifically binds to a protein selected from the group consisting of a cadherin, ZO-1 protein, and connexin-43, which may results in interruption in cell-cell contacts in at least 15%, at least 50%, or at least 80% of the CEC, wherein the concentration of said growth factor may be about 0.02-3.0 mg/ml or about 0.2-2.0 mg/ml). Further, the CEC may be cultured in a medium comprising a serum-free cell culture medium comprising insulin, transferrin, and selenium; fibroblast growth factor (pituitary); epidermal growth factor; nerve growth factor; a calcium chelator, and optionally an antibiotic antimycotic solution. See U.S. Pat. No. 6,548,059 and Senoo et al. Investigative Ophthalmology & Visual Science, September 2000, Vol. 41, No. 10, pg. 2930-2935, each of which is incorporated by reference herein in its entirety.

As a further example, the CEC may be cultured in a medium comprising insulin; transferrin; selenium; 1-100 ng/ml nerve growth factor; 5-400 ng/ml fibroblast growth factor (pituitary); 1-200 ng/ml epidermal growth factor; 1-25% fetal bovine serum; 10-50 micrograms/ml ascorbic acid; 0.001-0.01% human lipids; 0.01-0.12% chondroitin sulfate; 100-300 micrograms/ml calcium chloride. Optionally, the medium may further comprise one or more of 10-100 micrograms/ml gentamycin; RPMI-1640 multiple vitamin solution (1/50-1/200); and antibiotic antimycotic solution (1/50-1/200). For example, the CEC may be cultured in growth medium may comprise 20 ng/ml nerve growth factor; 40 ng/ml fibroblast growth factor (pituitary); 5 ng/ml epidermal growth factor; 8% fetal bovine serum; 20 micrograms/ml ascorbic acid; 0.005% human lipids; 0.08% chondroitin sulfate; 200 micrograms/ml calcium chloride. Optionally, the medium may further comprise one or more of: 50 micrograms/ml gentamycin; RPMI-1640 multiple vitamin solution (1/100); and antibiotic antimycotic solution (1/100). See U.S. Pat. No. 6,541,256, which is incorporated by reference herein in its entirety.

As another example, the CEC may be placed or cultured on an amniotic membrane, such as the basement membrane side of the amniotic membrane, e.g., with or without amniotic cells, wherein the amniotic membrane may have an extracellular matrix. The CEC may be placed on the amniotic membrane as a sheet or applied thereto as a individual cells, such as cells in a suspension, which may be allowed to settle by gravity and/or centrifugation. The CEC may be cultured on the amniotic membrane and allowed to proliferate. The CEC placed or cultured on an amniotic membrane may also be used as a surgical graft (or used in the manufacture of a medicament), e.g., for the treatment of a disease of corneal endothelial cells. See, e.g., U.S. Pub. No. 2007/0254361, which is incorporated by reference herein in its entirety.

Therapeutic Methods

In another aspect, the present disclosure provides therapeutic methods for the prevention and/or treatment of disease, preferably diseases affecting corneal endothelial cells or amenable to treatment by the transplantation or administration thereof, including, for example, primary diseases such as Fuch's dystrophy, iridocorneal endothelial syndrome, posterior polymorphous dystrophy, and congenital hereditary endothelial dystrophy, and secondary diseases for which an effective treatment is replacement of the corneal endothelium including corneal dystrophies, contact lens usage, cataract surgery, and late endothelial failure in cornea transplantation.

Exemplary therapeutic methods may further include administration of an immunosuppressive agent. Immunosuppressants that may be used include but are not limited to anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, tacrolimus, mycophemolate mofetil, corticosteroids and mesenchymal stem cells. The immunosuppressants may be dosed at least about 1, 2, 4, 5, 6, 7, 8, 9, or 10 mg/kg. When immunosuppressants are used, they may be administered systemically or locally, and they may be administered prior to, concomitantly with, or following administration of the CEC. Immunosuppressive therapy may continue for weeks, months, years, or indefinitely following administration of cells. For example, the patient may be administered 5 mg/kg cyclosporin for 6 weeks following administration of the CEC. Furthermore, a composition of CEC may comprise an immunosuppressive agent, e.g., any of the foregoing.

In one aspect, the present disclosure provides therapeutic methods comprising transplantation of a cultured sheet or monolayer of CEC or precursors thereof into the eye of a subject in need thereof, e.g., an individual suffering from a disease of corneal endothelial cells. For example, the eye of the subject may be prepared by removal of the Descemet's membrane, and said cultured sheet or monolayer of CEC may be placed into the anterior chamber of said eye, e.g., in contact with (and preferably attached or affixed to) the posterior corneal stroma. Optionally, the sheet or monolayer of CEC or precursors thereof may be provided on a carrier, e.g., as described above, and administered to an eye of a patient.

One exemplary treatment which may be clinically preferred when only the corneal endothelium is compromised is Descemet's stripping with endothelial keratoplasty (DSEK), which includes the removal of diseased Descemet's membrane and the corneal endothelium, and subsequent transplantation of donor tissue. Procedures have been developed to replace the entire cornea (penetrating keratoplasty or PK) or leave the patient's Descemet's membrane and endothelium and replace the remaining layers with donated tissue (lamellar keratoplasty). See, generally, U.S. Pat. No. 5,755,785, U.S. Pat. No. 5,649,944, U.S. Pat. No. 7,147,648, U.S. Pat. No. 7,300,653, U.S. Pat. No. 5,584,881, U.S. Pat. No. 5,686,414, U.S. Pat. No. 7,300,654, U.S. patent application Ser. No. 10/525,391, each of which is incorporated by reference in its entirety. Additional methods of corneal endothelial surgical replacement are under development, including Descemet's Membrane Endothelial Keratoplasty (DMEK), in which the donor tissue consists only of Descemet's membrane and corneal endothelium. Another potentially promising therapeutic avenue is corneal endothelial reconstruction, in which corneal endothelial cells are cultured in vitro prior to transplantation. For example, donated human corneal cells were cultured on a polymer, released onto a bioadhesive gelatin disc, and then successfully integrated into denuded rabbit corneas, with the gelatin disc dissolving after transplantation (Hsiue et al., Transplantation. 2006 Feb. 15; 81(3):473-6, which is incorporated by reference herein in its entirety). However, methods utilizing culture cells presuppose a source of said cells, and thus are affected by the shortage of suitable donated tissues as described above. Additionally, due to differences among donated cells, it may prove difficult to produce corneal endothelial cell cultures of consistent quality and efficacy. Regulatory hurdles may also make such methods logistically difficult to perform on a large scale, due to the possibility that extensive testing for safety and/or efficacy may be required for the cells obtained from each donor. These and additional therapeutic methods are further described in Thomas John, Corneal Endothelial Transplant: DSAEK, DMEK & DLEK (JP Medical Ltd, 2010), which is incorporated by reference herein in its entirety.

Exemplary compositions of the present disclosure may be formulation suitable for use in treating a human patient, such as pyrogen-free or essentially pyrogen-free, and pathogen-free. When administered, the pharmaceutical preparations for use in this disclosure may be in a pyrogen-free, pathogen-free, physiologically acceptable form.

In certain embodiments, the preparation is suitable for administration to a human patient, and more preferably pyrogen free and/or free of non-human animal products.

In other embodiments, the preparation is suitable for administration to a non-human veterinarian mammal, such as a dog, cat or horse.

Definitions

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

In order to further define the invention, the following terms and definitions are provided herein.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Throughout this specification, the word "comprise" or variations such as "comprises" or "comprising" will be understood to imply the inclusion of a stated integer or groups of integers but not the exclusion of any other integer or group of integers.

"Agonist" (such as "DKK2 agonist," "PDGFB agonist," "SB431542 agonist," "Noggin agonist," etc.) as used herein, refers to the named agent and any others that may function in the place thereof. In the context of cell differentiation, an agonist of a given factor may be recognized by similar differentiation result (such as formation of NCSCs or CEC) being obtained in the presence of the agonist and the absence (or decreased concentration or duration of exposure) of said agent. An agonist may also be recognized, for example, by its having a similar effect on a process affected by the subject agent (e.g., similar degree of activation or inhibition of the Wnt pathway).

"Effective amount," as used herein, refers broadly to the amount of a compound or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and preexisting conditions, of the patient to be treated. The term "effective amount" is synonymous with "therapeutically effective amount" for purposes of this invention.

"Pluripotent cells" and "pluripotent stem cells" as used herein, refers broadly to a cell capable of prolonged or virtually indefinite proliferation in vitro while retaining their undifferentiated state, exhibiting a stable (preferably normal) karyotype, and having the capacity to differentiate into all three germ layers (i.e., ectoderm, mesoderm and endoderm) under the appropriate conditions. Typically pluripotent cells (a) are capable of inducing teratomas when transplanted in immunodeficient (SCID) mice; (b) are capable of differentiating to cell types of all three germ layers (e.g., ectodermal, mesodermal, and endodermal cell types); and (c) express at least one hES cell marker (such as Oct-4, alkaline phosphatase, SSEA 3 surface antigen, SSEA 4 surface antigen, NANOG, TRA 1 60, TRA 1 81, SOX2, REX1). Exemplary pluripotent cells may express Oct-4, alkaline phosphatase, SSEA 3 surface antigen, SSEA 4 surface antigen, TRA 1 60, and/or TRA 1 81. Additional exemplary pluripotent cells include but are not limited to embryonic stem cells, induced pluripotent cells (iPS) cells, embryo-derived cells, pluripotent cells produced from embryonic germ (EG) cells (e.g., by culturing in the presence of FGF-2, LIF and SCF), parthenogenetic ES cells, ES cells produced from cultured inner cell mass cells, ES cells produced from a blastomere, and ES cells produced by nuclear transfer (e.g., a somatic cell nucleus transferred into a recipient oocyte). Exemplary pluripotent cells may be produced without destruction of an embryo. For example, induced pluripotent cells may be produced from cells obtained without embryo destruction. As a further example, pluripotent cells may be produced from a biopsied blastomere (which can be accomplished without harm to the remaining embryo); optionally, the remaining embryo may be cryopreserved, cultured, and/or implanted into a suitable host. Pluripotent cells (from whatever source) may be genetically modified or otherwise modified to increase longevity, potency, homing, or to deliver a desired factor in cells that are differentiated from such pluripotent cells (for example, MSCs, and hemangioblasts). As non-limiting examples thereof, the pluripotent cells may be genetically modified to express Sirt1 (thereby increasing longevity), express one or more telomerase subunit genes optionally under the control of an inducible or repressible promoter, incorporate a fluorescent label, incorporate iron oxide particles or other such reagent (which could be used for cell tracking via in vivo imaging, MRI, etc., see Thu et al., Nat Med. 2012 Feb. 26; 18(3):463-7), express bFGF which may improve longevity (see Go et al., J. Biochem. 142, 741-748 (2007)), express CXCR4 for homing (see Shi et al., Haematologica. 2007 July; 92(7):897-904), express recombinant TRAIL to induce caspase-mediatedx apoptosis in cancer cells like Gliomas (see Sasportas et al., Proc Natl Acad Sci USA. 2009 Mar. 24; 106(12):4822-7), etc.

"Embryo" or "embryonic," as used herein refers broadly to a developing cell mass that has not implanted into the uterine membrane of a maternal host. An "embryonic cell" is a cell isolated from or contained in an embryo. This also includes blastomeres, obtained as early as the two-cell stage, and aggregated blastomeres.

"Embryonic stem cells" (ES cells or ESC) encompasses pluripotent cells produced from embryonic cells (such as from cultured inner cell mass cells or cultured blastomeres) as well as induced pluripotent cells (further described below). ES cells typically include at least mammalian ES cells, such as human ES cells ("hES cells" or "hESC") as well as murine, primate, non-human primate, bovine, porcine, etc. Frequently such cells are or have been serially passaged as cell lines. Embryonic stem cells may be used as a pluripotent stem cell in the processes of producing hemangioblasts as described herein. For example, ES cells may be produced by methods known in the art including derivation from an embryo produced by any method (including by sexual or asexual means) such as fertilization of an egg cell with sperm or sperm DNA, nuclear transfer (including somatic cell nuclear transfer), or parthenogenesis. As a further example, embryonic stem cells also include cells produced by somatic cell nuclear transfer, even when non-embryonic cells are used in the process. For example, ES cells may be derived from the ICM of blastocyst stage embryos, as well as embryonic stem cells derived from one or more blastomeres. Such embryonic stem cells can be generated from embryonic material produced by fertilization or by asexual means, including somatic cell nuclear transfer (SCNT), parthenogenesis, and androgenesis. As further discussed above (see "pluripotent cells), ES cells may be genetically modified or otherwise modified to increase longevity, potency, homing, or to deliver a desired factor in cells that are differentiated from such pluripotent cells (for example, MSCs, and hemangioblasts).

ES cells may be generated with homozygosity or hemizygosity in one or more HLA genes, e.g., through genetic manipulation, screening for spontaneous loss of heterozygosity, etc. ES cells may be genetically modified or otherwise modified to increase longevity, potency, homing, or to deliver a desired factor in cells that are differentiated from such pluripotent cells (for example, MSCs and hemangioblasts). Embryonic stem cells, regardless of their source or the particular method used to produce them, typically possess one or more of the following attributes: (i) the ability to differentiate into cells of all three germ layers, (ii) expression of at least Oct-4 and alkaline phosphatase, and (iii) the ability to produce teratomas when transplanted into immunocompromised animals. Embryonic stem cells that may be used in embodiments of the present invention include, but are not limited to, human ES cells ("ESC" or "hES cells") such as MA01, MA09, ACT-4, No. 3, H1, H7, H9, H14 and ACT30 embryonic stem cells. Additional exemplary cell lines include NED1, NED2, NED3, NED4, NED5, and NED7. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." Nature 444: 481-485. The human ES cells used in accordance with exemplary embodiments of the present invention may be derived and maintained in accordance with GMP standards.

Exemplary hES cell markers include but are not limited to: such as alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CAD-HERIN, Cluster designation 30 (CD30), Cripto (TDGF-1), GCTM-2, Genesis, Germ cell nuclear factor, and Stem cell factor (SCF or c-Kit ligand). As an addition example, embryonic stem cells may express Oct-4, alkaline phosphatase, SSEA 3 surface antigen, SSEA 4 surface antigen, TRA 1 60, and/or TRA 1 81.

The ESCs may be initially co-cultivated with murine embryonic feeder cells (MEF) cells. The MEF cells may be mitotically inactivated by exposure to mitomycin C prior to seeding ESCs in co culture, and thus the MEFs do not propagate in culture. Additionally, ESC cell cultures may be examined microscopically and colonies containing non ESC cell morphology may be picked and discarded, e.g., using a stem cell cutting tool, by laser ablation, or other means. Typically, after the point of harvest of the ESCs for seeding for embryoid body formation no additional MEF cells are used.

Exemplary ESC cell markers may also include, but are not limited to: alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CAD-HERIN, Cluster designation 30 (CD30), Cripto (TDGF-1), GCTM-2, Genesis, Germ cell nuclear factor, and Stem cell factor (SCF or c-Kit ligand).

"Induced pluripotent stem cells" or "iPS cells" refers to a further exemplary type of pluripotent stem cells generated by reprogramming a somatic cell by expressing or inducing expression of a combination of factors ("reprogramming factors"). iPS cells may be generated using cells from a variety of sources such as fetal, postnatal, newborn, juvenile, or adult somatic cells. iPS cells may be obtained from a cell bank. Alternatively, iPS cells may be newly generated (e.g., by processes known in the art) prior to commencing differentiation to CEC, NCSC, or cells or another cell type. The making of iPS cells may be an initial step in the production of differentiated cells. iPS cells may be specifically generated using material from a particular patient or matched donor with the goal of generating tissue-matched cells. iPS cells can be produced from cells that are not substantially immunogenic in an intended recipient, e.g., produced from autologous cells or from cells histocompatible to an intended recipient. As further discussed above (see "pluripotent cells"), pluripotent cells including iPS cells may be genetically modified or otherwise modified to increase longevity, potency, homing, or to deliver a desired factor in cells that are differentiated from such pluripotent cells (for example, MSCs and hemangioblasts).

As a further example, induced pluripotent stem cells may be generated by reprogramming a somatic or other cell by contacting the cell with one or more reprogramming factors.

For example, the reprogramming factor(s) may be expressed by the cell, e.g., from an exogenous nucleic acid added to the cell, or from an endogenous gene in response to a factor such as a small molecule, microRNA, or the like that promotes or induces expression of that gene (see Suh and Blelloch, Development 138, 1653-1661 (2011); Miyosh et al., Cell Stem Cell (2011), doi:10.1016/j.stem.2011.05.001; Sancho-Martinez et al., Journal of Molecular Cell Biology (2011) 1-3; Anokye-Danso et al., Cell Stem Cell 8, 376-388, Apr. 8, 2011; Orkin and Hochedlinger, Cell 145, 835-850, Jun. 10, 2011, each of which is incorporated by reference herein in its entirety). Reprogramming factors may be provided from an exogenous source, e.g., by being added to the culture media, and may be introduced into cells by methods known in the art such as through coupling to cell entry peptides, protein or nucleic acid transfection agents, lipofection, electroporation, biolistic particle delivery system (gene gun), microinjection, and the like. iPS cells can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct-4, Sox2, Nanog, and Lin28. In other embodiments, somatic cells are reprogrammed by expressing at least 2 reprogramming factors, at least three reprogramming factors, or four reprogramming factors. In other embodiments, additional reprogramming factors are identified and used alone or in combination with one or more known reprogramming factors to reprogram a somatic cell to a pluripotent stem cell. iPS cells typically can be identified by expression of the same markers as embryonic stem cells, though a particular iPS cell line may vary in its expression profile.

The induced pluripotent stem cell may be produced by expressing or inducing the expression of one or more reprogramming factors in a somatic cell. The somatic cell is a fibroblast, such as a dermal fibroblast, synovial fibroblast, or lung fibroblast, or a non-fibroblastic somatic cell. The somatic cell is reprogrammed by expressing at least 1, 2, 3, 4, 5 reprogramming factors. The reprogramming factors may be selected from Oct 3/4, Sox2, NANOG, Lin28, c Myc, and Klf4. Expression of the reprogramming factors may be induced by contacting the somatic cells with at least one agent, such as a small organic molecule agents, that induce expression of reprogramming factors.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. See, e.g., Yu et al., Science. 2009 May 8; 324(5928):797-801, which is hereby incorporated by reference in its entirety. When reprogramming factors are expressed using non-integrative vectors, the factors may be expressed in the cells using electroporation, transfection, or transformation of the somatic cells with the vectors. For example, in mouse cells, expression of four factors (Oct3/4, Sox2, c myc, and Klf4) using integrative viral vectors is sufficient to reprogram a somatic cell. In human cells, expression of four factors (Oct3/4, Sox2, NANOG, and Lin28) using integrative viral vectors is sufficient to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells. iPS cells typically can be identified by expression of the same markers as other embryonic stem cells, though a particular iPS cell line may vary in its expression profile. Exemplary iPS cells may express Oct-4, alkaline phosphatase, SSEA 3 surface antigen, SSEA 4 surface antigen, TRA 1 60, and/or TRA 1 81.

To confirm the pluripotency of the iPS cells, the cells may be tested in one or more assays of pluripotency. For example, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPS cell is obtained it may be used to produce hemangioblast and MSC cells.

"Embryo-derived cells" (EDC), as used herein, refers broadly to pluripotent morula-derived cells, blastocyst-derived cells including those of the inner cell mass, embryonic shield, or epiblast, or other pluripotent stem cells of the early embryo, including primitive endoderm, ectoderm, and mesoderm and their derivatives. "EDC" also including blastomeres and cell masses from aggregated single blastomeres or embryos from varying stages of development, but excludes human embryonic stem cells that have been passaged as cell lines.

As used herein, the term "marker" or "cell marker" refers to a gene (e.g., as an RNA) or protein whose presence identifies a particular cell or cell type. A marker for a cell may not be limited to one marker, markers may refer to a "pattern" of markers such that a designated group of markers may identity a cell or cell type from another cell or cell type, e.g., a pattern including expression of some markers and absence or low expression of other markers indicative of other cell types. For example, a population of CEC may be positive for markers of CEC and negative for markers indicative of other cell types, such as absence of markers that are expressed on other endothelial cell types, absence of markers expressed by hES cells, and/or absence of markers expressed by neural crest stem cells. Additionally, when marker expression is detected by cell staining methods (e.g., immunofluorescence and the like) a cell may be identified as positive for a particular marker given an expected staining pattern, such as tight junction localization of the marker ZO-1. Expression of the markers may be detected by any method known in the art, including but not limited to: Western Blotting, mRNA amplification-based methods (e.g., PCR, isothermal amplification, etc., which may include reverse transcription and may be applied to detect expression from single cells or multiple cells), Northern blotting, immunostaining, etc. Additionally, expression of said markers may be inferred by expression of a reporter construct (such as a fluorescent protein whose expression may be visually detected, an antibiotic resistance gene whose expression may be detected by cell survival in the presence of the antibiotic, etc.) under the control of a genetic element that confers cell type specific expression, such as the promoter of one of the foregoing markers or a fragment thereof. Exemplary reporter constructs from the literature is the pOCT4-GFP and pOCT4-LUC genes which drive expression of GFP and luciferase, respectively, in ES cells, expression of either of which is readily detectable using conventional methodologies. Further methods of detecting marker expression that may be used are known in the art. See, generally, Ausubel, Current Protocols in Molecular Biology (Current Protocols, 1988); Ausubel et al., Short Protocols in Molecular Biology (Current Protocols; 5th Edition, 2002); Sambrook et al., Molecular Cloning: A Laboratory Manual (Cold Spring Harbor Laboratory Press, 3rd edition, 2001); Sambrook et al., The Condensed Protocols from Molecular Cloning: A Laboratory Manual (Cold Spring Harbor Laboratory Press, 2006), each of which is incorporated by reference herein in its entirety.

"Corneal endothelial cells" or "CEC" refers generally to the mitochondria-rich cells that (in a living organism) line the posterior surface of the cornea and faces the anterior chamber of the eye. CEC may also be produced from another cell type, e.g., by differentiation of neural crest stem cells or ES cells, using the methods described herein. CEC differentiated from NCSCs or ES cells may be identified or recognized by their exhibition of one or more of the attributes of endogenous CEC, such as expression of CEC markers, ability to form a monolayer of uniformly sized cells with a predominantly hexagonal shape, ability to form a "leaky pump" which allows leakage of solutes and nutrients from the aqueous humor to the more superficial layers of the cornea while at the same time actively pumping water in the opposite direction, from the stroma to the aqueous. Exemplary CEC markers include but are not limited to: Na+/K+ ATPase, ZO-1, KLF13, AQP1, Collagen VIII, SLC16A3, CFTR, NBC1, CA2, AE2 SCL4A2, SCL16A1, CA12, CA4, FoxC1). For example, CEC typically express Collagen VIII, Na+K+ATPase pump, and ZO-1, and do not express vWF and CD31 (the latter being present in vascular endothelial cells). In addition CEC may express one or more corneal endothelial pump markers (which include: AQP1, CA2, CA4, CA12, SCL14A2, SLC16A1, SLC16A3, SLC16A7, CFTR, NHE1, ADCY10, voltage-dependent anion channels VDAC2 and VDAC3, chloride channel proteins CLCN2 and CLC), periocular neural crest markers (which include: PITX2, and FOXC1), and/or cell adhesion and matrix proteins (which include: Occludin, Connexin 43, 9.3E antigen, Collagen III, Collagen IV, N cadherin, VE cadherin, E cadherin, beta catenin, p120, p190 Laminin alpha 4, Nidogen-2, and Netrin 4). For example, CEC may express at least one corneal endothelial pump marker, at least one periocular neural crest marker, and at least one cell adhesion and matrix protein.

"Passaging" refers generally to the removal of cells from a culture substrate, followed by plating of the cells to grow on a culture substrate. Optionally passaging may effect a change in culture density, e.g., an increase or decrease the number of cells per unit area. In exemplary embodiments the cells may be passaged 1:1, i.e., removed from and replated on culture substrates having equal or approximately equal culture area per cell. The cells may also be passaged at a different ratio, e.g., 1:2 (i.e., having twice the culture area per cell), 1:3, 1:4, etc., or 2:1 (i.e., having half the culture area per cell), 3:1 (i.e., having three times the culture area per cell), or higher or lower ratios or non-whole number ratios. Passaging may be effected using a variety of different methods to remove the cells from the culture substrate. Exemplary methods include use of chemical agents, enzymatic agents, and/or mechanical steps, e.g., use of ethylenediaminetetraacetic acid solution (EDTA), Cell Dissociation buffer (Invitrogen cat#13151-014) Gentle Cell Dissociation Buffer (Stemcell Technologies cat #07174), Enzyme Free Cell Dissociation Solution PBS Based (Millipore cat#S-014-C), Cell Dissociation Solution Non-enzymatic (Sigma cat#C5789), Cellstripper (Cellgro cat#25-056-CI), mechanical scraping, optical tweezers, laser catapulting, tituration, circulation of a fluid (e.g., by orbital shaking or rocking), trypsin, Accutase, a collagenase such as Collagenase B. Combinations may be used, e.g., one or more chemical or enzymatic agent in combination with tituration, rocking, shaking, or other mechanical dissociation. A preferred exemplary cell dissociation buffers is EDTA 0.02% in DPBS (0.5 mM) (Sigma Cat#E8008-100ML), Cell Dissociation buffer (Invitrogen cat#13151-014) and Gentle Cell Dissociation Buffer (Stemcell Technologies cat #07174). Additional exemplary cell dissociation buffers that may be used include: Enzyme Free Cell Dissociation Solution PBS Based (Millipore cat#S-014-C), Cell Dissociation Solution Non-enzymatic (Sigma cat#C5789), Cellstripper (Cellgro cat#25-056-CI).

As used herein, the term "anaplastic lymphoma kinase" refers to family of membrane-associated membrane associated tyrosine kinase receptors that includes ALK4 (an activin receptor), ALK5 (a TGF-β1 receptor), ALK7 (a Nodal and Nodal-related protein receptor).

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting or reducing the development of the disease or condition or its clinical symptoms, and/or relieving the disease or condition, causing regression of the disease or condition or its clinical symptoms. Therapy encompasses prophylaxis, prevention, treatment, cure, remedy, reduction, alleviation, and/or providing relief from a disease, signs, and/or symptoms of a disease. Therapy encompasses an alleviation of signs and/or symptoms in patients with ongoing disease signs and/or symptoms Therapy also encompasses prophylaxis and prevention. Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms. Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms. Exemplary treatments that may be efficacious for diseases of corneal endothelial cells are described in the section "Therapeutic Methods," supra.

"Neural crest stem cells" or "NCSCs" generally refer to a neural progenitor cell having the developmental potential to produce pigmented cells co-expressing the melanosome marker, HMB45. Neural crest stem cells may be differentiated from hES cells, e.g., using dual SMAD inhibitors as described herein or as described in WO/2010/096496. Neural crest stem cells may be differentiated from hES cells using a combination of Wnt agonists (such as e.g., Wnt3a and/or (2'Z,3'E)-6-bromoindirubin-3'-oxime (BIO)) and SMAD inhibitors (such as SB431542 and/or Noggin); see Menendez et al., PNAS Nov. 29, 2011 vol. 108 no. 48 19240-19245. For example, efficient induction of NCSCs was reported after contacting hESCs with SB431542, and BIO (with or without Noggin), or with Wnt3a and SB431542. NCSCs may also be obtainable from cultures of neural rosettes, for example by culturing hES cells on MS5 stromal feeder cells (see Lee, et al., Stem Cells 25 (8), 1931-1393 (2007), which is incorporated by reference herein in its entirety. NCSCs are also obtainable from numerous tissues, including in developing embryos, in the neural tube, sciatic nerve, gut, and dorsal root ganglia; and in the juvenile and adult, in the dorsal root ganglia, bone marrow, skin, heart, cornea, teeth, and caratoid body. See Nagoshi et al., Journal of Cellular Biochemistry 107:1046-1052 (2009); Crane and Trainor, Annu. Rev. Cell Dev. Biol. 2006. 22:267-86; and Blum, Brain Research Bulletin 83 (2010) 189-193, each of which is incorporated by reference herein in its entirety.

Neural crest stem cells may be identified by expression of markers identified herein and known in the art. Exemplary neural crest stem cell markers include but are not limited to: Sox10, AP2, HNK1, Pax3, PAX7, and p75 (NGFR), as well as low or absent Pax6 expression.

"Disease of corneal endothelial cells" or "diseases of corneal endothelial cells" includes any disease or condition amenable to treatment by administration of CEC, including diseases in which a subject's CEC decrease in numbers or die, decrease in density, or otherwise become dysfunctional. Primary diseases that affect the corneal endothelium include Fuch's dystrophy, iridocorneal endothelial syndrome, posterior polymorphous dystrophy, and congenital hereditary endothelial dystrophy. Secondary diseases or conditions for which an effective treatment may include replacement of the corneal endothelium include corneal dystrophies, contact lens usage, cataract surgery, and late endothelial failure in cornea transplantation. Diseases of corneal endothelial cells additionally include any injury to the cornea, e.g., caused by chemical irritation, injury due to contact lens use, reaction or sensitivity (e.g., to contact lens solutions, cosmetics, eye drops, medications, smoke, etc.), scratches, scrapes, abrasions, bruising, a foreign object in the eye (e.g., sand or dust), or exposure to ultraviolet light (from e.g., sunlight, sun lamps, snow reflections, water reflections, or arc-welding or other exposure).

"Transdifferentiation"—In the present disclosure, transdifferentiation refers to conversion of one differentiated cell type to another desired cell type. An example of transdifferentiation is the changes in a differentiated cell (e.g., human somatic cell in tissue culture), that result upon introduction of one or more transcription factors, growth factors, microRNAs, small molecules, and/or a component of a cell of a different cell type than said differentiated cell (e.g., cytoplasm, nucleoplasm, whole cell extract, or a fraction or component thereof).

"ROCK inhibitors" refer to any substance that inhibits or reduces the function of Rho-associated kinase or its signaling pathway in a cell, such as a small molecule, an siRNA, a miRNA, an antisense RNA, or the like. "ROCK signaling pathway," as used herein, may include any signal processors involved in the ROCK-related signaling pathway, such as the Rho-ROCK-Myosin II signaling pathway, its upstream signaling pathway, or its downstream signaling pathway in a cell. An exemplary ROCK inhibitor that may be used is Stemgent's Stemolecule Y-27632, a rho-associated protein kinase (ROCK) inhibitor (see Watanabe et al., Nat Biotechnol. 2007 June; 25(6):681-6) Other ROCK inhibitors include, e.g., H-1152, Y-30141, Wf-536, HA-1077, hydroxyl-HA-1077, GSK269962A and SB-772077-B. Doe et al., J. Pharmacol. Exp. Ther., 32:89-98, 2007; Ishizaki, et al., Mol. Pharmacol., 57:976-983, 2000; Nakajima et al., Cancer Chemother. Pharmacol., 52:319-324, 2003; and Sasaki et al., Pharmacol. Ther., 93:225-232, 2002, each of which is incorporated herein by reference as if set forth in its entirety. ROCK inhibitors may be utilized with concentrations and/or culture conditions as known in the art, for example as described in US PGPub No. 2012/0276063 which is hereby incorporated by reference in its entirety. Additional examples of the Rho-associated kinase inhibitors include compounds disclosed in the following references: U.S. Pat. No. 4,678,783, U.S. Pat. No. 3,421,217, WO99/20620, WO99/61403, WO02076976, WO02/076977, WO02/100833, WO03/059913, WO03/062227, WO2004/009555, WO2004/022541, WO2004/108724, WO2005/003101, WO2005/039564, WO2005/034866, WO2005/037197, WO2005/037198, WO2005/035501, WO2005/035503, WO2005/035506, WO2005/080394, WO2005/103050, WO2006/057270, WO2007/026664 and the like. Such compounds can be produced according to the method described in each of the respective references. Specific examples include 1-(5-isoquinolinesulfonyl)homopiperazine (fasudil), (+)-trans-4-(1-aminoethyl)-1-(4-pyridylcarbamoyl)cyclohexane (Y-27632) and the like, as well as salts thereof, preferably pharmaceutically acceptable salts such as hydrochloride salts. In exemplary embodiments, the ROCK inhibitor may have a concentration of about 0.05 to about 50 microM, for example, at least or about 0.05, 0.1, 0.2, 0.5, 0.8, 1, 1.5, 2, 2.5, 5, 7.5, 10, 15, 20, 25, 30, 35, 40, 45, or 50 microM, including any range derivable therein, or any concentration effective for promoting cell growth or survival.

EXAMPLES

Examples 1 and 2 illustrate directed differentiation of corneal endothelial cells from embryonic stem cells. Corneal endothelial cells were produced from feeder-free cultures of embryonic stem cells, without the need for embryoid bodies, neural rosettes, or stromal inducer cells. The resulting corneal endothelial cells are expected to be particularly suitable for clinical use because xenogeneic cells were not used in their derivation.

Morphologically, the resulting cells exhibited the hexagonal or polygonal shape and tight adherence to one another that are characteristic of naturally occurring human corneal endothelial cells. Further, analysis by qPCR and immunostaining revealed that these cells express markers indicative of corneal endothelial cells including the Na+K+ATPase pump, ZO-1, and KLF13. Further, these cells were distinguished from vascular endothelial cells (whose marker expression has some overlap with corneal endothelial cells) by the lack of expression of the vascular endothelial cell markers vWF and CD31 (assayed by qPCR and immunostaining), which are typical vascular endothelium proteins, but are not expressed in human corneal endothelial cells. Based on our observations, we concluded that the resulting hESC-derived cells were corneal endothelial cells.

Example 1

Derivation of Corneal Endothelial Cells from Human Embryonic Stem Cells (without Passaging)

Step 1.

Human embryonic stem cells (hESC) were cultured in the absence of feeder cells (specifically, on Matrigel with mTESR1 media). hESC were passaged as clumps (using EDTA or dispase). hESC passaged with dispase were routinely split at a ratio of 1:6 to 1:10 every 5-7 day when large colonies were beginning to touch or about 75% confluency. Typical colony size is significantly larger than with EDTA method, with the colony number around 150 per well in a 6 well culture dish. Passaging was essentially as outlined by manufacturer (Stem Cell Technologies). hESC passaged with EDTA were routinely passaged at a ratio of 1:8-1:12 every 3-5 days when the colonies are beginning to touch or about 75% confluency. Colony size was significantly smaller than the Dispase method, with the colony number around 300 per well in a 6 well culture dish.

mTeSR1 media was prepared as directed by the manufacture, optionally with the addition of antibiotics (e.g., pen-strep at 1× concentration). It is expected that other culture conditions could also be used (which may or may not include use of murine embryonic fibroblasts (MEFs) or other feeder cells), however, it may be preferred to avoid feeder cells (particularly xenogeneic feeder cells) when the resulting cells are intended for clinical use. It is expected that other passaging methodologies could be used (e.g., manually, or using other enzymes such as trypsin, optionally in combination with an inhibitor of Rho-associated kinase (ROCK), such as Y-27632 (Watanabe et al., Nat Biotechnol. 2007 June; 25(6):681-6)).

Step 2.

Cells were grown to approximately the density achieved 1-2 days before they would be ready to be split (timing was determined during routine passaging as described in step 1).

Step 3.

Figure 9:
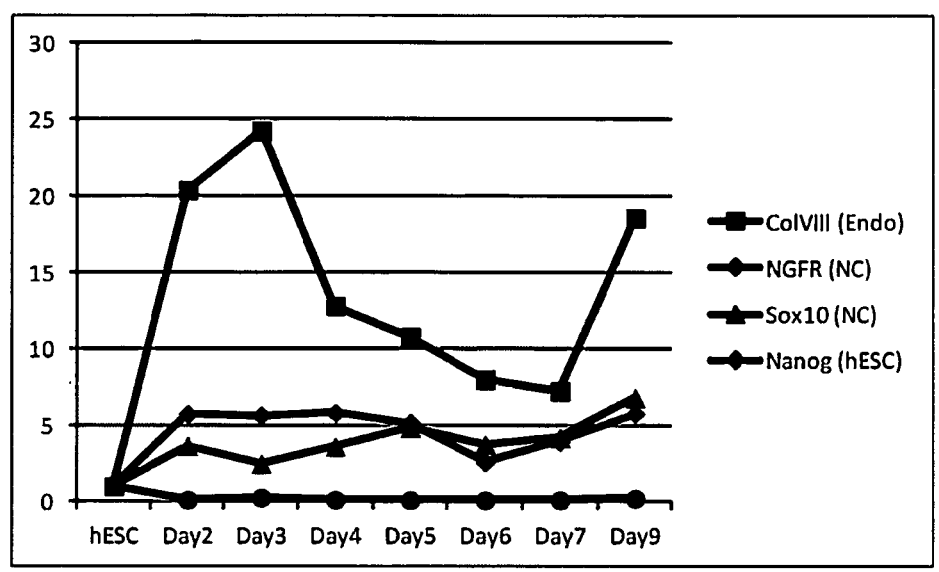
FIG. 9 shows induction of neural crest and corneal gene expression over the course of production of corneal endothelial cells from embryonic stem cells as described in Example 1. Collagen VIII (ColVIII), a corneal endothelium gene, was expressed at high levels after two days of dual SMAD inhibitor exposure. The neural crest genes NGFR and SOX10 were expressed early and maintained during the culture period. Nanog (a gene indicative of pluripotency) was greatly reduced early in the culture process. Gene expression was measured by qPCR on the indicated days of the differentiation protocol or for untreated hESC, as labeled. RQ indicates quantity detected relative to the amount detected from hESCs, i.e., the level of expression in hESC is set to 1. RQ values shown are the average of multiple measurements, with error bars indicating the minimum and maximum of the RQ); values are indicated with square symbols for ColVIII, diamond symbols for NGFR, triangular symbols for SOX10, and circular symbols for Nanog.

Day 0: Medium was changed to dual SMAD medium (see formulation below) containing the dual SMAD inhibitors, Noggin (500 ng/mL human recombinant Noggin, obtained from Peprotech (cat #120-10C)) and SB431542 (10 micromolar SB431542, obtained from Tocris (cat#1614) or Stemgent (cat#04-0010)). As discussed above, Noggin is thought to bind BMP2, BMP4, and BMP7, and SB431542 is thought to block phosphorylation of ACTRIB, TGFβR1, and ACTRIC receptors, and it is envisioned that one or more of the alternative factors discussed above may be used in place of or in addition to Noggin, SB431542, or both. Optionally, formation of neural crest may be monitored, e.g., by detecting the level of mRNA for neural crest markers such as Sox10 and NGFR over time. Elevated expression of these markers was detected about one day after commencing exposure to the dual SMAD inhibitors. In addition, the corneal endothelium marker ColVIII was detected to be upregulated, while expression of Nanog (a marker of pluripotency) was decreased (see FIG. 9).

Step 4.

Day 2: The culture medium was changed to Cornea medium, which included PDGFB and DKK2 (see formulation below). At this point the cells exhausted the culture medium quickly, and fresh Cornea medium was added daily. This was apparently due to high metabolic activity of the cells, which is an expected CEC phenotype and provides further confirmation of the cells' identity. It is envisioned that after some number of days in culture (e.g., after 2, 3, 4, 5, or 6 days, or up to one or two weeks) the cells could be maintained in culture in the absence of DKK2, which may optionally be gradually decreased in concentration and then omitted from the culture medium.

Figure 8:
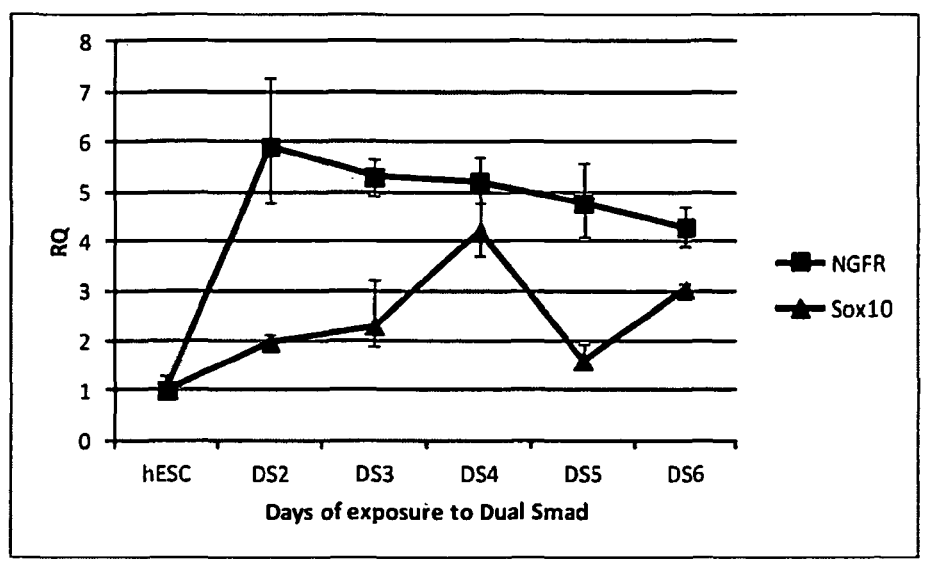
FIG. 8 shows upregulation of the neural crest genes NGFR and Sox10 over the course of six days after commencing exposure of hESC to the dual SMAD inhibitors Noggin and SB431542 (4-[4-(1,3-benzodioxol-5-yl)-5-(2-pyridinyl)-1H-imidazol-2-yl]benzamide). Expression of each gene was markedly increased at day 2 ("DS2") and remained elevated through day 6 ("DS6"). RQ indicates quantity detected relative to the amount detected from hESCs and the endogenous control PGK1 (average of multiple measurements, with error bars indicating the minimum and maximum of the RQ); values are indicated with square symbols for NGFR and triangular symbols for Sox10. Gene expression was measured by qPCR analysis of samples collected on the indicated days (DS2 through DS6 referring to days 2 through 6, respectively, after commencing exposure of hESC to the dual SMAD inhibitors).

It is envisioned that alternatives to PDGF and/or DKK2, including those further described above, could be used instead of, or in addition to, those respective factors. Other components of the media may also include: Angiopoietin like protein 7, Transforming growth factor β2, Hepatocyte growth factor, Keratinocyte growth factor, and Interleukin 1α (again, it is envisioned that potential alternatives, including those identified above, may be used instead of or in addition to one or both of these factors). Though this step was performed at day 2, additional time exposure of cells to the dual SMAD inhibitors did not significantly change the expression of the neural crest genes, NGFR and Sox10 (FIG. 8); therefore, it is expected that exposure of the cells to the dual SMAD inhibitors for longer or shorter durations (e.g., between 1-4 days, up to 6 days, or longer) would likely be acceptable.

Step 5.

Cultures become confluent. At the edges of the colonies, the morphology is altered, cells become larger and shape is more polygonal or hexagonal.

Step 6.

By Day 7: Hexagonal cells can be seen at the contact points of the colonies as well as circular colonies of hexagonal cells scattered throughout the dish.

Step 7.

Figure 3:
FIG. 3A-F shows positive expression and tight junction localization of the marker ZO-1 by corneal endothelial cells differentiated from the hESC line H1GFP that provides confirmation of their corneal endothelial identity. Corneal endothelial cells (CEC) were stained for the tight junction marker ZO-1 (red.
Figure 4:
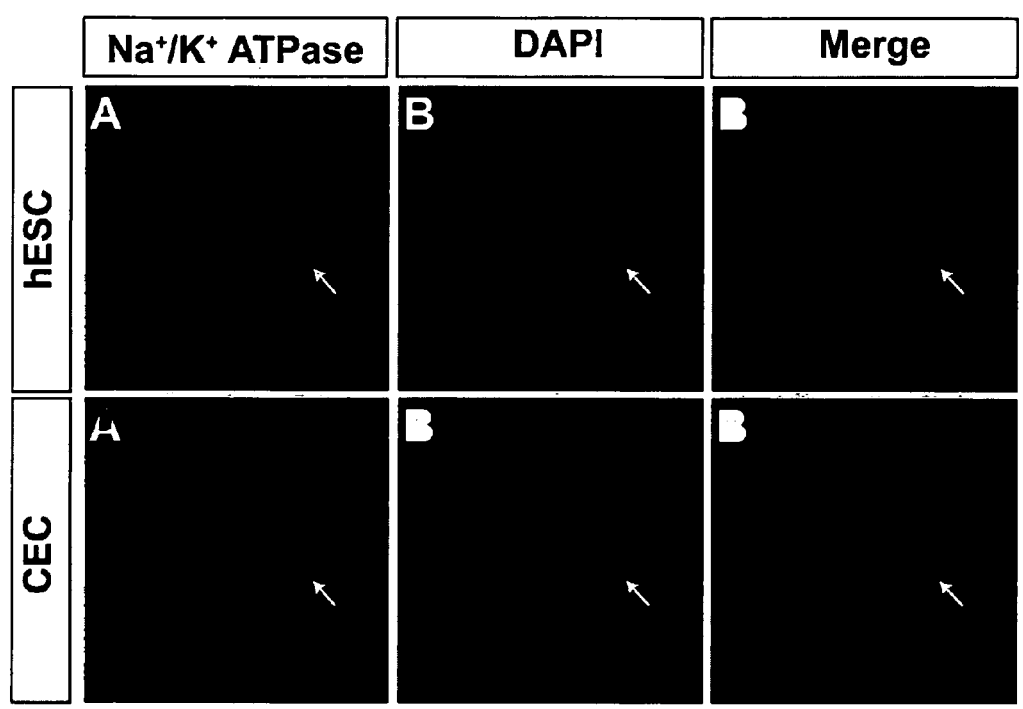
FIG. 4A-F shows expression and localization of the marker Na+K+ATPase by cells differentiated from the hESC line H1GFP that provides confirmation of their corneal endothelial identity. Undifferentiated H1GFP hESCs exhibited a relatively unorganized distribution of Na+K+ATPase (FIG. 4A, Na+K+ATPase staining shown in red.
Figure 6:
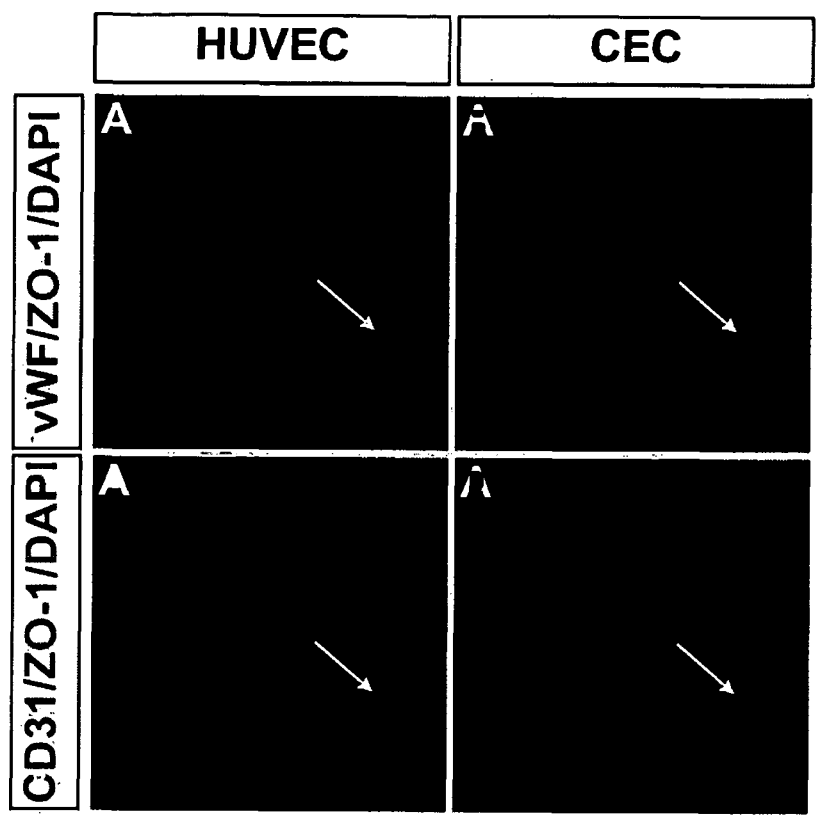
FIG. 6A-D shows the absence of vascular endothelial marker expression from corneal endothelial cells derived from H9 hESCs (CEC). Human vascular endothelial cells (HUVEC) were used as a positive control. Cells were stained for the vascular endothelial cell marker von Wildebrand factor (vWF, red), corneal endothelial cell marker ZO-1 (green), and nuclear stain DAPI (blue). Merged views show that HUVEC (FIG. 6A) were positive for vWF and negative for ZO-1, while CEC (FIG. 6B) were negative for vWF and positive for ZO-1. Cells were stained for the vascular endothelial cell marker CD31 (red), corneal endothelial cell marker ZO-1 (green), and nuclear stain DAPI (blue). Merged views show that HUVEC (FIG. 6C) were positive for CD31 and negative for ZO-1, while CEC (FIG. 6D) were negative for CD31 and positive for ZO-1. The corneal endothelial cells in this figure were produced as described in Example 1 and are shown at day 9. These results demonstrate that the CEC do not detectably express the vascular endothelial markers CD31 and vWF, further confirming their identity as corneal endothelial cells.
Figure 7:
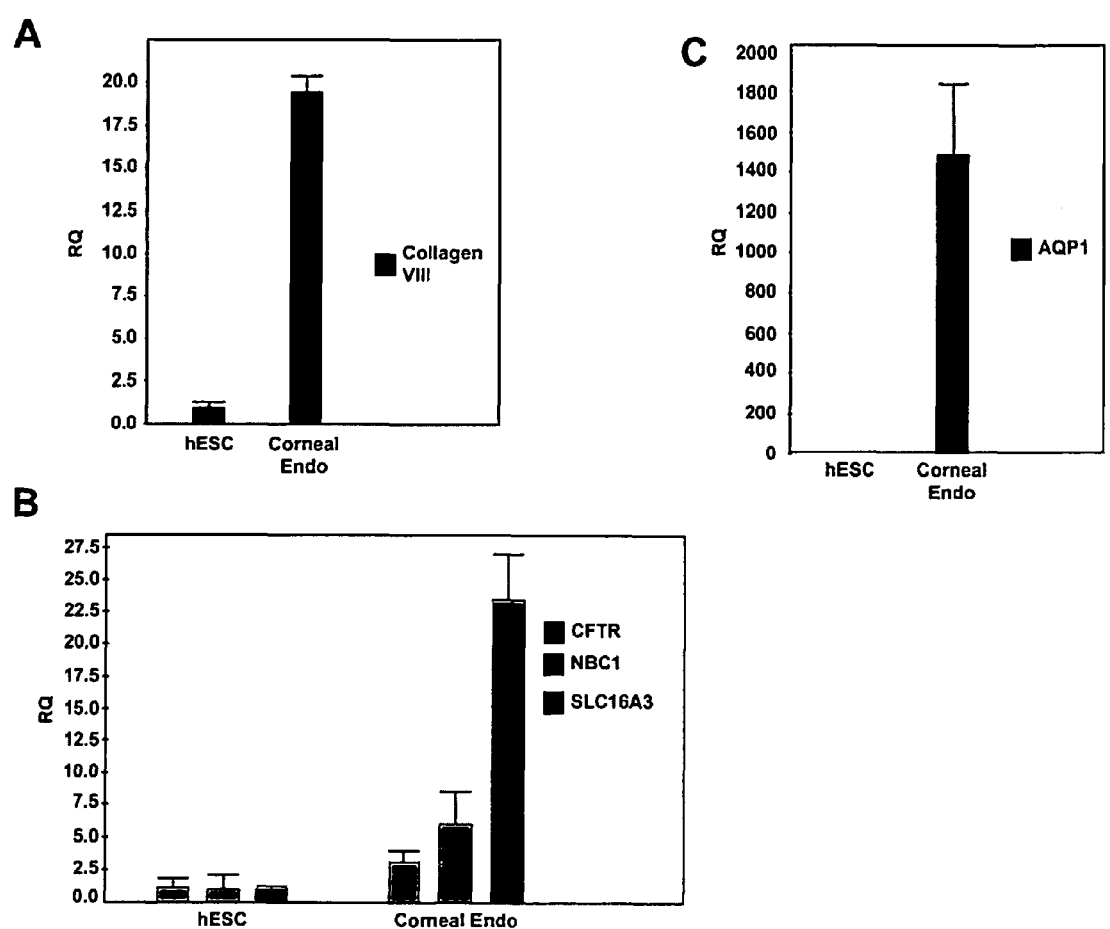
FIG. 7A-C shows upregulation of mRNAs characteristic of corneal endothelial cells differentiated by hESC-derived corneal endothelial cells. Gene expression was detected by qPCR, and normalized to the level of expression detected from hESCs and the endogenous control PGK1. Expression of Collagen VIII, a major component of Descemet's membrane that is secreted by corneal endothelial cells, was upregulated by approximately 20-fold (FIG. 7A); expression of the corneal endothelial cell markers CFTR, NBC1, and SLC16A3 were upregulated by approximately 3-, 6-, and 23-fold, respectively (FIG. 7B, left, center, and right bar in each group, respectively); and expression of AQP1, a major component of a corneal endothelial pump, was upregulated by about 1500-fold. RQ indicates quantity detected relative to the amount detected from hESCs (average of multiple measurements, with error bars indicating the minimum and maximum of the RQ). CEC in this experiment were produced as in Example 1.
Figure 10:
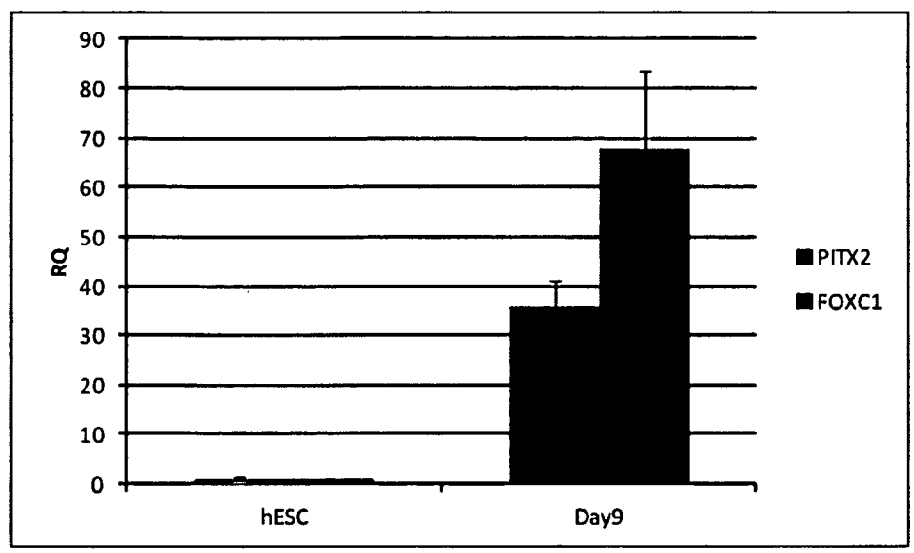

At day 9, the cultures expressed mRNA for collagen 8 (Col8a1 gene), a major component of Descemet's membrane, (FIG. 7A), Na+K+ATPase pump (ATPa1 gene), a major component of endothelium pump function (FIG. 4), as well as the following potential components of the endothelium pump function: Carbonic anhydrase II (CA2), Anion exchanger 2 (AE2/SCL4A2), Solute Carrier Family 16 A1 (SCL16A1), SCL16A3, Carbonic anhydrase 12 (CA12), Carbonic Anhydrase 4 (CA4), cystic fibrosis transmembrane conductance regulator (CFTR). The cells also expressed the transcription factors FoxC1 and Pitx2 which are expressed by ocular neural crest during development and mutations in which can result in corneal abnormalities (FIG. 10). By immunostaining, the cells were ZO-1 (FIG. 3) and Na+K+ ATPase (FIG. 4) positive and expressed at the cell junction. The cells were negative for vascular endothelium cell markers, von Wildebrand factor (VWF) and CD31/PECAM-1 (FIG. 6).

Step 8.

At Day 11 and Day 17, cells surrounding the hexagonal colonies are optionally removed (e.g., manually or by laser ablation) to increase room for hexagonal colonies to expand.

Step 9.

At Day 19, hexagonal cell colonies were dissected in solid sheets and transferred to Matrigel coated glass coverslips for immunostaining and grown to expand colonies.

Step 10.

Figure 5:
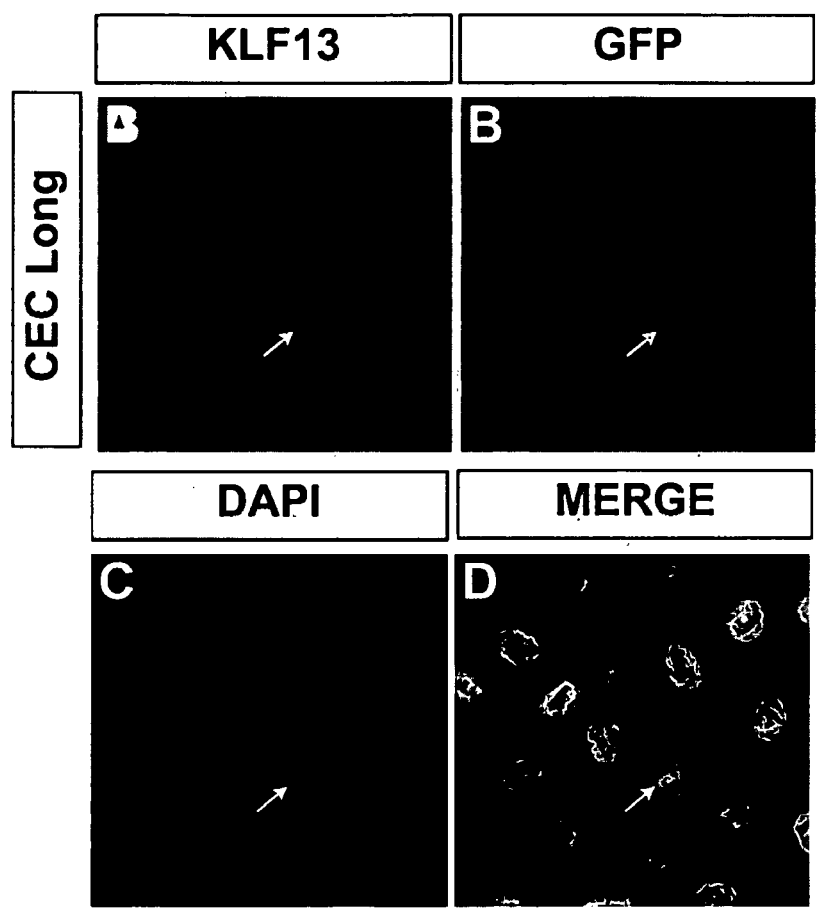
FIG. 5A-D shows expression and localization of the marker KLF13 by cells differentiated from the hESC line H1GFP that provides confirmation of their corneal endothelial identity, and additionally illustrates that the cells adopted a more regular and uniform hexagonal shape after a greater time in culture. Corneal endothelial cells were differentiated from hESCs using as described in Example 1 and are shown after 25 days in culture (CEC Long). Cells were stained for the transcription factor KLF13 (FIG. 5A, red) and with the nuclear stain DAPI (FIG. 5C, blue). GFP fluorescence was also visualized (FIG. 5B, green) and was visible at both the cell nucleus and outlining the boundaries of the cells. Relative to the day 9 cultures, the CEC Long cells had adopted a more regular and uniform hexagonal shape. The merged view (FIG. 5D) shows the expression of KLF13 as expected.

At Day 25, hexagonal cell colonies were collected for analysis, e.g., immunostaining or detection of expressed mRNAs. In addition to the markers described above, cells expressed KLF13 mRNA and protein (a transcription factor expressed in corneal endothelial cells, FIG. 5).

Media Formulations Used in this Example are as Follows:

Modified Wi Medium

80% DMEM-F12 Invitrogen cat #11330-032

20% Knock Out Serum Replacer Invitrogen cat#10828-028 (the composition of which is reportedly described in WO/1998/030679; see Amit et al., Developmental Biology 227, 271-278 (2000)).

1% Non-essential Amino Acids Invitrogen cat#11140-050

1 mM L-glutamine Invitrogen cat#250300-81

0.1 mM b-mercaptoethanol Sigma cat #M7522

6 ng/ml human recombinant FGF2, Invitrogen cat#13256-029

10,000 units of penicillin (base) and 10,000 µg of streptomycin Invitrogen cat#15140122
Dual Smad Medium
80% DMEM-F12 Invitrogen cat #11330-032
20% Knock Out Serum Replacer Invitrogen cat#10828-028
1% Non-essential Amino Acids Invitrogen cat#11140-050
1 mM L-glutamine Invitrogen cat#250300-81
0.1 mM b-mercaptoethanol Sigma cat #M7522
6 ng/ml human recombinant FGF2, Invitrogen cat#13256-029
10,000 units of penicillin (base) and 10,000 µg of streptomycin Invitrogen cat#15140122
500 ng/ml human recombinant Noggin Peprotech cat#120-10C
10 micromolar SB431542 Tocris cat#1614 or Stemgent cat#04-0010
Cornea Media (Modified Wi Medium Containing PDGFB, DKK2, B27)
80% DMEM-F12 Invitrogen cat #11330-032
20% Knock Out Serum Replacer Invitrogen cat#10828-028
1% Non-essential Amino Acids
1 mM L-glutamine (see recipe) Invitrogen cat#250300-81
0.1 mM beta-mercaptoethanol Sigma cat #M7522
6 ng/ml human recombinant FGF2, Invitrogen cat#13256-029
10,000 units of penicillin (base) and 10,000 µg of streptomycin Invitrogen cat#15140122
10 ng/ml human recombinant PDGFB, Peprotech cat#AF-100-14B
10 ng/ml mouse recombinant DKK2 R&D Systems cat #2435-DK-010 (or human recombinant DKK2)
0.1×B27 Invitrogen cat #17504-044

Example 2

Derivation of Corneal Endothelial Cells from Human Embryonic Stem Cells (Replating Method)

Steps 1 to 4 were performed as in Example 1, above; it is expected that the alternative methodologies, factors, and timing discussed therein would be similarly suitable for use with this method.

Step 5.

At Day 3, cells were passaged 1:1. Preferred cell dissociation buffers include ethylenediaminetetraacetic acid solution (EDTA) 0.02% in DPBS (0.5 mM) (Sigma Cat#E8008-100ML), Cell Dissociation buffer (Invitrogen cat#13151-014) and Gentle Cell Dissociation Buffer (Stemcell Technologies cat #07174). Additional exemplary cell dissociation buffers that may be used include: Enzyme Free Cell Dissociation Solution PBS Based (Millipore cat#S-014-C), Cell Dissociation Solution Non-enzymatic (Sigma cat#C5789), Cellstripper (Cellgro cat#25-056-CI).

Passaging was effected using EDTA as follows: 1 ml of buffer was added and the plate was left undisturbed for 9-12 minutes. Cells were checked for signs of detachment by light microscopy. Cell dissociation buffer was then aspirated. Cornea cell medium was then added in a dropwise fashion to gently lift the cells from the plate. No agitation was needed to remove cells. The dissociated cells were then transferred to a 15 ml falcon tube. Remaining cells in the dish were rinsed with additional corneal cell medium and added to the 15 ml falcon tube. Cells are then appropriated diluted at a range of 1:1-1:5 and transferred to new wells of Matrigel coated plates.

Though this step was performed two days after addition of Dual SMAD inhibitors and one day after addition of PDGFB and DKK2, it is expected that the timing of this step could be altered. Some cells remained adherent and produced corneal endothelial cells with comparable efficiency as in Example 1 (when further cultured as from steps 5 onward of Example 1). The removed cells, however, were plated (in the same medium as in Step 4) and formed corneal endothelial cells more quickly and uniformly than the cultures of Example 1; properties and characterization of these cells are the subject of the remaining steps.

Step 6.

At Day 8, cultures contained large numbers of hexagonal cells with smaller patches of putative progenitor cells (distinguished based on non-polygonal morphology) interspersed.

Step 7.

At Day 10, the plate contained mostly hexagonal cells with very small ball-like colonies of putative progenitor cells. Cell expressed the same markers as described above in Example 1 (including CA2, SCL4A2, SLC16A1, SLC16A3, CA12, CA4, and CFTR). Expression of additional pump mRNAs were also detected: Aquaporin 1 (AQP1), Sodium Hydrogen exchanger (NHE1) and Sodium Bicarbonate transporter (NBC-1) (Table 1, FIG. 7B, C).

The resulting hESC-derived CEC were then evaluated by qPCR for expression of pump genes indicative of CEC identity. The cultures were positive for expression of all 12 pump genes tested. In initial experiments the expression of only 10 out of the 12 pump genes was detected, however, use of different PCR primers permitted detection of expression of the remaining two pump genes.

TABLE 1 hESC derived corneal endothelial cells expressed 12 out of 12 corneal pump markers (detected by qPCR). Expression levels are denoted "high," "medium," or "low" based on the Ct value (the cycle number at which abundance of the RT-PCR product exceeded a threshold level that is within the exponential phase of amplification; lower values indicate greater abundance).

| Relative Expression levels | Pump markers | Ct Value |
| --- | --- | --- |
| High | AQP1 | 26 |
|  | CA2 | 29 |
|  | SCL4A2 | 29 |
|  | SLC16A1 | 26 |
|  | SLC16A3 | 28 |
| Medium | ADCY10 | 33 |
|  | CA12 | 33 |

TABLE 1-continued hESC derived corneal endothelial cells expressed 12 out of 12 corneal pump markers (detected by qPCR). Expression levels are denoted "high," "medium," or "low" based on the Ct value (the cycle number at which abundance of the RT-PCR product exceeded a threshold level that is within the exponential phase of amplification; lower values indicate greater abundance).

| Relative Expression levels | Pump markers | Ct Value |
|---|---|---|
| | CA4 | 32 |
| | CFTR | 34 |
| | NBC1 | 33 |
| | NHE1 | 31 |
| | SCL16A7 | 32 |

Example 3

Cultured CEC Produce a Matrix Similar to Descemet's Membrane

This example describes production of a gel-like matrix from media conditioned by a culture of hES-derived CEC. These results indicate that the CEC secrete one or more factors that can form a gel, which Applicants hypothesize include components of Descemet's membrane (which is produced by CEC in vivo). Particularly, as shown above, the CEC strongly upregulate expression of ColVIII (a component of Descemet's membrane), suggesting that secreted ColVIII is a component of the observed matrix. Western blotting was performed to confirm that the matrix indeed contained COL8A1 and COL8A2 proteins. Moreover, a matrix produced from factors secreted by the CEC may be used as a CEC culture substrate and/or as a carrier to be used during cell transplantation.

Corneal endothelial cells were produced from hES cells as described in the preceding examples and cultured. Conditioned cell medium was removed from corneal endothelial cultures after at least one day of culture from two wells in a 6-well plate. The combined volume was 8 mLs. The conditioned cell medium was centrifuged to remove cell debris and other large fragments. Medium was centrifuged for 5 min at 1000×g and 10° C. to remove cell debris. Supernatant was added to an Amicon Ultra 15 with a 10,000 Da molecular weight cut-off (MWCO). The medium was concentrated in this device by centrifugation in a Beckman Coulter Allegra X-15R with a swinging bucket rotor (two spins at 4000×g for 15 min at 4° C.), and the volume was reduced from 8 mLs to ~500 µL. For SDS-PAGE analysis, 32 µL of the concentrated medium was removed and added to an SDS-containing solution with a final concentration of 30 mM Tris-HCl, 1% SDS, and 10% glycerol. Upon heating this solution to 95° C. for 2 min, the solution appeared brown in color and had polymerized into a gel-like semi-solid.

It is thought that the SDS solution was not necessary for polymerization; rather, concentrated media may optionally be polymerized with or without additional components such as the cornea media, a basal culture medium, additional growth factors or other matrix proteins, etc. Moreover, it is expected that similar results may be achieved using other concentrators (e.g., 10K Spin Column, BioVision; Vivaspin, Sartorius Stedim; and 10K Spin Column, MBL International, etc.) or other concentration method (e.g., pressure ultrafiltration, evaporation, dialysis against glycerol, and others). Incubation time and temperature may be varied to permit the gel to form, for example at temperatures ranging from 37° C. to 95° C. and durations between 0.5 minutes to overnight. After polymerization, liquid may be removed. CEC may be cultured on the resulting matrix, e.g., seeded directly on the matrix, which (prior to, during, or subsequent to polymerization) may be supplemented with DKK2, PDGFB, and/or other factors that contribute to growth.

Figure 19:
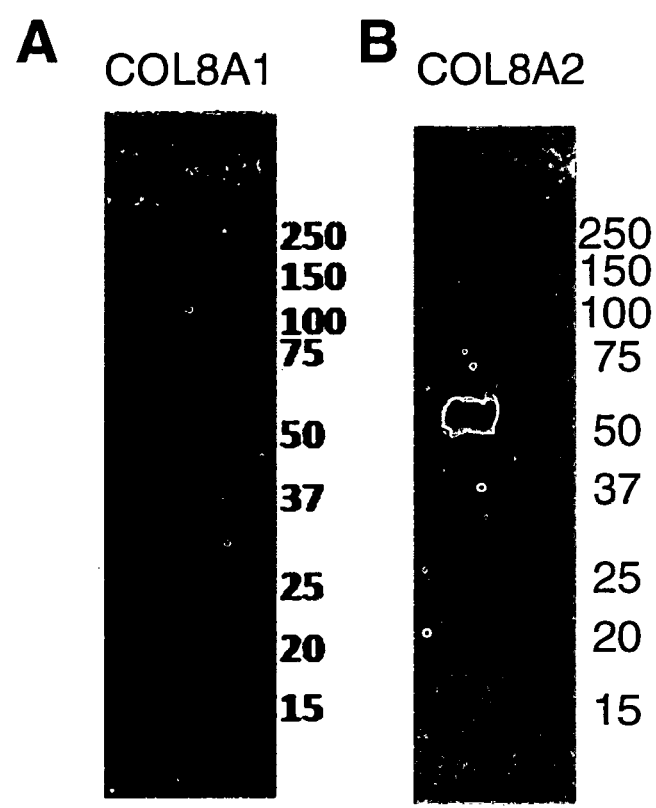
FIG. 19. COL8A1 and COL8A2 are secreted to form an extracellular-like matrix by hESC derived CEC. The underlying subcellular matrix below the hESC CEC was collected and analyzed by Western Blot. A. COL8A1 is present as detected in an approximate 50 kDa band in the subcellular matrix. A band greater than 250 kDa was detected, and is likely insoluble. B. COL8A2 is present as detected in an approximate 50 kDa band in the subcellular matrix.

The protein constituents of the matrix were further confirmed by Western blotting to detect the presence of COL8A1 and COL8A2 proteins. Cells were removed and lysed from the subcellular ECM using Ammonium Hydroxide as described previously (Sugino et al., 2010). This allowed removal of the CEC without damaging the extracellular matrix that was secreted below the cells. After exposure to the ammonium hydroxide, the plate was washed three times with PBS to dislodge any remaining cells. Reducing sample buffer was then added to collect the extracellular matrix protein. Standard SDS PAGE and Western blotting was performed using antibodies to COL8A1 (FIG. 19A) and COL8A2 (FIG. 19B), and both proteins were detected, indicating that these proteins were secreted by the hESC-derived CEC to form an extracellular-like matrix.

Example 4

Influence of Harvest Methods on CEC Yield, Morphology, and Marker Expression

This example tests the effect of various harvest methods on CEC morphology, yield, and marker expression, which are potentially indicative of the suitability of the cells for transplantation.

CEC were produced as described in Example 2 and harvested using each of the methods enumerated in Table 2, i.e., manually, using trypsin (with differing time and concentration), trypsin in combination with cell dissociation buffer, Accutase, Collagenase B, Collagenase B in combination with cell dissociation buffer, or cell dissociation buffer alone. Cells were replated for one week and then analyzed microscopically for morphology and yield (indicated by whether confluent cultures were subsequently obtained). Additionally, expression of the markers COL8A1 and AQP1 was determined by qPCR. Results are summarized in Table 2.

TABLE 2

Influence of dissociation methods on CEC yield, morphology, and marker expression. CEC were produced as described in Example 2 and harvested using the method indicated in each row. Under "Morphology," "+" indicates polygonal or hexagonal cell shape, "−" indicates fibroblastic morphology, and "+/−" indicates a mixture of polygonal and fibroblastic morphology. "Confluent" indicates that the culture exhibited an uninterrupted solid sheet of cells ("+"), or did not ("−") after one week in culture subsequent to plating. The columns COL8A1 and AQP1 indicate the level of mRNA expression of these respective genes as detected by QPCR relative to PD1T cells; "+" indicates comparable levels and "+/−" indicates reduced mRNA levels.

| Dissociation Method | Morphology | Confluent | COL8A1 | AQP1 |
|---|---|---|---|---|
| Manual | − | − | + | +/− |
| 0.05% Trypsin | + | + | + | +/− |
| 0.25% Trypsin 5 min | + | + | + | + |
| 0.25% Trypsin 10 min | + | + | + | + |
| 0.25% Trypsin: Cell Diss. Buffer 1:1 | + | + | + | + |
| Accutase | − | − | + | + |
| Collagenase B o/n | − | − | + | +/− |
| Collagenase B 1 hr + Cell Diss. Buffer | +/− | + | + | + |
| Cell Diss. Buffer | +/− | − | + | + |

Figure 14:
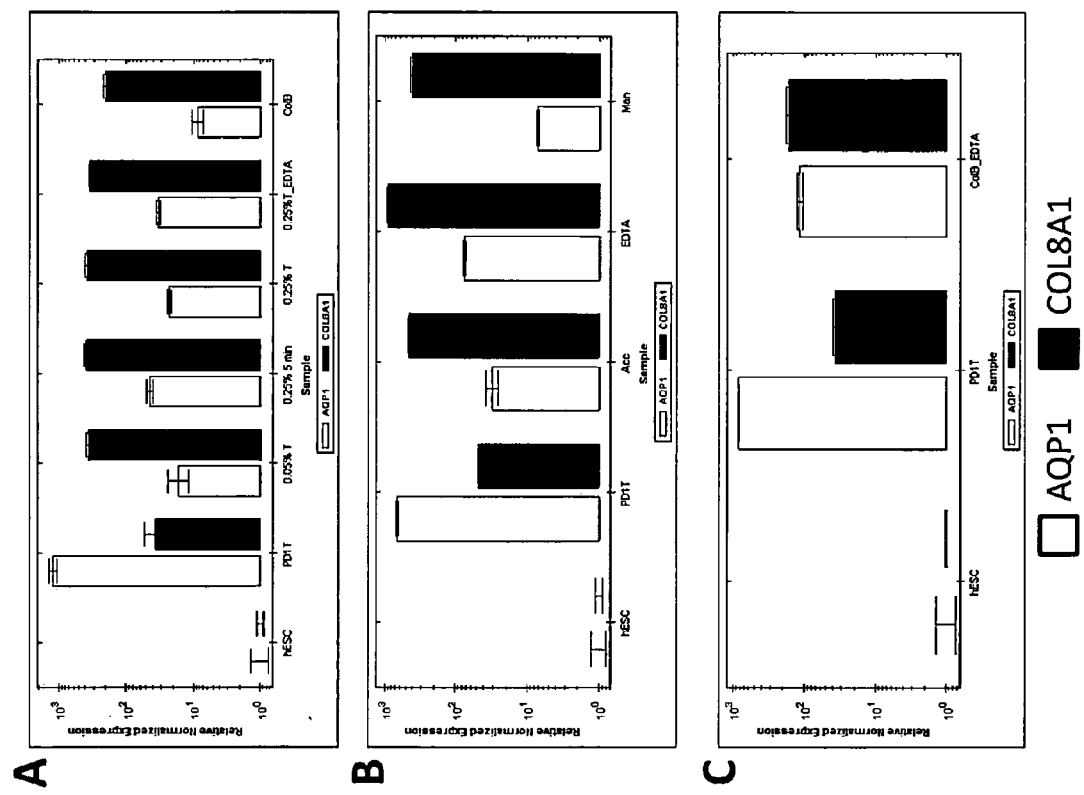
FIG. 14A-C. Expression of AQP1 (left column in each group) and COL8A1 (right column in each group) mRNA by hESC-derived CEC (generated using the method of Example 2) differed depending on the method used for harvesting the cells. Expression levels of these genes were detected using qPCR and normalized to stem cells (hESC) and compared to hESC derived corneal endothelial cells generated using the method of Example 2 prior to harvest (PD1T). All methods of harvesting increased levels of COL8A1 and decreased amounts of AQP1 compared to cells prior to harvesting. Man=manual dissociation (cell scraping); "0.05% T"=0.05% Trypsin; "0.25% 5 min"=0.25% Trypsin for 5 minutes; "0.25% T"=0.25% Trypsin for 10 minutes; "0.25% T_EDTA"=0.25% Tryspin diluted 1:1 with Cell Dissociation buffer, Acc=accutase, ColB=collagenase B overnight; ColB_EDTA=Collagenase B treatment 1 hr followed by cell dissociation buffer.

AQP1 and COL8A1 mRNA levels were also tested by qPCR (FIG. 14A-C). AQP1 and COL8A1 levels were elevated in each instance relative to hESC. However, compared to cells which had not been harvested (produced as in Example 2), all harvesting methods resulted in decreased expression levels of AQP1 and increased expression levels of COL8A1.

Based on these results, use of trypsin (alone or in combination with cell dissociation buffer) can produce high-quality CEC potentially suitable for transplantation. Other methodologies may potentially affect cell morphology after one week of culturing, however, this may or may not adversely affect cell function or suitability for transplantation.

Methods

CEC were derived as described in Example 2 and then harvested under different experimental conditions further described below. All enzymatic harvesting methods included a rinse with Phosphate buffered saline (Life Technologies cat#14190-250) before enzymatic digestion. Cells were then harvested by the following methods and then plated onto a Matrigel plate and cultured for an additional week. Cells were analyzed for their morphology: polygonal, a mixture of polygonal and fibroblastic, and fibroblastic. The cells were analyzed to see if they were able to return to 100% confluency after harvesting and replating. After the week of culture, the RNA was collected and analyzed for the expression of COL8A1 and AQP1 by QPCR.

For "Manual" dissociation, a fine glass dissecting tool was made from a Pasteur pipet under a flame. Under a dissecting scope and sterile hood, sections of corneal endothelial cells were gently peeled from the plate. Cells were then transferred to a new plate to test for viability after removal.

For "0.05% Trypsin" dissociation, 0.05% Trypsin-EDTA (1×), Phenol Red Life technologies cat #25300-054 was used. Cells were treated with 0.05% trypsin at 37 degrees C. for 10 minutes. Cells were then triturated with the trypsin solution to remove cells from well. The enzymatic digestion was stopped with the addition of cornea media. Cells were then centrifuged to pellet cells, resuspended, and plated onto a fresh matrigel plate.

For "0.25% Trypsin" dissociation, 0.25% Trypsin-EDTA (1×), Phenol Red Life technologies cat #25200056 was used. Cells were treated with 0.25% trypsin at 37 degrees C. for 5 or 10 minutes, and treated as described above for 0.05% Trypsin.

For "0.25% Trypsin: Cell dissociation buffer 1:1" 0.25% Trypsin-EDTA (1×), Phenol Red Life technologies cat #25200056 and Cell Dissociation Buffer, enzyme-free, PBS Life technologies cat #13151-014 were used. Cells were treated with 1:1 dilution of 0.25% trypsin and Cell dissociation buffer at 37 degrees C. for 15 minutes, and treated as described above for 0.05% Trypsin.

For "Accutase" treatment, ACCUTASE™ Cell Detachment Solution, Stem cell technologies cat #07920 was used. Cells were treated with Accutase at 37 degrees C. for 25 minutes, and treated as described above for 0.05% Trypsin.

For "Collagenase B" treatment, cells were treated with collagenase B (2 mg/ml) at 37 degrees C. for overnight, and treated as described above for 0.05% Trypsin.

For "Collagenase B+Cell dissociation buffer" cells were treated with collagenase B (1 mg/ml) at 37 overnight C for 1 hr. The collagenase B was then replaced with Cell dissociation buffer (see above) at 37 degrees C. for 10 minutes and treated as described above for 0.05% Trypsin.

For "Cell Dissociation Buffer", Cell Dissociation Buffer, enzyme-free, PBS Life technologies cat #13151-014 was used. Cells were treated with cell dissociation buffer at 37 degrees C. for 1 hr, and treated as described above for 0.05% Trypsin.

Example 5

CEC Cell Density

This example quantifies the density of CEC cultures produced from hESC as described in Example 2. CEC were stained with ZO-1 to confirm identity and manually counted in random fields. From two separate experiments, three random 40× fields were counted. The density of the cultured corneal endothelial cells was 7605±379 cells/mm$^2$ (mean±SEM). This is higher than the reported CEC cell density even for infants (i.e., 5624 cells/mm$^2$) and well in excess of the low density levels associated with dysfunction (e.g., lower than about 500 to 1000 cells/mm$^2$). See Peh et al., Transplantation. 2011 Apr. 27; 91(8):811-9). These results indicate that the subject methods can be used to produce sheets of cells having a density well above the level associated with in vivo corneal function.

Methods hESC corneal endothelial cells were grown on matrigel coated coverslips for 1 week. Immunostaining was performed as previously described with an antibody to ZO-1. After immunostaining, nuclei were detected by exposing the coverslips to DAPI. ZO-1 staining was used to identify corneal endothelial cells, and pictures of the DAPI staining for the same field were taken and counted. Cell number was manually counted in the program Image J 1.45 s (NIH). The area of the 40× field was calculated by measuring the size of a 0.1 mm reference and the area of the 40× field of view was calculated to by 0.0767 mm$^2$. Cell counts were divided by 0.0767 mm$^2$ to obtain the number of cells/mm$^2$.

Example 6 hESC-Derived CEC Gene Expression and Morphology Over Prolonged Culture

Figure 11:
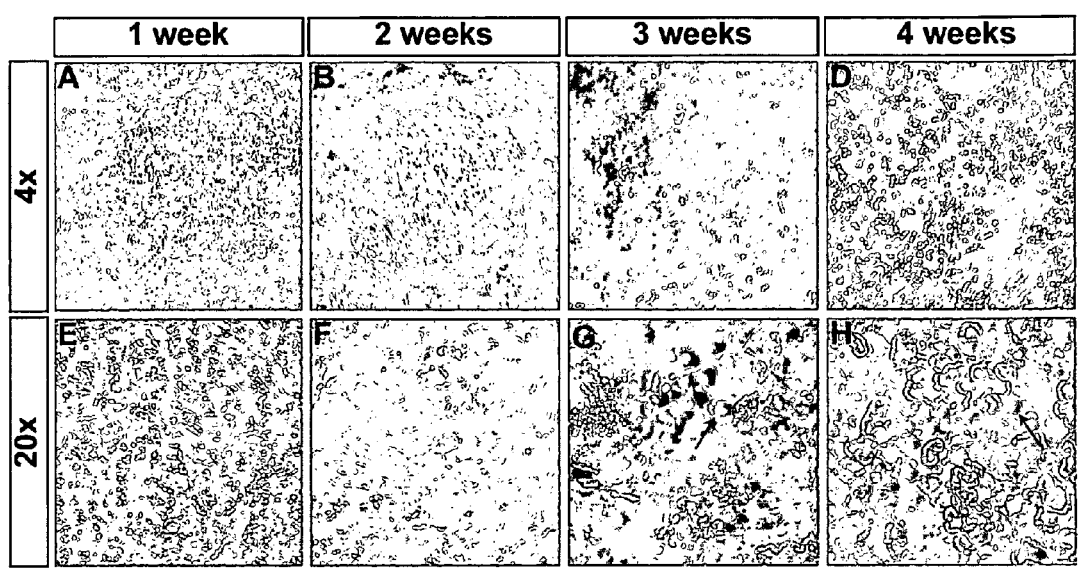
FIG. 11. Polygonal shape continues to refine with time. Phase contrast pictures at low (4×, panels A-D) and high power (20×, panels E-H) of hESC derived corneal endothelial cells after increasing time in culture for cells produced as described in Example 2. A., E. Polygonal hESC derived corneal endothelial cells are clearly visible after 1 week of differentiation. B., F. Cell shape continues to become more regular at 2 weeks of differentiation. C., G. The cells were more uniform in size and shape at 3 weeks differentiation. D., H. Even greater uniformity of cell shape is present at 4 weeks of differentiation.
Figure 13:
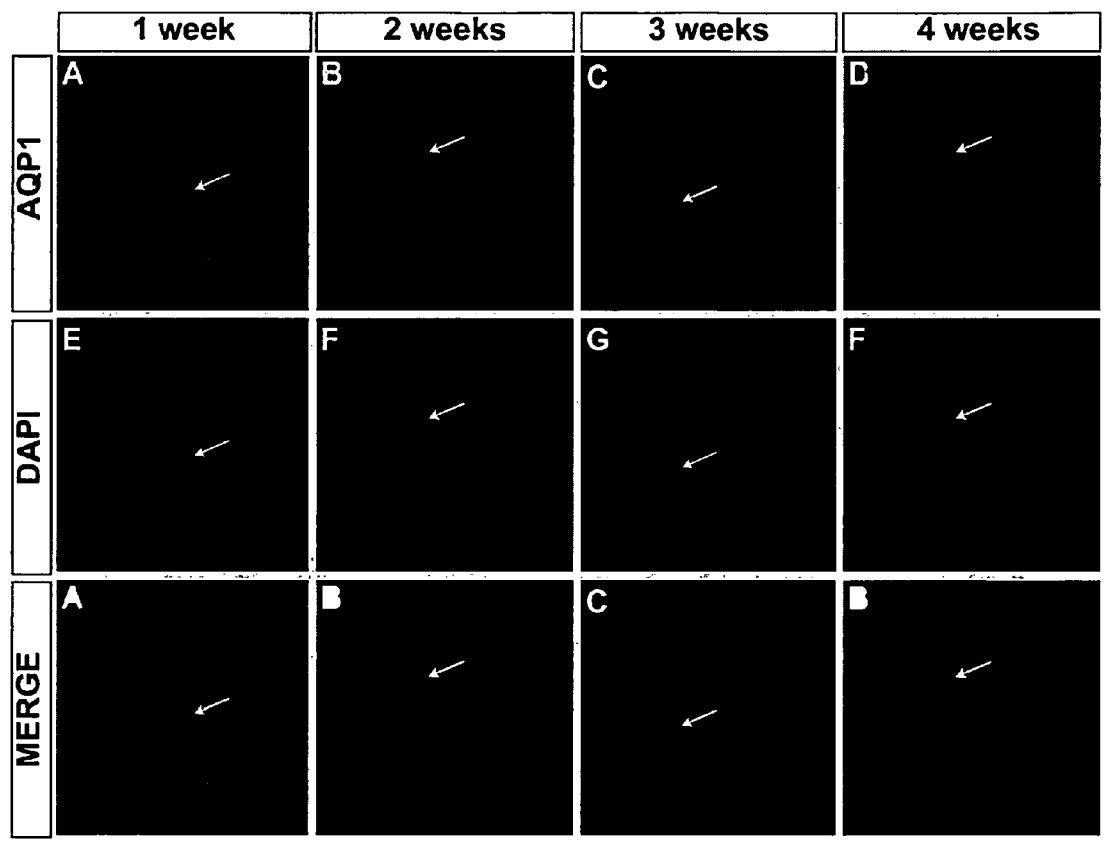
FIG. 13. hESC derived corneal endothelial cells express the water pump Aquaporin1 (AQP1), indicative of CEC identity. AQP1 (red) was localized to the cell borders at all time-points examined. Nuclei were stained with DAPI (blue). Arrows indicate hexagonal cell. A, E, I. 1 week of differentiation. B, F, J. 2 weeks of differentiation. C, G, K. 3 weeks of differentiation. D, H, L. 4 weeks of differentiation. Consistent with mRNA expression levels shown below (see FIG. 15), AQP1 protein was present between weeks 1 and 4.

This example further characterizes the morphology and gene expression of CEC cultures produced from hESC as described in Example 2.

morphology observable in FIG. 11, the tight junctions became more uniform in appearance over the four weeks depicted. AQP1 expression was detected at the cell borders as expected (FIG. 13) at each time point.

Figure 15:
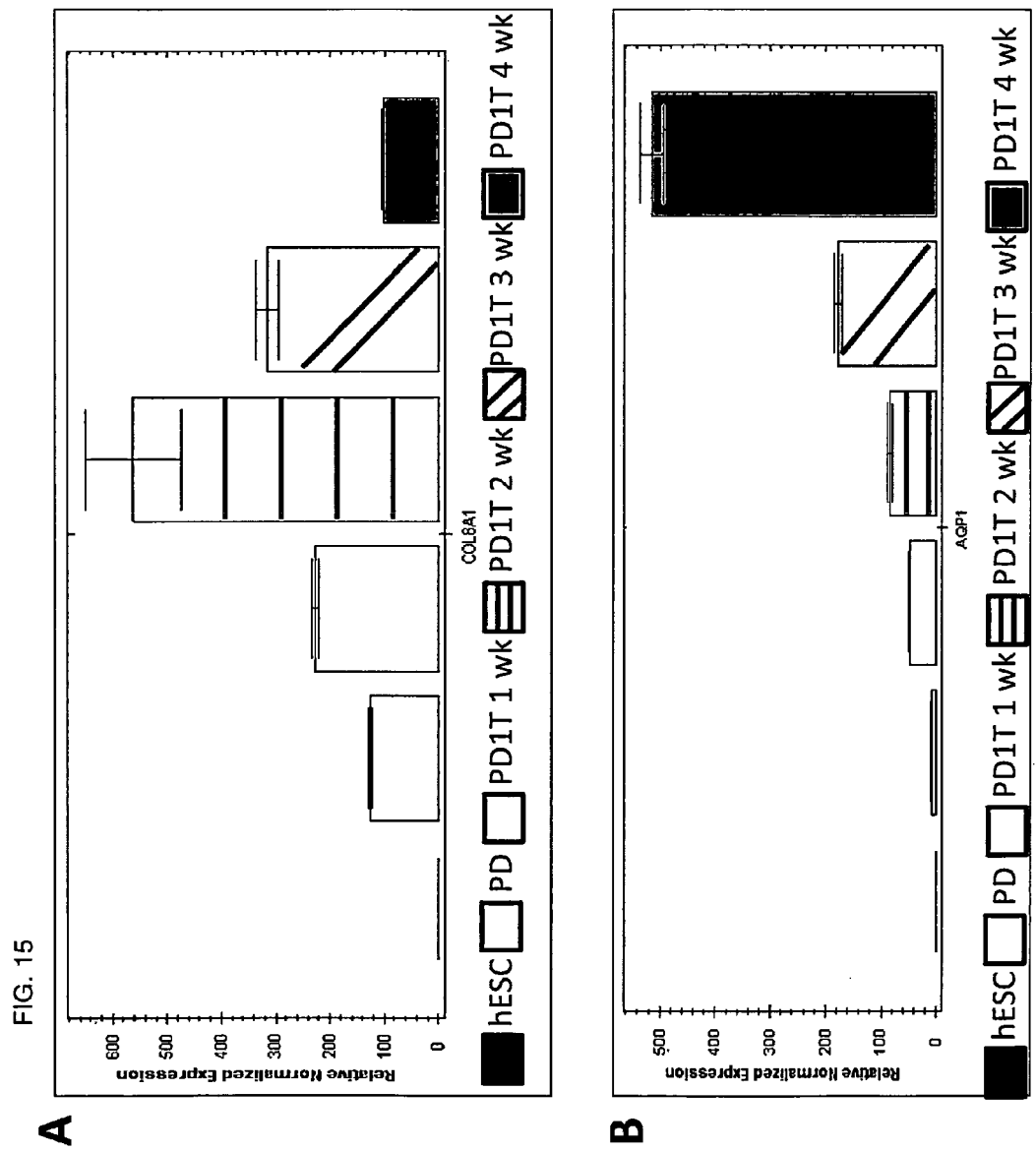
FIG. 15. COL8A1 and AQP1 mRNA levels in hESC CEC cultured for 1-4 weeks. All samples were normalized to stem cells (hESC). "PD" indicates cells produced as in Example 1, i.e., without passaging during differentiation. "PD1T" indicates cells produced as in Example 2, i.e. with the replating step during differentiation. A. COL8A1 was highly expressed at all time-points tested. The temporary increase in COL8A1 expression detected at week 2 coincides with the transfer to a new tissue culture well and is thought to reflect the production of extracellular matrix. B. AQP1 mRNA expression increased with time in culture as the cells matured and paralleled the time-course of adoption of hexagonal morphology as illustrated in FIG. 11 above.

CEC cultures were also tested for the level of AQP1 and COL8A1 mRNA expression at each week between weeks 1 and 4. Both COL8A1 (FIG. 15A) and AQP1 (FIG. 15B) were highly expressed at all time points (normalized to hESC). AQP1 expression increased monotonically over the four week course of the experiment and paralleled the time-course of adoption of hexagonal morphology as illustrated in FIG. 11. COL8A1 was highly expressed at all time-points tested. The temporary increase in COL8A1 expression detected at week 2 coincided with the transfer to a new tissue culture well and is thought to reflect the production of extracellular matrix. Many pumps mRNA increased expression relative to hESC. However, the expression of some pumps remained similar to hESC, indicating that these pumps may be expressed in hESC and/or may be subject to post-transcriptional regulation. Table 3 summarizes the CEC pump expression results.

TABLE 3

Summary of Cornea gene expression levels detected by qPCR. The three groups of genes indicate increased pump expression versus hESC ("Pumps Upregulated"), pumps expressed at similar levels in hESC and CEC ("Pumps Present"), and expression of Collagen8 genes. High (24-28), medium (29-33), and low (34-36) are indicative of raw Ct values, with lower the Ct value reflecting a greater amount of mRNA.

| Pumps present in CEC and upregulated relative to hESC | | | |
| --- | --- | --- | --- |
| Gene | High | Medium | Low |
| AQP1 | + | + | |
| CA2 | + | | |
| CA4 | + | | |
| SLC16A3 | + | | |
| CFTR | | + | |
| SLC16A7 | | + | |
| SLC4A4 | | + | |

| Pumps present in CEC and hESC | | | |
| --- | --- | --- | --- |
| Gene | High | Medium | Low |
| AQP1 | + | + | |
| CA2 | + | | |
| CA4 | + | | |
| SLC16A3 | + | | |
| CFTR | | + | |
| SLC16A7 | | + | |
| SLC4A4 | | + | |

| Collagen 8 Genes | | | |
| --- | --- | --- | --- |
| Gene | High | Medium | Low |
| COL8A1 | + | | |
| COL8A2 | | + | |

Cells morphology was monitored over 4 weeks after differentiation (FIG. 11). Hexagonal cell shape continued to develop and improve over the four week course, with a high degree of uniformity of cell shape being present at week 4.

Figure 12:
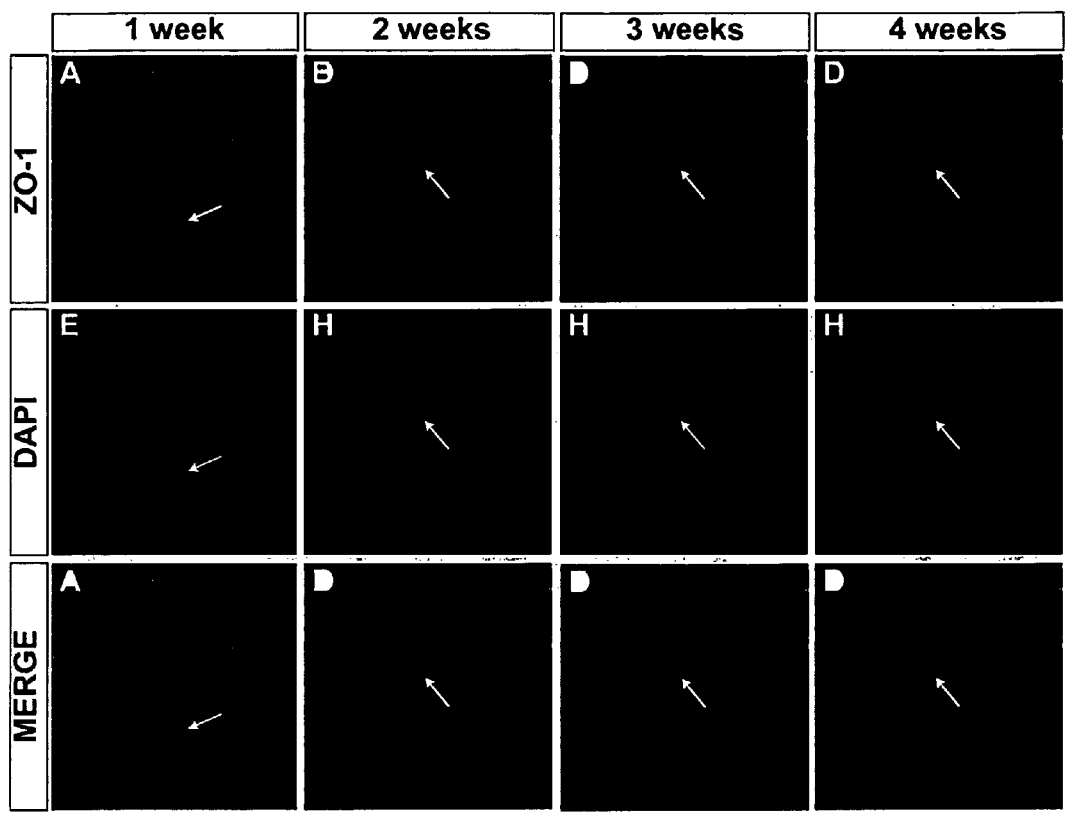
FIG. 12. Tight junctions are present in hESC derived corneal endothelial cells. ZO-1 (red) outlines the tight junctions between corneal endothelial cells. Nuclei are stained with DAPI (blue). Arrows indicate hexagonal cell. A, E, I. As expected, ZO-1 was present at generally uniform intensity at the junctions between cells, and cells contained a single stained nucleus. ZO-1 positive cells were polygonal after 1 week of differentiation. B, F, J. Polygonal ZO-1 cells continued to be present with some variation in cell size at 2 weeks of differentiation. C, G, K. After 3 weeks of differentiation, the CEC became more regular in size and increasing numbers of hexagonal cells appeared in the culture, indicating a switch from polygonal to hexagonal morphology. D, H, L. After 4 weeks of differentiation, refinement of tight junctions between cells continued and increasing numbers of hexagonal cells were observed.

Additionally, CEC cultures were stained for expression of the CEC protein markers ZO-1 and AQP1 at each week between weeks 1 and 4. As expected, ZO-1 expression was detected at the tight junctions between CEC (FIG. 12). In parallel with the adoption of highly uniform hexagonal Example 7

Effect of ROCK Inhibitor

This example demonstrates that addition of a rho-associated protein kinase ("ROCK") inhibitor can improve post-harvest plating cell quality. hESC-derived CEC were harvested with or without the addition of a ROCK inhibitor and/or ASC2P vitamin C isoform ("ASC") and examined for morphology and gene expression after plating. A dose-responsive improvement in cell uniformity and polygonal/hexagonal morphology was observed for ROCK inhibitor concentrations up to 20 micromolar (FIG. 17A-D). Expression of COL8A1 and SLC16A3 were elevated relative to hESC (FIG. 17E-F).

The harvested cells were further examined for morphology, ability to reestablished a confluent culture, and retaining expression of the CEC markers COL8A1, AQP1, and SLC16A by qPCR. The results demonstrate that treatment with ROCK inhibitor can help maintain cell morphology, particularly when ROCK inhibitor is present when the cells are replated after harvesting. Moreover, Maintenance with media containing ROCK inhibitor can help the cells maintain a high quality CEC morphology after harvesting and replating.

For the "Pretreatment" paradigm, CEC were produced as described in Example 2. The cornea media was removed and replaced with either 10 microM Rock or 10 microM Rock with 0.3 mM ASC-P2 (L ascorbic acid phosphate magnesium salt n-hydrate (Wako, cat#013-19641)) for 1 hour before harvesting. Cells were harvested using 0.25% trypsin as described above, however, no Rock inhibitor was added during harvesting.

For the "Rock overnight" paradigm, CEC were produced as described in Example 2, harvested with 0.25% trypsin as described above, and then plated overnight in the presence of 10 microM Rock inhibitor. The following morning, the media was removed, and no further Rock inhibitor was added to the media.

For the "Rock maintenance" paradigm, CEC were produced as described in Example 2, harvested using 0.25%

TABLE 4

Rock inhibitor can improve cell survival after harvesting. The ROCK inhibitor Y-27632 and/or ASC2P vitamin C isoform ("ASC") was added to hESC-derived CEC as indicated under "Treatment," and harvested cells were evaluated based on their morphology and gene expression after replating. "O/N confluent" indicates the confluence of cultured cells after overnight plating, reflecting the degree of cell survival and/or attachment. Morphology indicates the appearance of the cultured cells after 1 week in culture which was recorded as a high quality polygonal/hexagonal cell shape ("++"), a polygonal/hexagonal shape ("+"), or fibroblastic morphology ("−"). COL8A, AQP1, SLC16A3 indicate expression ("+") or non-expression ("−") of the respective mRNAs, as detected by QPCR.

| Treatment | O/N Confluent | Morphology | COL8A1 | AQP1 | SLC16A3 |
|---|---|---|---|---|---|
| Rock Pretreat | − | − | + | + | + |
| Rock + ASC Pretreat | − | − | + | + | + |
| Rock o/n | + | + | + | + | + |
| Rock + ASC o/n | + | + | + | + | + |
| Rock 1 microM (maint.) | + | + | + | + | + |
| Rock 5 microM (maint.) | + | ++ | + | + | + |
| Rock 10 microM (maint.) | + | ++ | + | + | + |
| Rock 20 microM (maint.) | + | ++ | + | + | + |
| Rock 10 microM + ASC (maint.) | + | ++ | + | + | + |
| Rock 20 microM + ASC (maint.) | + | ++ | + | + | + |
| Rock, Rock + ASC (D1) | + | − | ND | ND | ND |

ND = not determined.
Abbreviations: o/n = overnight.
ASC = ASC2P vitamin C isoform added to culture at 0.3 mM,
maint. = maintaining (i.e., the indicated factors were included in culture media on each day after plating),
D1 = indicated factors were included in the culture media for the first week after plating and were thereafter omitted.

Methods

Rock inhibitor Y-27362 (Wako, cat #253-00513) was dissolved in distilled H2O to make a 10 mM stock solution and sterile filtered and aliquoted. Rock inhibitor aliquot was thawed and added fresh to media daily.

Cornea cells were grown as described in Example 2 and harvested by treatment with 0.25% Trypsin as described in Example 4 and replated, with variations (i.e., inclusion of ROCK inhibitor and/or ASC as described below).

After plating, cells were viewed to identify any morphological changes, and specifically whether they regained their polygonal/hexagonal shape, were a mixed population of polygonal and fibroblastic shape, or if they had turned fibroblastic.

Media was changed daily with fresh Rock inhibitor except for "Pretreatment" and "D1" paradigms. After 1 week of culture, RNA was collected and analyzed by QPCR for changes in COL8A1, AQP1, and SLC16A3 mRNA levels. The efficacy of the Rock inhibitor for harvesting cells were tested between 1-20 microM.

trypsin as described above, and were maintained in Rock inhibitor added daily to fresh media.

For the "D1" paradigm, CEC were produced as described in Example 2, harvested using 0.25% trypsin as described above, and cultured in presence of Rock inhibitor for 1 week. Cornea cells were then grown for additional week in the presence or absence of Rock inhibitor, to determine whether the ROCK inhibitor contributed to the maintenance of their morphology.

Example 8 hESC-Derived CEC Maintain Structural Integrity when Harvested in Sheets

To obtain and test sheets of CEC for potential transplantation, hESC-derived CEC were produced as described in Example 2 and cultured on UPCELL tissue culture plates. These culture plates include a temperature sensitive cell culture surface that can release cells as sheet of cells in response to a temperature shift.

Figure 18:
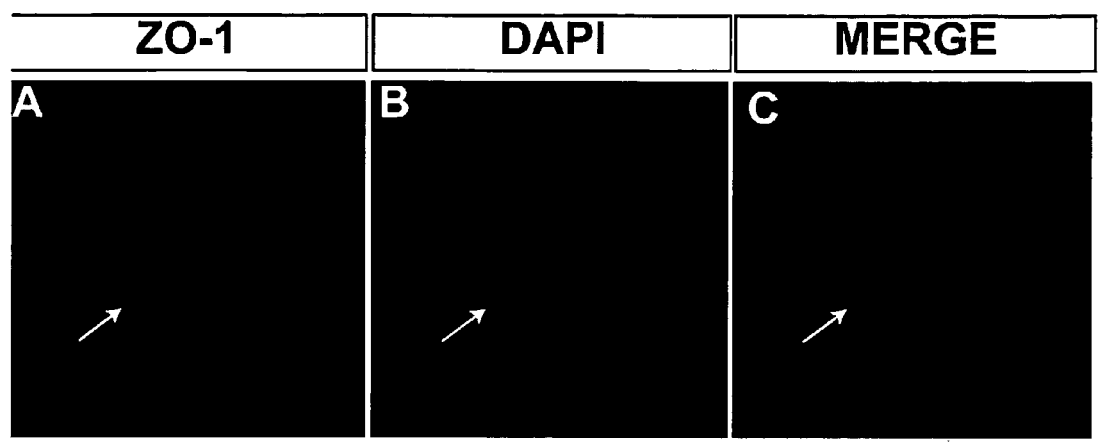
FIG. 18. hESC CEC grown on UPCELL treated tissue culture dish can be removed as a sheet. hESC CEC were grown on UPCELL treated culture dishes, removed, and stained for ZO-1. Arrows indicate hexagonal cell. A. ZO-1 expression (red) indicates that tight junctions are maintained after removal of cell sheet. B. Nuclei are stained with DAPI (blue). C. Merge of ZO-1 and DAPI.

After release from the UPCELL plates, CEC were stained for ZO-1 to test physical integrity of the cell sheet, particularly whether tight junctions were maintained. As shown in FIG. 18, ZO-1 expression indicated that tight junctions were maintained after removal of cell sheet. These results indicate that the CEC can maintain structural integrity when removed as sheets, suggesting that CEC function can be maintained for transplantation of sheets of cells.

Methods

UPCELL tissue culture plates contain a temperature sensitive cell culture surface that release cells as sheet of cells without requiring enzymatic treatment. The manufacturer suggests optimizing the amount of matrix to coat plates and coating at 37 degrees C. even if normally done at room temperature. All solutions were equilibrated at 37 degrees C. prior to contact with the plates to prevent premature cell detachment.

UPCELL tissue culture dishes (10 cm; (Nunc cat #14902) were coated with 2.5×-5× the amount of Matrigel recommended by the manufacturer of Matrigel (BD, cat 354277) at 37 degrees C. for at least one hour.

Cornea cells were produced as described in Example 2 and harvested using 0.25% trypsin for 10 minutes. Cells were then triturated with the trypsin solution to remove cells from well. The enzymatic digestion was stopped with the addition of cornea media. Cells were then centrifuged to pellet cells and resuspended.

Matrigel was quickly removed and cells were plated at the normal density in the presence of 10 microM Rock inhibitor Y-27362 (Wako, cat #253-00513). For all media changes, media was pre-warmed to 37 degrees C. Cells were grown up to two weeks. To detach the cells, incubation at room temperature for 30 minutes (in accord with the manufacturer's directions) was insufficient to achieve full release. However, incubation for 1 hour at 4 degrees C. was sufficient to detach cells as a sheet. After detachment, cells were stained for ZO-1 and microscopically examined.

Example 9

Characterization of Global Gene Expression by CEC and Detection of a "Youthful" Cellular Phenotype This example describes comparison of global gene expression by hESC-derived CEC to donated CEC. The high degree of shared gene expression further confirm the identity of the hESC-derived cells as CEC. Further, the differences in gene expression indicate that the hESC-derived CEC exhibit gene expression characteristic of more "youthful" cells, suggesting that the cells may be even more efficacious for transplantation than donor-derived tissues.

When comparing hESC CEC to adult primary corneal endothelial cells (donated cells), only 792/28374 genes were changed more than 3 fold, indicating the cell types express 97% of all genes at similar levels. This indicates the hESC derived corneal endothelial cells are highly similar to Adult corneal endothelial cells. Additionally, we found that the following corneal endothelial genes were expressed by both populations including but not limited to: ADCY10, ATP1A1, CA2, CFTR, COL8A2, FOXC1, KLF13, PITX2, SLC16A1, SLC16A3, SLC16A7, SLC4A2, SLC9A1, ZO-1.

It was predicted that the hESC CEC would be more youthful than the primary adult CEC, as reflected by indications of decreased level of accumulated oxidative stress and/or DNA damage, as well as increased ability to recapture glutathione compared to CEC isolated from a donor corneal endothelium. Genes exhibiting more than a 3-fold difference expression between hESC-derived CEC and donated CEC are listed in FIG. 20. Among these genes are genes indicative of a more youthful phenotype of the hESC-derived CEC as further described below.

The ability to repair DNA damage decreases with age in older corneas. Indications of this reduced ability can be seen in lower levels of DNA repair pathway molecules such as ATM and OGG1. ATM and OGG1 proteins levels are 1.5 and 1.2 fold lower in older adult corneas (Joyce et al., Invest Ophthalmol Vis Sci. 2011 Mar. 1; 52(3):1641-9). The microarray revealed results similar to youthful corneas, with an approximate 1.9 and 2.8 fold decrease for ATM and OGG1 (for adult CEC compared to hESC-derived CEC), respectively.

A further gene, the enzyme gamma-glutamyltranspeptidase (GGT), is an ectoenzyme important to maintaining corneal dehydration as well recapturing the anti-oxidant glutathione. Redmond et al. (Cornea. 2012 Sep. 27. [Epub ahead of print], doi: 10.1097/ICO.0b013e3182656881) reported that old corneas exhibit 1.7 fold less GGT activity than younger corneas. Consistent with this literature report for youthful CEC, the microarray revealed that GGT7 was downregulated 1.8 fold compared to hESC CEC.

Yet another gene shown in the literature to be reduced in older corneas, BMI1 polycomb ring finger oncogene (BMI1), specifically by 2.5 fold (Wang et al., Mol Vis. 2012; 18:803-15). In the microarray, the adult HCEC had 1.6 fold less BMI1 compared to hESC CEC.

TABLE 5

Genes found by microarray that indicate that hESC CEC are more youthful than Adult primary CEC. A negative value indicates that the expression is lower in the adult CEC compared to the hESC CEC. Literature-reported changes in gene expression for "youthful" CEC as compared to "old" CEC are shown for reference (negative values in this column indicate that expression is lower in the old CEC as compared to young CEC).

| Gene Symbol | Gene name | Accession number | Fold Change [Adult primary CEC vs hESC CEC] | Literature-reported expression fold change |
|---|---|---|---|---|
| ATM | ataxia telangiectasia mutated | NM_000051 | −1.87 | −1.5 (Joyce et al., 2011) |
| BMI1 | BMI1 polycomb ring finger oncogene | NM_005180 | −1.62 | −2.5 (Wang et al., 2012) |

TABLE 5-continued

Genes found by microarray that indicate that hESC CEC are more youthful than Adult primary CEC. A negative value indicates that the expression is lower in the adult CEC compared to the hESC CEC. Literature-reported changes in gene expression for "youthful" CEC as compared to "old" CEC are shown for reference (negative values in this column indicate that expression is lower in the old CEC as compared to young CEC).

| Gene Symbol | Gene name | Accession number | Fold Change [Adult primary CEC vs hESC CEC] | Literature-reported expression fold change |
|---|---|---|---|---|
| GGT5 | gamma-glutamyltransferase 5 | NM_001099781 | −1.86 | −1.7 (Redmond et al., 2012) |
| OGG1 | 8-oxoguanine DNA glycosylase | NM_003656 | −2.80 | −1.2 (Joyce et al., 2011) |

Methods hESC corneal endothelium was grown in three separate experiments as described in Example 2 but with an extra week of growth (PD1T 2 week). Adult Human Corneal Endothelium was isolated and expanded in culture as previously described (Joyce et al., Molecular Vision 2010; 16:897-906) and collected at Passage 0. RNA was isolated using RNA easy RNA isolation kit (Qiagen, cat#74104) along with DNAase treatment (Qiagen, cat#79254) and processed by manufacturer's directions. RNA samples were further processed for hybridization to Affymetrix' Human Exome ST arrays at the University of Miami Genomics Core Facility. Raw data were normalized and analyzed using Genespring GX12 and GeneGo Metacore software applications. After normalization, probes were filtered using 2 different criteria: expression values between 20 and $99^{th}$ percentile and at least 2 out of the 3 samples in at least one condition passed these criteria. 28374 out of 28869 total probes (98%) were used for subsequent analysis. Genes were compared using an unpaired T Test with Asymptotic p-value comparison. Multiple testing correction was done with Benjamini-Hochberg.

Example 10

Improved CEC Purity Using Magnetic Bead Subtraction of Other Cell Types

This example demonstrates that cell subtraction using microbeads may increase the purity of CEC derived from hESC or NCSC. Magnetic bead subtraction was utilized to remove non-CEC cells from culture and thereby improve purity of CEC cultures.

Antibody-coupled magnetic beads were used to preferentially capture non-CEC from the culture (see, e.g., Peh et al., Int J Biomater. 2012; 2012:601302). Specifically, microbeads coupled to an anti-CD271 antibody were utilized. CEC cultures were produced without passaging (FIG. 21A), with passaging at day 10 (FIG. 21B), or with passaging and removal of CD271+ cells by magnetic bead separation which produced cultures that appeared to be somewhat less uniform in hexagonal/polygonal shape (FIG. 21C). Flow cytometry confirmed that cells expressing higher levels of CD271 were successfully removed, with 23% of cells being positive for CD271 expression before subtraction (FIG. 21D) but only 2% of cells being positive for CD271 after subtraction (FIG. 21E).

Applicants also observed that some hESC-derived CEC expressed low levels of CD271 (detected by both flow cytometry and from the microarray data) and based thereon it is thought that other markers may be even more effective for improving purity. Nonetheless, the results above generally validate the use of magnetic bead subtraction with hESC-derived CEC and indicate that the method would be similarly effective in removing cells that express other markers, such as pluripotent cell markers (e.g., SSEA-1, TRA-1-60, and/or SSEA-4, etc.), epithelial cell markers (e.g., CD326), or NCSC markers, whether individually or in combination.

Methods

CD271+ (nerve growth factor receptor) cells were depleted from hESC CEC cultures using the CD271 microbeads (Militenyi Biotec, cat#130-097-128) according to the manufacturer's directions. Briefly, hESC CEC were trypsinized to remove cells from plate. After centrifugation to remove trypsin, cells were resuspended and put through the Pre-separation Filter (Militenyi Biotec, Cat 130-041-407) to remove any cell clumps. A portion of the unsorted cells were saved for Flow Cytometry analysis. Cells were subsequently incubated with the CD271 microbeads and then depleted using the LD Columns (Militenyi Biotec, #130-042-901). A portion of the sorted cells were analyzed by Flow Cytometry, with the remainder being immediately plated. There are two controls for the growth of the cells, first untouched hESC CEC were used as well as hESC CEC that were trypsinized and replated (Passage 1).

Flow Cytometry analysis was performed comparing unsorted and sorted cells. CD271-APC antibody (Militenyi Biotec, cat#130-091-884) at 1:11 was utilized to detect expression of CD271 in unsorted and sorted cells. The events of unlabeled cells for unsorted and sorted cells were used to gate at 99.5%.

Example 11

Clinical Testing of CEC

The example describes experiments to establish the safety of transplanted hES-derived corneal endothelial cells. Clinical grade corneal endothelial (CE) cells are generated at a GMP-compliant clinical production facility. CE cells are subjected to strict validation and quality controls prior to final release of the CE cell suspension for transplantation. Each lot of CE cells undergoes a battery of quality control safety testing including testing for sterility, presence of mycoplasma, presence of endotoxins, absence of pluripotent stem cells, and karyotyping. Identity is confirmed by DNA fingerprinting, appropriate endothelial morphology, and marker expression consistent with CE cells. Purity is determined by immunohistochemical staining for the acceptable levels and distribution of CE-specific proteins including Na+K+ATPase pump, ZO-1, and KLF13. In addition, each lot is characterized by qRT-PCR to demonstrate downregulation of hESC markers (OCT-4, NANOG, and Sox-2) and upregulation of CE cell specific genes in accordance with validated specifications.

Corneal endothelial cells produced according to the methods described herein are used in non-human animal models to establish potential safety and/or efficacy for human use. Pharmaceutical compositions of cells are used in non-human animal models that assess CEC function. Cells (e.g., as a sheets or suspension) may be surgically administered to the eye of a non-human animal. For example, CEC compositions may be used in rabbit models as described in one or more of Honda et al., Arch Ophthalmol. 2009 October; 127(10):1321-6; Hitani et al., Mol Vis. 2008 Jan. 3; 14:1-9; Mimura et al., (Invest Ophthalmol Vis Sci. 2005; 46:3637-3644; Hsuie et al., Transplantation 2006; 81: 473-476; Lai et al., Transplantation 2007; 84: 1222-1232; Shimmura et al., Br J Ophthalmol 2005; 89:134-137; Chen et al., Molecular Vision 2011; 17:2148-2156; and Gospodrowicz et al., Proc. Natl. Acad. Sci. USA, Vol. 76, No. 1, pp. 464-468, January 1979; and/or may be used in rodent (e.g., mouse/rat) models as described in Hayashi et al., Investigative Ophthalmology & Visual Science, July 2009, Vol. 50, No. 7, pg. 3151-3158; Mimura et al., Experimental Eye Research 79 (2004) 231-237; Tchah, J Korean Med Sci. 1992 December; 7(4):337-42; and/or may be used in non-human primate models as described in Koizumi et al., Invest Ophthalmol Vis Sci. 2007; 48:4519-4526); Koizumi et al., Cornea 2008; 27(Suppl. 1):S48-S55; and/or in a human or non-human as described in Peh et al., Transplantation. 2011 Apr. 27; 91(8):811-9. Each foregoing publication is incorporated by reference herein in its entirety.

Corneal endothelial cells produced according to the methods described herein are used for patient therapy as follows: (i) patients initially receive an immunosuppressive treatment (e.g., steroids); (ii) patients are optionally assigned to a treatment cohort (e.g., four cohorts of three patients each); (iii) escalating doses of cells are administered to the cohorts (preferably unilaterally, i.e., to one of each patient's eyes). Each patient's clinical course is monitored post-transplant, e.g., over the first 6 weeks post-transplant, and optionally at further (prior or subsequent) timepoints, preferably for at least one year. Primary evaluation of patients includes monitoring for adverse events (AE) and dose-limiting toxicities (DTL) including assays for detection of immune-mediated pathology, teratoma formation, and/or abnormal blood vessel growth. Patients are additionally assessed for secondary endpoints including efficacy with regard to intraocular pressure (IOP), visual acuity, and/or endothelial cell count of the graft. Long term follow-up preferably continues for up to 15 years or more to evaluate long term affects. As satisfactory safety data are obtained from the initial patient cohorts, unilateral or bilateral treatment of additional patients is undertaken. Additionally, patients in the initial unilateral cohorts may be offered the opportunity to receive therapy in the previously untreated cornea.

The invention claimed is:

1. A method of producing corneal endothelial cells (CECs), comprising
   contacting embryonic stem (ES) cells with Noggin and 4-[4-(1,3-benzodioxol-5-yl)-5-(2-pyridinyl)-1H-imidazol-2-yl]benzamide (SB431542) to induce differentiation of the ES cells into neural crest stem cells (NCSCs); and
   contacting the NCSCs with dickkopf-related protein 2 (DKK2), and platelet-derived growth factor subunit B (PDGFB), to induce differentiation of the NCSCs into CECs that express Na+/K+ ATPase, ZO-1, KLF13, AQP1, Collagen VIII, SLC16A3, CFTR, NBC1, Carbonic anhydrase II (CA2), Anion exchanger 2 (AE2/SCL4A2), Solute Carrier Family 16 A1 (SCL16A1), SCL16A3, Carbonic anhydrase 12 (CA12), Carbonic Anhydrase 4 (CA4), cystic fibrosis transmembrane conductance regulator (CFTR) and transcription factor FoxC1.

2. The method of claim 1, wherein the method comprises contacting NCSCs with DKK2 having a concentration of between 2 ng/ml and 20 ng/ml.

3. The method of claim 1, wherein the method comprises contacting NCSCs with PDGFB having a concentration of between 2 ng/ml and 20 ng/ml.

4. The method of claim 1, further comprising culturing the CECs on a matrix.

5. The method of claim 4, wherein the matrix is selected from: laminin, fibronectin, vitronectin, proteoglycan, entactin, collagen, collagen I, collagen IV, collagen VIII, heparan sulfate, a soluble preparation from Engelbreth-Holm-Swarm (EHS) mouse sarcoma cells, a human basement membrane extract, and any combination thereof.

6. The method of claim 4, wherein the matrix is a soluble preparation obtained from EHS mouse sarcoma cells (MATRIGEL®).

7. The method of claim 1, wherein the NCSCs express Sox10, AP2, HNK1, Pax3, PAX7 and p75 (NGFR).

8. The method of claim 1, wherein the CECs do not express vWF and CD31.

9. The method of claim 1, wherein the ES cells are human ES cells and the CECs are human CECs.

* * * * *